(12) United States Patent
Nazareth et al.

(10) Patent No.: US 8,278,109 B2
(45) Date of Patent: Oct. 2, 2012

(54) HYPERGLYCOSYLATED HCG DETECTION DEVICE

(75) Inventors: Albert R. Nazareth, Mercerville, NJ (US); Timothy Snowden, Howell, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 217 days.

(21) Appl. No.: 12/704,892

(22) Filed: Feb. 12, 2010

(65) Prior Publication Data

US 2011/0201122 A1 Aug. 18, 2011

(51) Int. Cl.
*G01N 33/76* (2006.01)
*G01N 33/48* (2006.01)
*G01N 33/53* (2006.01)
*G01N 33/543* (2006.01)
*G01N 33/558* (2006.01)
*G01N 30/00* (2006.01)

(52) U.S. Cl. .......... 436/65; 436/510; 436/514; 436/518; 436/535; 436/63; 436/86; 436/87; 436/164; 436/165; 436/169; 436/810; 422/400; 422/420; 422/69; 435/7.1; 435/7.5; 435/805; 435/970

(58) Field of Classification Search .......... 436/510, 436/514, 518, 524, 528, 535, 63, 65, 86, 436/87, 164, 165, 169, 805, 810; 422/400, 422/420, 69; 435/4, 7.1, 7.5, 970, 805
See application file for complete search history.

(56) References Cited

U.S. PATENT DOCUMENTS

| | | | |
|---|---|---|---|
| 5,739,041 A * | 4/1998 | Nazareth et al. | 436/518 |
| 6,319,676 B1 * | 11/2001 | Nazareth et al. | 435/7.5 |
| 6,627,457 B2 * | 9/2003 | Pandian et al. | 436/501 |
| 6,767,714 B2 * | 7/2004 | Nazareth et al. | 435/7.5 |
| 7,045,342 B2 * | 5/2006 | Nazareth et al. | 435/287.1 |
| 7,666,683 B1 * | 2/2010 | Cole | 436/65 |
| 7,897,362 B2 * | 3/2011 | Pandian et al. | 435/7.92 |
| 2003/0119202 A1 | 6/2003 | Kaylor et al. | |
| 2006/0105411 A1 | 5/2006 | Cole | |
| 2008/0213920 A1 | 9/2008 | Nazareth et al. | |
| 2009/0075293 A1 | 3/2009 | Pevsner et al. | |
| 2009/0196792 A1 | 8/2009 | Raj et al. | |
| 2009/0305436 A1 * | 12/2009 | Plummer et al. | 436/510 |
| 2010/0129935 A1 * | 5/2010 | Maddison | 436/510 |

* cited by examiner

*Primary Examiner* — Maureen Wallenhorst
(74) *Attorney, Agent, or Firm* — Ryan W. Cagle; Stephen B. Shear

(57) ABSTRACT

The present invention related to a pregnancy test device that can selectively detect hyperglycosylated human chorionic gonadotropin (hCG-H) in a liquid sample. The sample can be deposited on a proximal portion of the device for transport to a distal portion of the device. The device can include a release medium formed of a first material and including a detectable label thereon and a capture medium, including a capture site, in fluid communication with the release medium and formed of a second, different material. At least one of the release medium and the capture medium includes a binding member that exhibits a moderate to high affinity for hCG-H and is selectively or preferentially reactive with hCG-H.

35 Claims, 26 Drawing Sheets

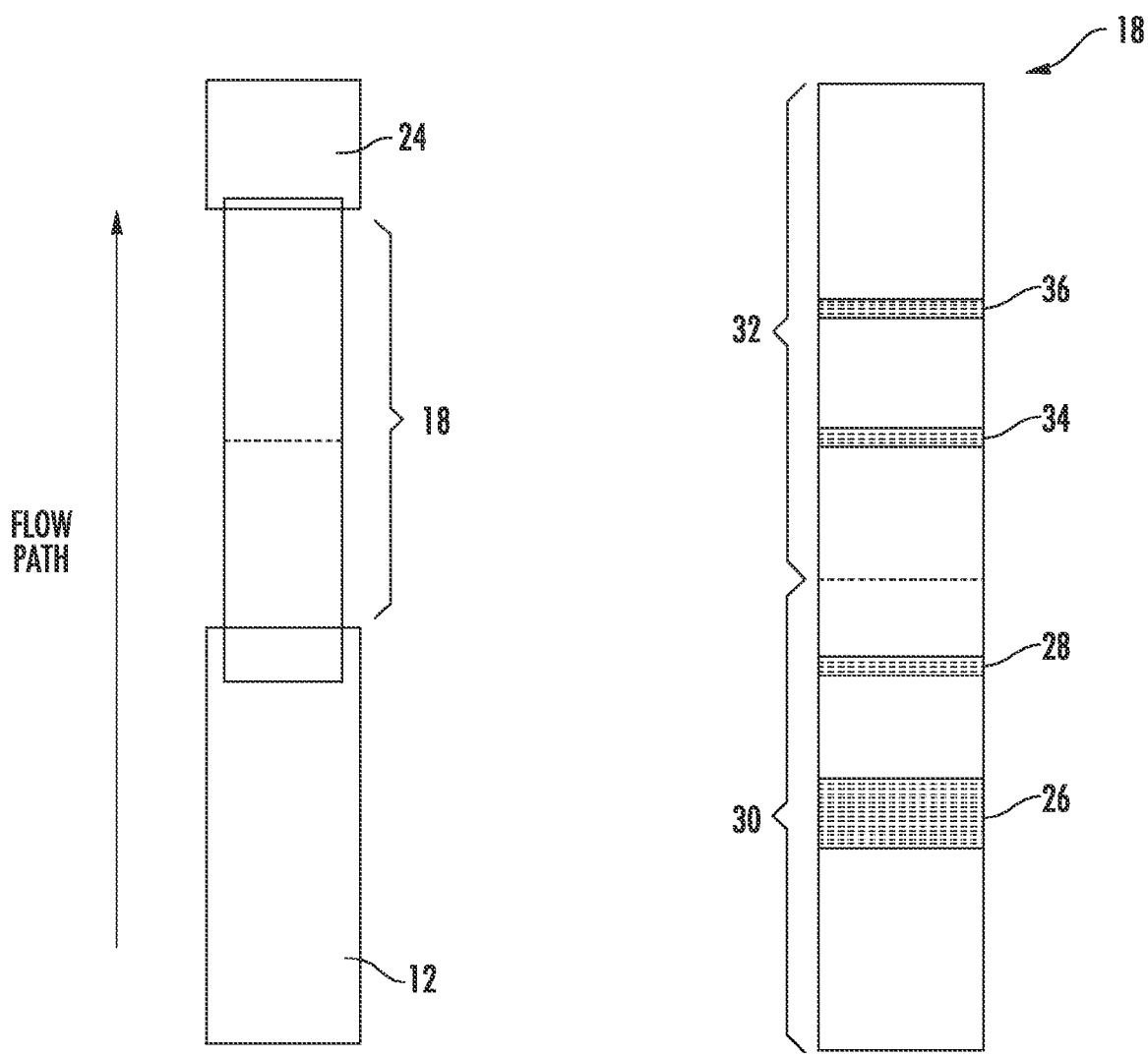

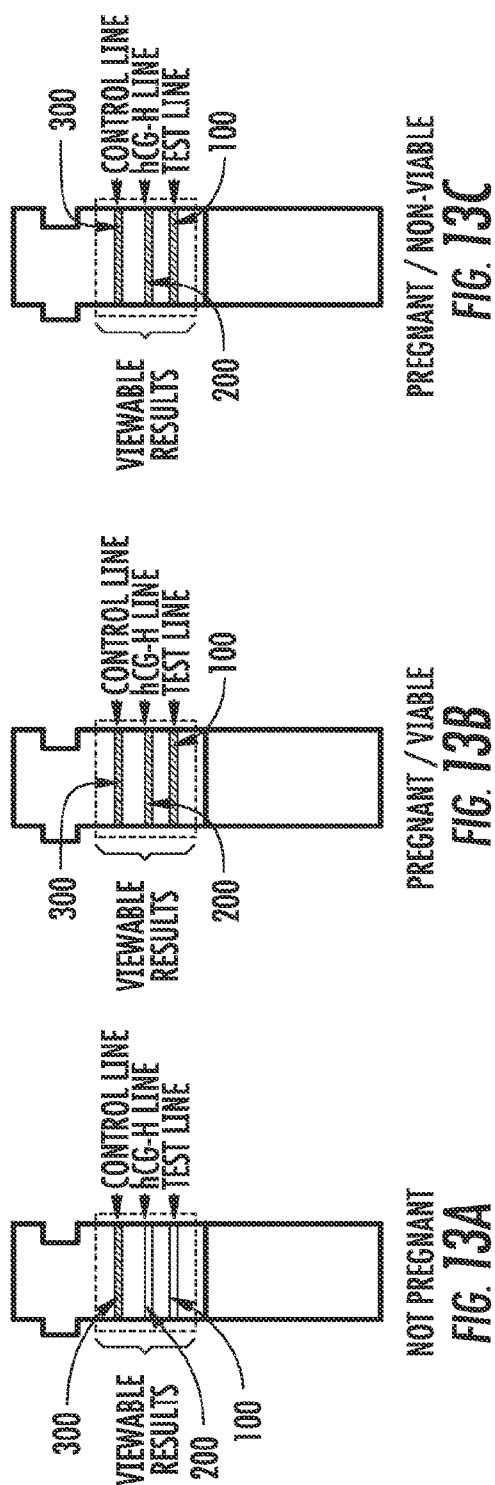
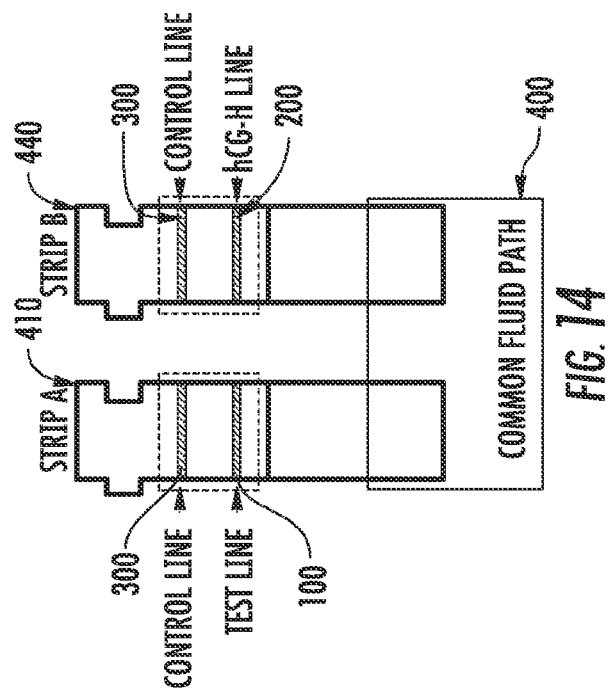

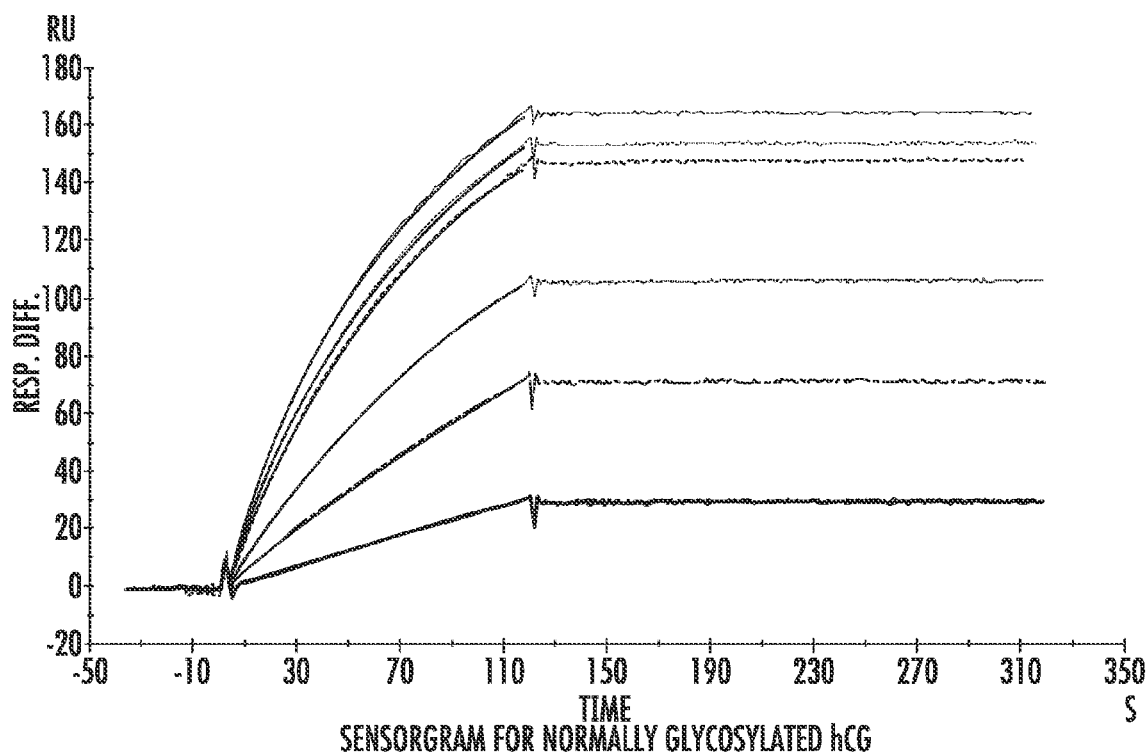
FIG. 16 SENSORGRAM FOR NORMALLY GLYCOSYLATED hCG
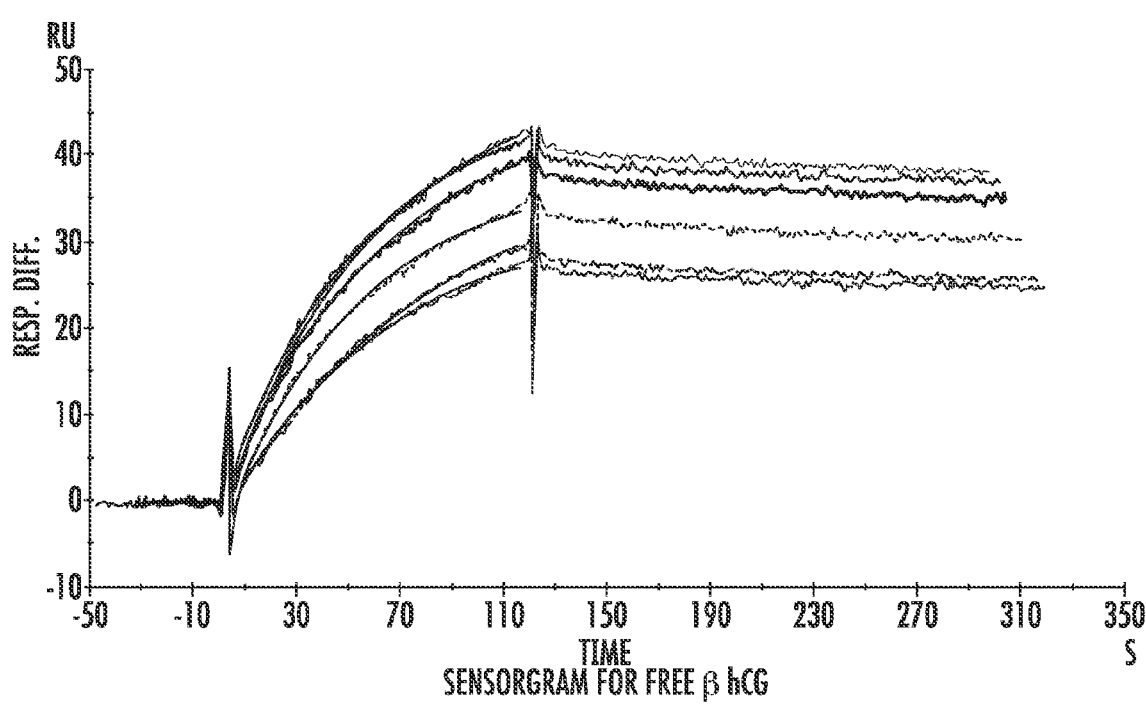
FIG. 17 SENSORGRAM FOR FREE β hCG

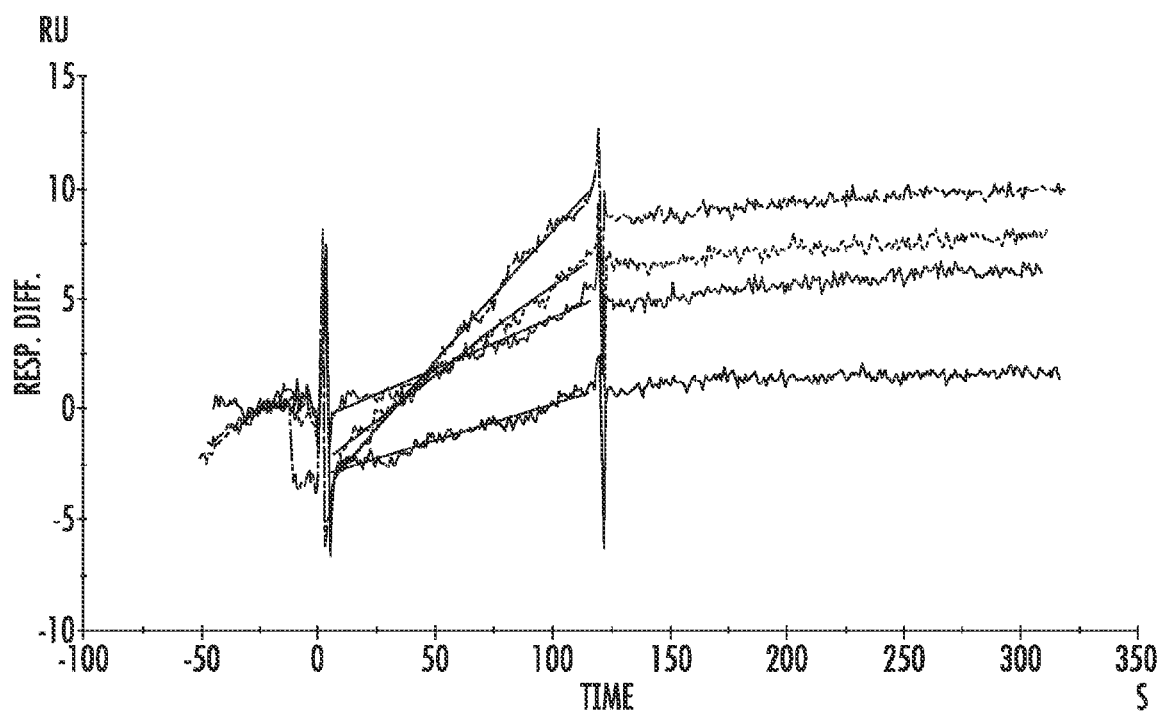
FIG. 26 SENSORGRAM FOR B152 ON NORMALLY GLYCOSYLATED hCG
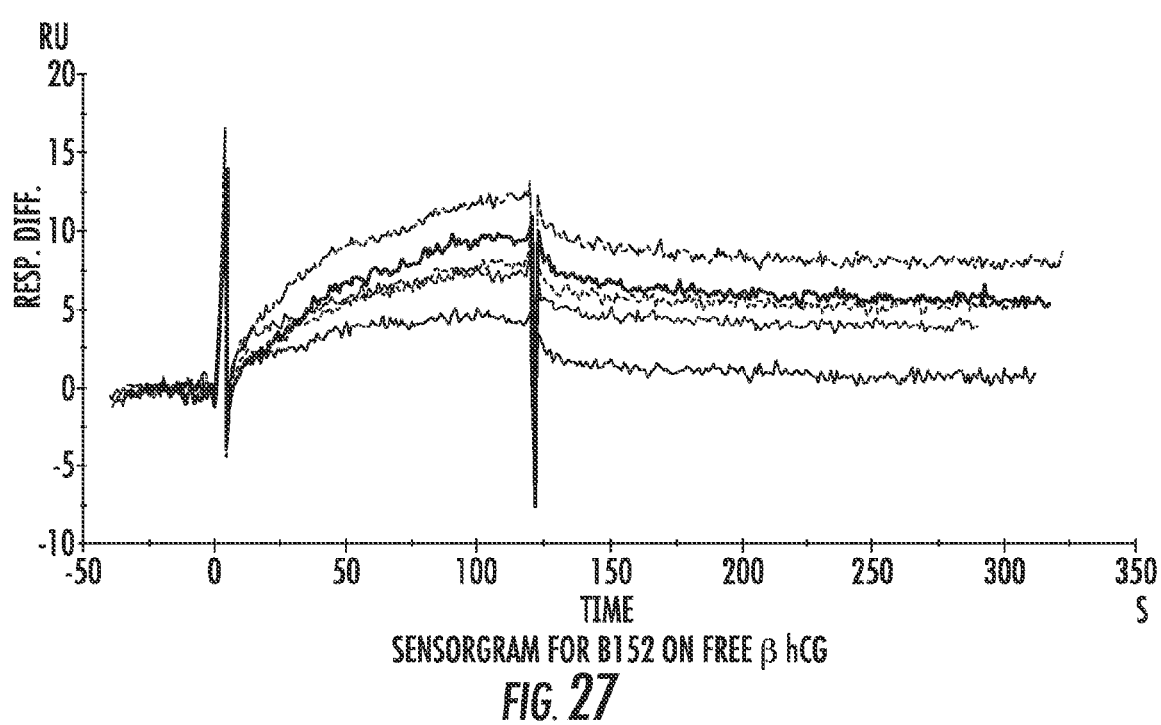
FIG. 27 SENSORGRAM FOR B152 ON FREE β hCG

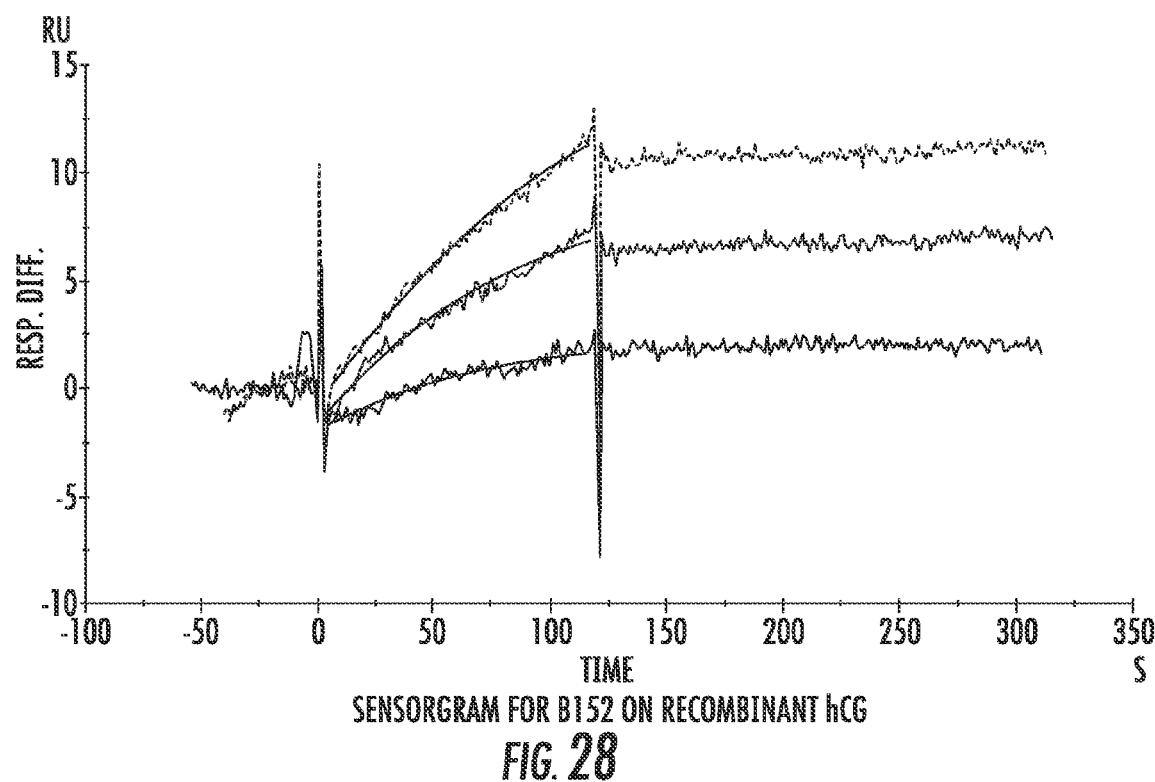
FIG. 28 SENSORGRAM FOR B152 ON RECOMBINANT hCG
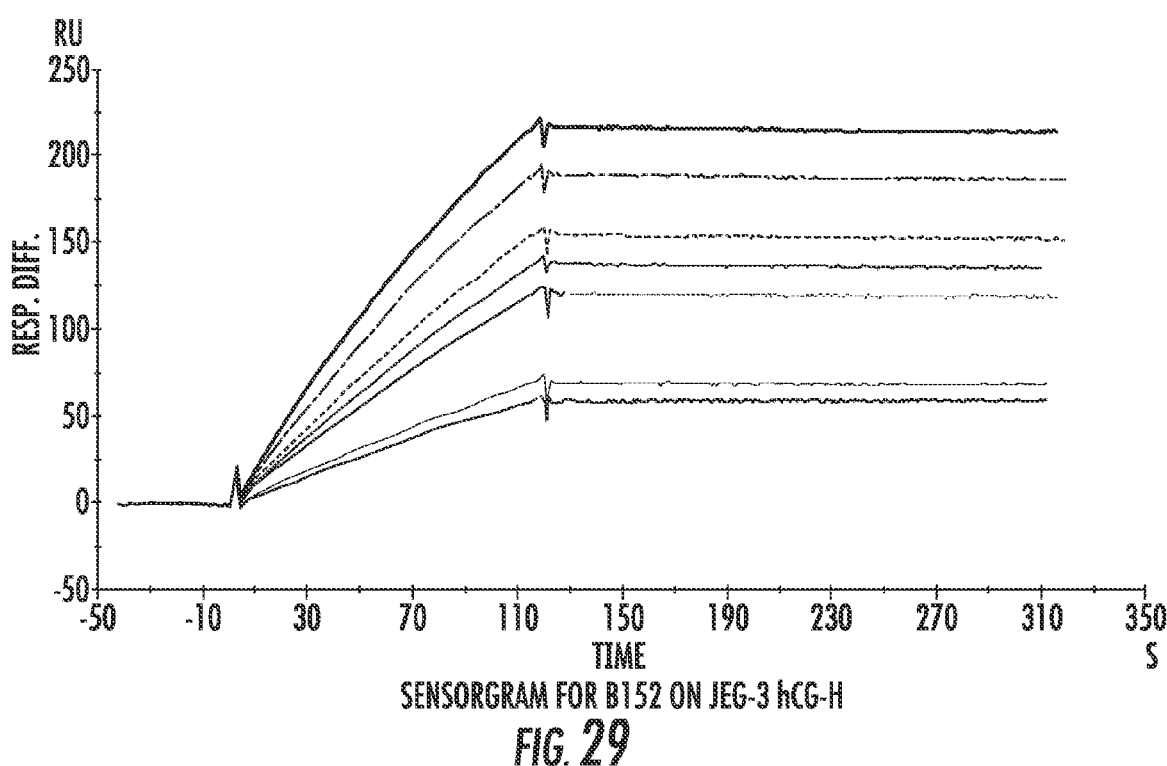
FIG. 29 SENSORGRAM FOR B152 ON JEG-3 hCG-H

NEGATIVE URINE SAMPLES

| SUBJECT ID | LH (mIU/mL) | hCG (mIU/mL) | PROTOTYPE DEVICES | | | | | |
|---|---|---|---|---|---|---|---|---|
| | | | FR2 | FR1 | CCF01 / 3E8 | CCF01 / 4D8 | 11D6-2B10 / 4D8 |
| 4 | 0.562 | <1.0 | – | – | – | – | – |
| 8 | 0.368 | <1.0 | – | – | – | – | – |
| 17 | 0.852 | <1.0 | – | – | – | – | – |
| 21 | 0.214 | <1.0 | – | – | – | – | – |
| 22 | 0.301 | <1.0 | – | – | – | – | – |
| 31 | 59.5 | <1.0 | – | – | – | – | – |
| 59 | 39.3 | <1.0 | – | – | – | – | – |
| 62 | 47.7 | <1.0 | – | – | – | – | – |
| 63 | 44.9 | <1.0 | – | – | – | – | – |
| 67 | 54.2 | <1.0 | – | – | – | – | – |

3 MINUTE VISUAL READ

| + | POSITIVE |
| +/- | AMBIGUOUS |
| – | NEGATIVE |

FIG. 31

LH SURGE SAMPLES

| SUBJECT ID | SAMPLE DATE | LH (mIU/mL) | PROTOTYPE DEVICES ||||||
|---|---|---|---|---|---|---|---|---|
| | | | FR2 | FR1 | CCF01 / 3E8 | CCF01 / 4D8 | 11D6-2B10 / 4D8 |
| VEGDA | 6/11/2007 | 138 | | | | | |
| STABR | 4/13/2007 | >200 | | | | | |
| CALTA | 3/24/2007 | 143 | | | | | |
| FROKA | 6/29/2007 | 155 | | | | | |
| LIHUI | 4/15/2007 | >200 | | | | | |
| EDWAN | 5/8/2007 | 194 | | | | | |
| HAWJA | 4/24/2007 | 184 | | | | | |
| WINCH | 7/3/2007 | 178 | | | | | |
| KAFCO | 4/1/2007 | 148 | | | | | |
| CRUNO | 4/5/2007 | 194.4 | | | | | |

| 3 MINUTE VISUAL READ | |
|---|---|
| POSITIVE | + |
| AMBIGUOUS | +/- |
| NEGATIVE | - |

FIG. 32

| SUBJECT ID | SAMPLE DATE | PITUITARY hCG (mIU/mL) | FR2 | PROTOTYPE DEVICES | | | |
|---|---|---|---|---|---|---|---|
| | | | | (CF01 / 3E8 | (CF01 / 3E8) | (CF01 / 4D8) | 11D6-2B10 / 4D8 |
| 26 | 6/11/2007 | 14.7 | + | | | | |
| 57 | 4/13/2007 | 2.4 | + | | | | |
| 66 | 3/24/2007 | 3.57 | + | | | | |
| 115 | 6/29/2007 | 28.5 | + | | | + | |
| 161 | 4/15/2007 | 6.73 | + | | | | |
| 172 | 5/8/2007 | 7.67 | | | | | |
| 199 | 4/24/2007 | 8.82 | + | | | | |
| 212 | 7/3/2007 | 6.82 | | | | | |
| 229 | 4/7/2007 | 11.6 | | | | | |
| 253 | 4/5/2007 | 8.33 | | | | | |

3 MINUTE VISUAL READ

| POSITIVE | + |
| --- | --- |
| AMBIGUOUS | +/- |
| NEGATIVE | |

*FIG. 33*

| SUBJECT ID | SAMPLE DATE | DAY | TOTAL hCG (mIU/mL) | H-hCG (mIU/mL) | PROTOTYPE DEVICES ||||| 
|---|---|---|---|---|---|---|---|---|---|
| | | | | | FR2 | FR1 | CCF01 / 3E8 | CCF01 / 4D8 | 11D6-2B10 / 4D8 |
| DJEAM | 5/18/2007 | EMP-6 | 4.65 | | +/- | - | - | - | +/- |
| | 5/19/2007 | EMP-5 | 11.7 | | + | +/- | +/- | - | +/- |
| | 5/20/2007 | EMP-4 | 18.5 | | + | + | +/- | +/- | + |
| | 5/21/2007 | EMP-3 | 74.9 | | + | + | + | + | + |
| | 5/22/2007 | EMP-2 | 82.4 | | + | + | + | + | + |
| | 5/23/2007 | EMP-1 | 98.1 | | + | + | + | + | + |
| | 5/24/2007 | EMP | 223 | | + | + | + | + | + |

| SUBJECT ID | SAMPLE DATE | DAY | TOTAL hCG (mIU/mL) | H-hCG (mIU/mL) | PROTOTYPE DEVICES |||||
|---|---|---|---|---|---|---|---|---|---|
| | | | | | FR2 | FR1 | CCF01 / 3E8 | CCF01 / 4D8 | 11D6-2B10 / 4D8 |
| GRACA | 1/21/2007 | EMP-6 | 27 | | + | + | +/- | +/- | + |
| | 1/22/2007 | EMP-5 | 28 | | + | + | + | +/- | + |
| | 1/23/2007 | EMP-4 | 34 | | + | + | + | + | + |
| | 1/24/2007 | EMP-3 | 81 | | + | + | + | + | + |
| | 1/25/2007 | EMP-2 | 106 | | + | + | + | + | + |
| | 1/26/2007 | EMP-1 | 78 | | + | + | + | + | + |
| | 1/27/2007 | EMP | 316 | | + | + | + | + | + |

| SUBJECT ID | SAMPLE DATE | DAY | TOTAL hCG (mIU/mL) | H-hCG (mIU/mL) | PROTOTYPE DEVICES |||||
|---|---|---|---|---|---|---|---|---|---|
| | | | | | FR2 | FR1 | CCF01 / 3E8 | CCF01 / 4D8 | 11D6-2B10 / 4D8 |
| THASH | 1/31/2007 | EMP-6 | 113 | | +/- | - | + | + | + |
| | 2/1/2007 | EMP-5 | 226 | | + | + | + | + | + |
| | 2/2/2007 | EMP-4 | 363 | | + | + | + | + | + |
| | 2/3/2007 | EMP-3 | 590 | | + | + | + | + | + |
| | 2/4/2007 | EMP-2 | 498 | | + | + | + | + | + |
| | 2/5/2007 | EMP-1 | 1387 | | + | + | + | + | + |
| | 2/6/2007 | EMP | 2887 | | + | + | + | + | + |

| SUBJECT ID | SAMPLE DATE | DAY | TOTAL hCG (mIU/mL) | H-hCG (mIU/mL) | PROTOTYPE DEVICES |||||
|---|---|---|---|---|---|---|---|---|---|
| | | | | | FR2 | FR1 | CCF01 / 3E8 | CCF01 / 4D8 | 11D6-2B10 / 4D8 |
| HOKIM | 3/3/2007 | EMP-6 | 21 | | + | + | +/- | - | +/- |
| | 3/4/2007 | EMP-5 | 24 | | + | + | + | + | + |
| | 3/5/2007 | EMP-4 | 35 | | + | + | + | + | + |
| | 3/6/2007 | EMP-3 | 189 | | + | + | + | + | + |
| | 3/7/2007 | EMP-2 | 515 | | + | + | + | + | + |
| | 3/8/2007 | EMP-1 | 597 | | + | + | + | + | + |
| | 3/9/2007 | EMP | 801 | | + | + | + | + | + |

| SUBJECT ID | SAMPLE DATE | DAY | TOTAL hCG (mIU/mL) | H-hCG (mIU/mL) | PROTOTYPE DEVICES |||||
|---|---|---|---|---|---|---|---|---|---|
| | | | | | FR2 | FR1 | CCF01 / 3E8 | CCF01 / 4D8 | 11D6-2B10 / 4D8 |
| CALTA | 6/17/2007 | EMP-6 | <1.0 | | - | - | - | - | - |
| | 6/18/2007 | EMP-5 | 2.27 | | +/- | - | - | - | +/- |
| | 6/19/2007 | EMP-4 | 7.61 | | + | + | + | + | + |
| | 6/20/2007 | EMP-3 | 20.1 | | + | + | + | + | + |
| | 6/21/2007 | EMP-2 | 21.5 | | + | + | +/- | + | + |
| | 6/22/2007 | EMP-1 | 63.4 | | + | + | + | + | + |
| | 6/23/2007 | EMP | 137 | | + | + | + | + | + |

*FIG. 34*

| SUBJECT ID | SAMPLE DATE | DAY | TOTAL hCG (mIU/mL) | H-hCG (mIU/mL) | PROTOTYPE DEVICES ||||| 
| --- | --- | --- | --- | --- | --- | --- | --- | --- | --- |
| | | | | | FR2 | FR1 | CCF01 / 3E8 | CCF01 / 4D8 | 11D6-2B10 / 4D8 |
| WIMA | 8/25/2006 | EMP-5 | 20.1 | | +/- | - | - | - | - |
| | 8/26/2006 | EMP-4 | 27.2 | | + | + | + | +/- | +/- |
| | 8/27/2006 | EMP-3 | 37.5 | | + | + | + | + | + |
| | 8/28/2006 | EMP-2 | 41 | | + | + | + | + | + |
| | 8/29/2006 | EMP-1 | 142 | | + | + | + | +/- | +/- |

| SUBJECT ID | SAMPLE DATE | DAY | TOTAL hCG (mIU/mL) | H-hCG (mIU/mL) | PROTOTYPE DEVICES ||||| 
| --- | --- | --- | --- | --- | --- | --- | --- | --- | --- |
| | | | | | FR2 | FR1 | CCF01 / 3E8 | CCF01 / 4D8 | 11D6-2B10 / 4D8 |
| MCJE | 8/22/2006 | EMP-5 | 40 | | - | - | - | - | - |
| | 8/23/2006 | EMP-4 | 30.2 | | + | +/- | - | +/- | +/- |
| | 8/24/2006 | EMP-3 | 111 | | + | +/- | - | +/- | +/- |
| | 8/25/2006 | EMP-2 | 142 | | + | + | +/- | + | + |
| | 8/26/2006 | EMP-1 | 152 | | + | + | + | + | + |

| SUBJECT ID | SAMPLE DATE | DAY | TOTAL hCG (mIU/mL) | H-hCG (mIU/mL) | PROTOTYPE DEVICES ||||| 
| --- | --- | --- | --- | --- | --- | --- | --- | --- | --- |
| | | | | | FR2 | FR1 | CCF01 / 3E8 | CCF01 / 4D8 | 11D6-2B10 / 4D8 |
| BRNI | 7/7/2007 | EMP-5 | 28.2 | | +/- | - | - | +/- | +/- |
| | 7/8/2007 | EMP-4 | 41 | | + | +/- | - | +/- | + |
| | 7/9/2007 | EMP-3 | 95.2 | | + | + | +/- | + | + |
| | 7/10/2007 | EMP-2 | 147 | | + | + | + | + | + |
| | 7/11/2007 | EMP-1 | 142 | | + | + | + | + | + |

| SUBJECT ID | SAMPLE DATE | DAY | TOTAL hCG (mIU/mL) | H-hCG (mIU/mL) | PROTOTYPE DEVICES ||||| 
| --- | --- | --- | --- | --- | --- | --- | --- | --- | --- |
| | | | | | FR2 | FR1 | CCF01 / 3E8 | CCF01 / 4D8 | 11D6-2B10 / 4D8 |
| PABE | 7/13/2007 | EMP-6 | 27.6 | | + | +/- | +/- | +/- | +/- |
| | 7/14/2007 | EMP-5 | 28.6 | | + | + | +/- | + | + |
| | 7/15/2007 | EMP-4 | 72.5 | | + | + | + | + | + |
| | 7/16/2007 | EMP-3 | 43.6 | | + | + | + | + | + |
| | 7/17/2007 | EMP-2 | 216 | | + | + | + | + | + |

| SUBJECT ID | SAMPLE DATE | DAY | TOTAL hCG (mIU/mL) | H-hCG (mIU/mL) | PROTOTYPE DEVICES ||||| 
| --- | --- | --- | --- | --- | --- | --- | --- | --- | --- |
| | | | | | FR2 | FR1 | CCF01 / 3E8 | CCF01 / 4D8 | 11D6-2B10 / 4D8 |
| MOBR | 1/10/2007 | EMP-4 | 31.7 | | +/- | - | - | - | +/- |
| | 1/11/2007 | EMP-3 | 61.6 | | + | + | + | + | + |
| | 1/12/2007 | EMP-2 | 103 | | + | + | + | + | + |
| | 1/13/2007 | EMP-1 | 238 | | + | + | + | + | + |
| | 1/14/2007 | EMP | 418 | | + | + | + | + | + |

3 MINUTE VISUAL READ

| | |
| --- | --- |
| + | POSITIVE |
| +/- | AMBIGUOUS |
| - | NEGATIVE |

FIG. 35

| SUBJECT ID | SAMPLE DATE | DAY | TOTAL hCG (mIU/mL) | H-hCG (mIU/mL) | PROTOTYPE DEVICES ||||
|---|---|---|---|---|---|---|---|---|---|
| | | | | | FR2 | FR1 | CCF01 / 3E8 | CCF01 / 4D8 | 11D6-2B10 / 4D8 |
| THME | 10/19/2006 | | 3 | | - | - | - | - | - |
| | 10/20/2006 | | 7 | | + | +/- | - | - | - |
| | 10/21/2006 | | 14.2 | | + | +/- | - | - | - |
| | 10/22/2006 | | N/A | | | | | | |
| | 10/23/2006 | | 13.3 | | + | +/- | - | - | - |
| | 10/24/2006 | | N/A | | | | | | |
| | 10/25/2006 | | N/A | | | | | | |
| | 10/26/2006 | | 1.7 | | - | - | - | - | - |
| | 10/27/2006 | | 1.2 | | - | - | - | - | - |
| | 10/28/2006 | | <1 | | - | - | - | - | - |

| SUBJECT ID | SAMPLE DATE | DAY | TOTAL hCG (mIU/mL) | H-hCG (mIU/mL) | PROTOTYPE DEVICES ||||
|---|---|---|---|---|---|---|---|---|---|
| | | | | | FR2 | FR1 | CCF01 / 3E8 | CCF01 / 4D8 | 11D6-2B10 / 4D8 |
| BRDA | 1/8/2007 | | 1 | | +/- | - | - | - | - |
| | 1/9/2007 | | 3.8 | | + | +/- | - | - | - |
| | 1/10/2007 | | 2.1 | | + | +/- | - | - | - |
| | 1/11/2007 | | 7.6 | | + | +/- | - | - | - |
| | 1/12/2007 | | 2.1 | | - | - | - | - | - |
| | 1/13/2007 | | 2 | | - | - | - | - | - |

| SUBJECT ID | SAMPLE DATE | DAY | TOTAL hCG (mIU/mL) | H-hCG (mIU/mL) | PROTOTYPE DEVICES ||||
|---|---|---|---|---|---|---|---|---|---|
| | | | | | FR2 | FR1 | CCF01 / 3E8 | CCF01 / 4D8 | 11D6-2B10 / 4D8 |
| BEQU | 7/4/2007 | | 1 | | - | - | - | - | - |
| | 7/5/2007 | | N/A | | | | | | |
| | 7/6/2007 | | 1.5 | | - | - | - | - | - |
| | 7/7/2007 | | 15 | | + | +/- | - | +/- | - |
| | 7/8/2007 | | <1 | | - | - | - | - | - |
| | 7/9/2007 | | 1.4 | | - | - | - | - | - |
| | 7/10/2007 | | N/A | | | | | | |
| | 7/11/2007 | | N/A | | | | | | |
| | 7/12/2007 | | N/A | | | | | | |

| SUBJECT ID | SAMPLE DATE | DAY | TOTAL hCG (mIU/mL) | H-hCG (mIU/mL) | PROTOTYPE DEVICES ||||
|---|---|---|---|---|---|---|---|---|---|
| | | | | | FR2 | FR1 | CCF01 / 3E8 | CCF01 / 4D8 | 11D6-2B10 / 4D8 |
| HUAD | 9/14/2006 | | 1.6 | | +/- | - | - | - | - |
| | 9/15/2006 | | 4.5 | | + | +/- | + | - | - |
| | 9/16/2006 | | 8.7 | | + | + | + | - | - |
| | 9/17/2006 | | N/A | | | | | | |
| | 9/18/2006 | | N/A | | | | | | |
| | 9/19/2006 | | 3.3 | | - | - | - | - | - |
| | 9/20/2006 | | 3 | | - | - | - | - | - |
| | 9/21/2006 | | 1 | | - | - | - | - | - |

FIG. 36

3 MINUTE VISUAL READ

| | |
|---|---|
| + | POSITIVE |
| +/- | AMBIGUOUS |
| - | NEGATIVE |

HYPERGLYCOSYLATED HCG DETECTION DEVICE

FIELD OF THE INVENTION

The present invention is related to devices that can selectively detect hyperglycosylated human chorionic gonadotropin (hCG-H) for detecting pregnancy in a woman. Another aspect of the present invention relates to a method of evaluating the viability of a pregnancy.

BACKGROUND OF THE INVENTION

Human chorionic gonadotropin (hCG) is a glycoprotein produced by the placenta soon after fertilization. This hormone has the crucial role of maintaining steroid production by the corpus luteum in early pregnancy, and ensures that pregnancy progresses unabated. Thus, the detection of hCG has been utilized as a marker for pregnancy in women. Accordingly, measurement of hCG in blood or urine has been the basis of prior and current pregnancy tests or devices.

hCG

More specifically, the hCG hormone is a member of the glycoprotein hormone family (GPH) that includes luteinizing hormone (LH), follicle stimulating hormone (FSH), and thyroid stimulating hormone (TSH). All members of the GPH family are heterodimers that consist of an alpha and beta subunit. The alpha subunit is conserved across the GPHs, while the beta subunit is unique. However, there remains about 80% homology across the beta subunits. In addition to conferring differentiation, the beta subunit also grants each heterodimer its unique biological activity and receptor specificity (Pierce and Parsons, 1981; Stenman et al., 2006).

hCG has a molecular weight of around 37 kDa. About one-third of this mass is due to glycosylation consisting of 8 oligosaccharide chains covalently bound to the alpha and beta subunits (Pierce and Parsons, 1981). It is produced by the syncytiotrophoblast cells following fertilization and its primary function is to maintain the production of progesterone by the corpus luteum in early pregnancy (Hoshina et al., 1985; Lustbader et al., 1998). During excretion, intact hCG can be partially degraded into its component subunits allowing different variants of hCG to be detected in liquid samples, such as urine.

As is well known, the association of hCG and pregnancy was first reported in 1927. During the 1960's, the advent of immunoassays allowed the direct detection of hCG in pregnancy urine (Wide and Gemzell, 1960; Vaitukaitis et al., 1972). A variety of different hCG isoforms or fragments are present in both serum and urine. Intact hCG has been discovered to be the predominant form of hCG and have the most biological relevance throughout all stages of pregnancy despite the presence of the other isoforms detected include free hCG alpha subunit, free hCG beta subunit, hCG beta core fragment, nicked hCG, and hyperglycosylated hCG (hCG-H) (O'Connor et al., 1994; McChesney et al., 2005).

hCG-H

Although intact hCG is the most prevalent form of the molecule found throughout pregnancy, other distinct isoforms have emerged with different biological activities. One such form, hyperglycosylated hCG (hCG-H), differs from regular hCG in the amount of and/or location of oligosaccharide chains present on the beta subunit of hCG. This different glycosylation pattern is believed to alter the function of the molecule such that hCG-H provides a role in promoting implantation of a developing zygote.

Whereas hCG production is typically considered to be limited to pregnancy, it has also been found to be produced in certain types of invasive cancer associated with gestational trophoblastic disease (Cole et al., 2006). These tumors (hytatidiform mole, choriocarcinoma, and placental site trophoblastic tumors) are both aggressive and malignant, and a key marker for their presence is the production of hCG (particularly the beta subunit of hCG) in the absence of pregnancy (Cole et al., 2003). Research into hCG produced by choriocarcinoma tumor cells identified that there were significant weight differences in hCG derived from choriocarcinoma when compared to hCG present in pregnancy (~40 kDa compared to ~37 kDa) (Hussa, 1977; Mizuochi et al., 1983; Amano et al., 1988). Further studies on the choriocarcinoma derived hCG elucidated that the weight differences were due to excess glycosylation leading to significantly larger oligosaccharides on the beta subunit (Elliott et al., 1997). The term hyperglycosylated hCG, or hCG-H, was coined for this higher molecular weight choriocarcinoma derived hCG containing invasive properties, with regular hCG reserved for the hCG with normal oligosaccharide chains found during pregnancy (Elliott et al., 1997; Cole et al., 1998).

Previously researchers developed an hCG-H monoclonal antibody by immunizing mice with hCG-H produced by a single patient with choriocarcinoma. This antibody, B152, specifically recognized choriocarcinoma derived hCG-H in both serum and urine. This allowed researchers to more effectively screen and monitor the presence of hCG-H. Subsequent studies utilizing the B152 antibody found that hCG-H is not only produced by choriocarcinoma, but it is also found in very early pregnancy as well (O'Connor et al., 1998), and that hCG-H is the predominant form of hCG produced by cytotrophoblast cells at the time of trophoblast invasion irrespective if the invasion is associated with choriocarcinoma or pregnancy (Kovalevskaya et al., 2002). Cytotrophoblast cells differ from those that produce regular hCG (syncytiotrophoblast cells), and they confer a different function to hCG-H that is closely linked with the implantation of the zygote into the uterine lining after conception (Kovalevskaya et al., 2002). Studies have also shown that hCG-H cannot replace the corpus luteum stimulating activity of regular hCG which suggests a distinct biological activity for hCG-H separate from that of pregnancy promoting function of regular hCG (Cole et al., 1991).

Early pregnancy derived hCG-H has the same molecular weight as choriocarcinoma derived hCG-H (Kovalesyskaya et al., 2002), and the majority of all hCG immunoreactivity in serum and urine samples from early pregnancy is due to the presence of hCG-H (O'Connor et al., 1998; Cole et al., 1999; Butler et al., 2002; Cole et al., 2003; Sutton-Riley et al., 2006). Further, hCG-H accounts for >90% of all hCG at the time of implantation (Cole et al., 2003). This proportion of hCG-H steadily decreases as pregnancy progresses until it only accounts for about 2% of all hCG by the $2^{nd}$ and $3^{rd}$ trimesters.

Early Pregnancy Loss

There is a correlation between low or absent levels of hCG-H in early pregnancy, and early pregnancy loss. In light of research implicating that hCG-H plays a key role in trophoblast invasion, many have suggested that the high incidence of early pregnancy loss in the absence of hCG-H is due to ineffective implantation of the zygote in the uterine lining Some studies have estimated that only 30% of all fertilized eggs continue to term to result in a live birth (Zinaman et al., 1996; Slama et al., 2002). Over the years a subset of these unsuccessful pregnancies that result from a failed implantation have been given names such as 'occult pregnancies', 'preclinical pregnancies', 'biochemical pregnancies', and 'early pregnancy loss' (Macklon et al., 2002). They all serve to describe a phenomenon whereby the conceptus is unable to successfully implant and therefore pregnancy does not progress past the first few weeks after conception. The incidence of early pregnancy loss due to failed implantation has been estimated to be about 30% of all conceptions, making it a significant occurrence in fertile individuals attempting to conceive (Wilcox et al., 1988; Macklon et al., 2002).

Fertilization of the egg typically occurs in the fallopian tube approximately 24-48 hours after ovulation. The fertilized egg (now termed a zygote) continually divides as it travels through the fallopian tube. However, its survival is not ensured until it enters the uterine cavity and implants into the uterine lining. Implantation typically occurs from about 7 to about 10 days after fertilization and is the result of several complex molecular interactions that allow the developing blastocyst to embed in the lining and eventually establish contact with nutrient enriched maternal blood (Carson et al., 2000; Enders, 2000; Norwitz et al., 2001). hCG-H has been identified as a marker whose presence (or absence) can serve to indicate if this successful implantation in the uterine lining has occurred (Cole and Khanlian, 2007).

For instance, many studies have found that an unduly low proportion (or absence) of hCG-H in early pregnancy is associated with early pregnancy losses prior to the $6^{th}$ week of gestation (O'Connor et al., 1998; Kovalevskaya et al., 2002; Sutton-Riley et al., 2006). Sasaki et al. (2007) recently found that in 62 successful conceptions, only those that had an hCG-H proportion greater than 50% in the first week following conception continued to term. As such, low proportions of hCG-H around the time of implantation may destine pregnancy for failure due to an unsuccessful implantation. Such studies, taken together with the abundance of choriocarcinoma data associating hCG-H with trophoblast invasion, suggest that hCG-H has an essential role in promoting the invasive properties of the conceptus resulting in successful implantation (Lei et al., 1999; Cole et al., 2007). In the absence of the implantation promoting ability of hCG-H, the conceptus may not achieve successful implantation and ultimately result in an early pregnancy loss (Kovalevskaya et al., 2007; Cole, 2007).

hCG-H and Pregnancy Testing

Traditional pregnancy tests in both the point of care (POC) and over the counter (OTC) markets are developed to detect regular or total hCG. Although both regular hCG and hCG-H can be used to measure pregnancy, they are not equal in the results that are conveyed to the consumer (Cole et al., 2007). As up to 30% of all conceptions result in early pregnancy loss (Wilcox et al., 1988), by assaying for regular hCG alone, these non-viable pregnancies are being detected and conveyed to the consumer as a successful pregnancy. As such, regular hCG can be considered a poor discriminator of pregnancies that may ultimately result in early pregnancy loss. The overwhelming majority of currently available POC and OTC pregnancy tests poorly detect hCG-H, with only a handful of tests displaying equal sensitivity to both regular hCG and hCG-H (Butler et al., 2001; Cole et al., 2003; Cole et al., 2004).

Another shortcoming of traditional pregnancy tests is readily realized upon consideration of women who are attempting to conceive through fertility treatments. Such women are typically administered regular hCG to mimic an LH surge and promote ovulation from mature ovarian follicles. This exogenous hCG is gradually cleared from their system over a period of about 10 days (Stenman et al., 1997), but it precludes these women from taking a traditional pregnancy test as it would result in them achieving a 'false positive' due to lingering exogenous hCG in their system. If these individuals were to use a pregnancy test specific for hCG-H, the exogenous regular hCG in their system would likely have no bearing on the results conveyed through the test.

Currently, there is no OTC device available that can specifically detect hCG-H. However, there is an automated chemiluminescent hCG-H assay based on the B152 antibody (Nichols Advantage immunoassay) which has been cleared by the FDA for use in pregnancy related applications (Pandain et al., 2003; Weinans et al., 2005). While it is specific for hCG-H, this test requires a long sample incubation time of about 4 hours. Thus, this test must be run in a laboratory setting in order to achieve results (Cole et al., 2004). As many doctors advise women who achieve a positive pregnancy test result at home to wait for at least 6 weeks prior to scheduling a visit, the use of the laboratory based assay to detect hCG-H is not practical as those with unsuccessful implantation related to a low prevalence of hCG-H may have already suffered an early pregnancy loss prior to the doctor's visit. The development of an at home hCG-H based pregnancy test would rapidly convey to the consumer that not only are they pregnant, but that their odds for early pregnancy loss resulting from failed implantation are significantly reduced.

There remains a need for both POC and OTC pregnancy test devices that can selectively or preferentially detect hCG-H. There also remains a need for a pregnancy test device exhibiting an improved level of accuracy for determining the viability of a pregnancy.

BRIEF SUMMARY OF THE INVENTION

The present invention satisfies at least some of the aforementioned needs by providing pregnancy devices that can selectively or preferentially detect hyperglycosylated human chorionic gonadotropin (hCG-H). Embodiments of the present invention include a device for selectively or preferentially detecting hyperglycosylated human chorionic gonadotropin (hCG-H) in a liquid sample deposited on a proximal portion of the device for transport to a distal portion of the device. This particular device includes a release medium formed of a first material having a detectable label thereon and a capture medium in fluid communication with the release medium and formed of a second, different material. The capture medium includes a capture site. At least one of the release medium and the capture medium includes a binding member that exhibits a moderate to high affinity for hCG-H and is selectively or preferentially reactive with hCG-H. Devices according to embodiments of the present invention can provide confirmation of the viability of a pregnancy as only fertilized eggs with a high likelihood of successful implantation (i.e. those with an appropriate level of hCG-H) can be detected by the assay.

In other embodiments, the invention comprises a device for selectively or preferentially detecting hyperglycosylated human chorionic gonadotropin (hCG-H), in which the device includes a release medium formed of a first material and having a detectable label thereon. The device also includes a capture medium in fluid communication with the release medium and formed of a second, different material. The capture medium includes a capture site. Devices according to this particular embodiment include a scavenger component that is selectively or preferentially reactive with regular hCG. The scavenger component can be located between the location of sample deposit and the capture site. Further, at least one of the release medium and the capture medium can include a binding member that is reactive with hCG-H. In a preferred embodiment the binding member can be selectively or preferentially reactive with hCG-H and also exhibit a moderate to high affinity for hCG-H.

In certain embodiments, the device for selectively or preferentially detecting hCG-H in a liquid sample deposited on a proximal portion of the device for transport to a distal portion of the device includes a release medium formed of a first material and having a detectable label and a capture medium in fluid communication with the release medium and formed of a second, different material. The capture medium includes a capture site. Additionally, such devices include a mixture of binding members. In these embodiments, the mixture of binding members includes a first group of binding members that are selectively or preferentially reactive with an epitope of regular hCG and a second group of binding members that exhibit a moderate to high affinity for hCG-H and are selectively or preferentially reactive with an epitope of hCG-H. In one such embodiment, the binding members are selectively or preferentially reactive with hCG-H account for greater than 50% of the total number of binding members present in the mixture.

In yet another embodiment, the present invention comprises a device for selectively or preferentially detecting hCG-H in a liquid sample, in which the device includes a release medium formed of a first material and having a detectable label and a capture medium in fluid communication with the release medium. Devices according to such embodiments further include at least one binding member that exhibits a moderate to high affinity for hCG-H and is selectively or preferentially reactive with an epitope of hCG-H and at least one binding member that is reactive with an epitope of regular hCG. The capture medium is preferably formed of a second, different material, and includes a first capture site that directly or indirectly binds hCG-H and a second capture site that directly or indirectly binds regular hCG.

In certain embodiments, the present invention comprises a device for selectively or preferentially detecting hCG-H in a liquid sample, wherein the device includes a common fluid path for receiving and distributing the liquid sample. The device also includes at least one release medium in fluid communication with the common fluid path. The release medium can be formed of a first material and include a detectable label. Devices according to these embodiments can include a first capture medium in fluid communication with the at least one release medium, wherein the capture medium is preferably formed of a second material. The first capture medium includes a capture site that directly or indirectly selectively or preferentially binds hCG-H. Also, devices according to such embodiments can also preferably include a second capture medium in fluid communication with the at least one release medium and formed of the same material as the other capture medium. The second capture medium can include a capture site that directly or indirectly binds regular hCG.

In another aspect, the present invention provides a method of evaluating the viability of a pregnancy. Methods according to embodiments of the present invention include providing a test device for selectively or preferentially detecting hCG-H, as described herein, and applying a liquid sample potentially including one or both of regular hCG and hCG-H to the device. Such methods can also include detecting the presence or lack thereof of hCG-H in the liquid sample. The detected presence of hCG-H indicates a viable pregnancy.

BRIEF DESCRIPTION OF THE SEVERAL VIEWS OF THE DRAWINGS

Figure 1:
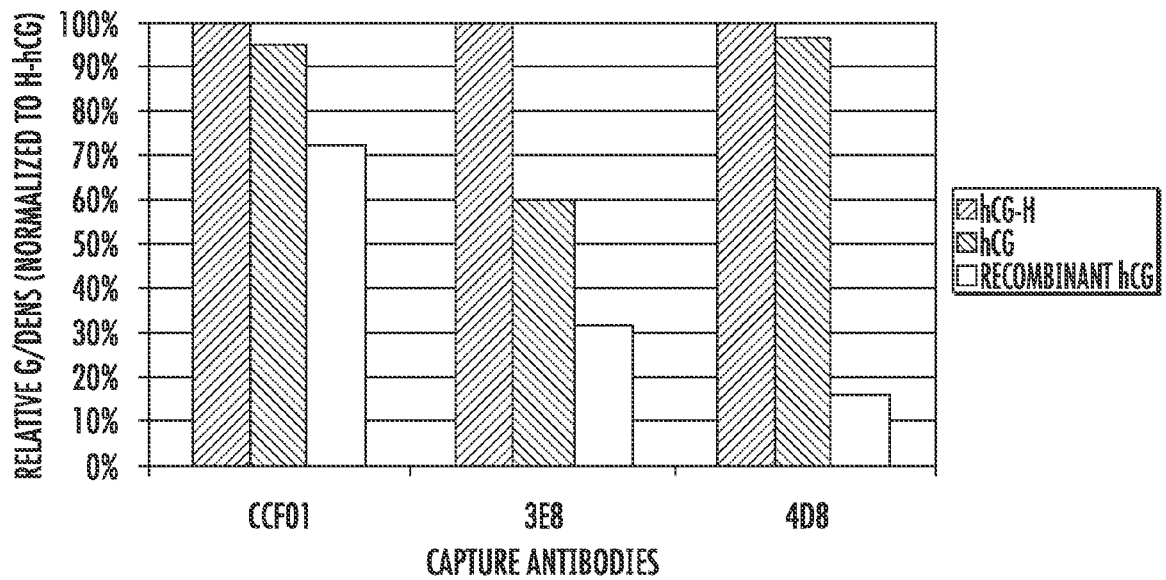
Figure 2A:
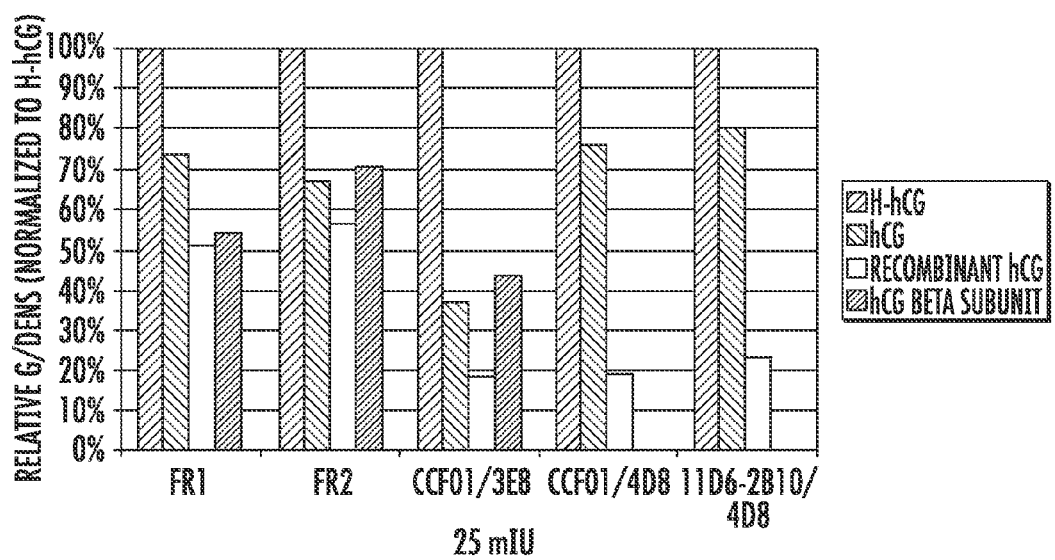
Figure 2B:
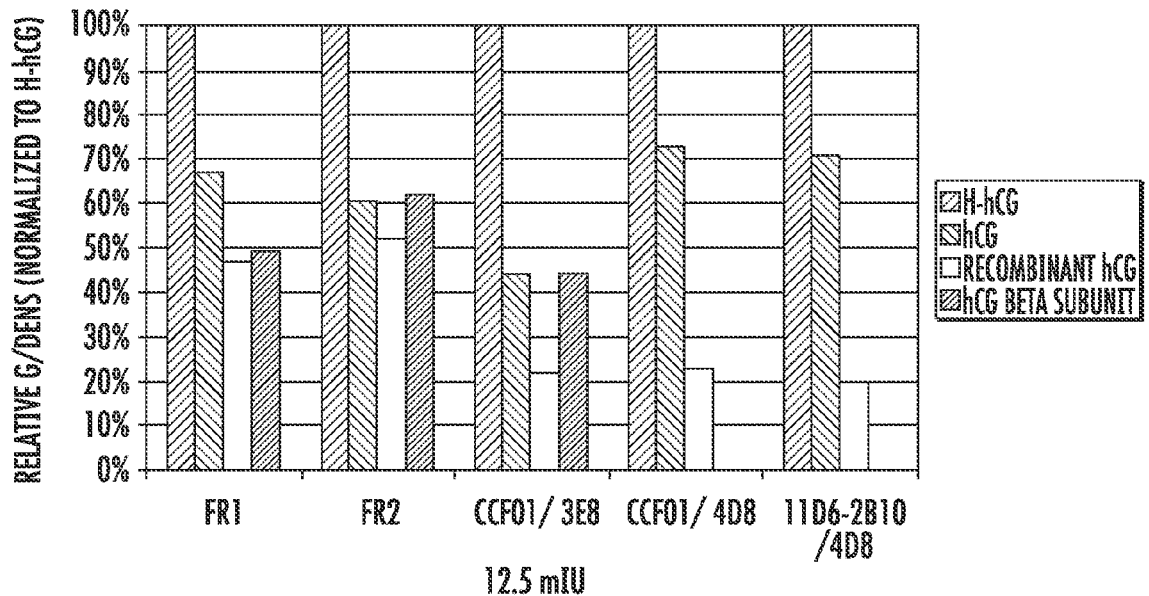
Figure 2C:
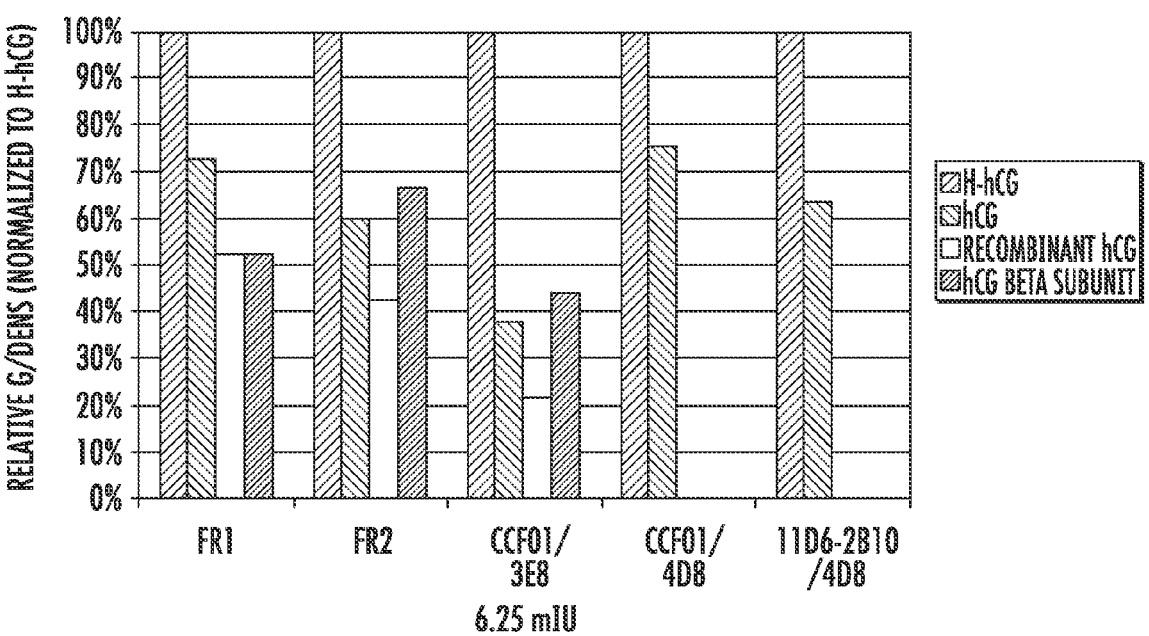
Figure 3A:
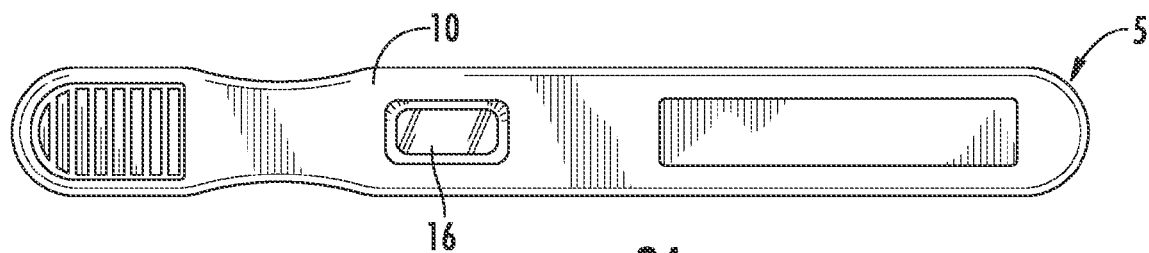
Figure 3B:
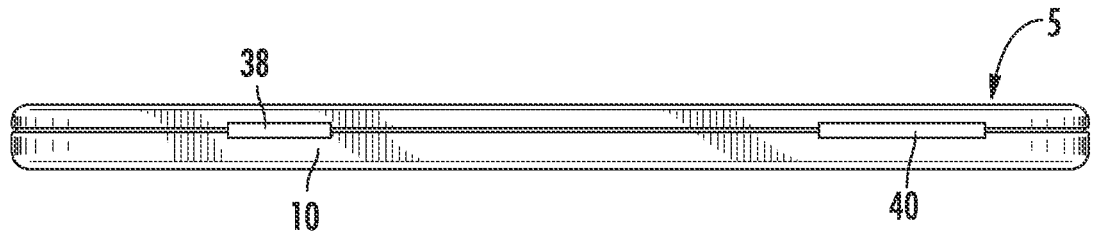
Figure 3C:
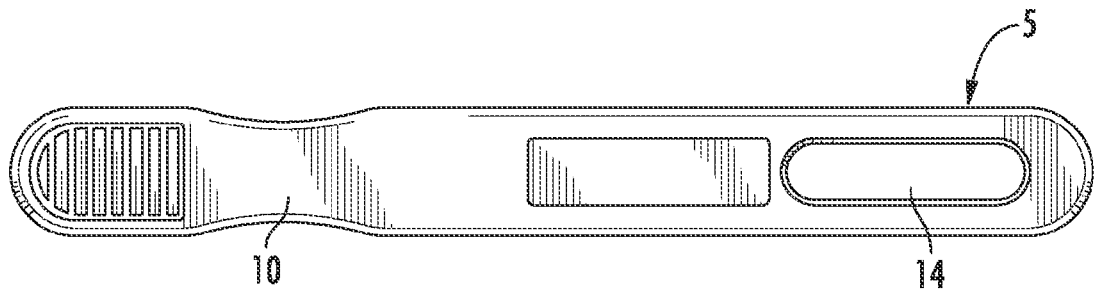
Figure 3D:
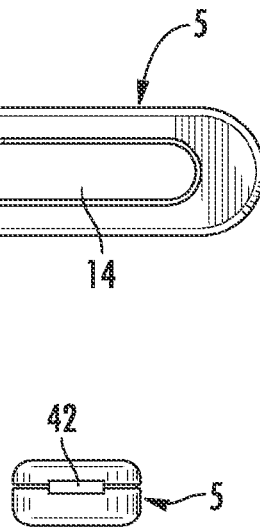
Figure 3E:
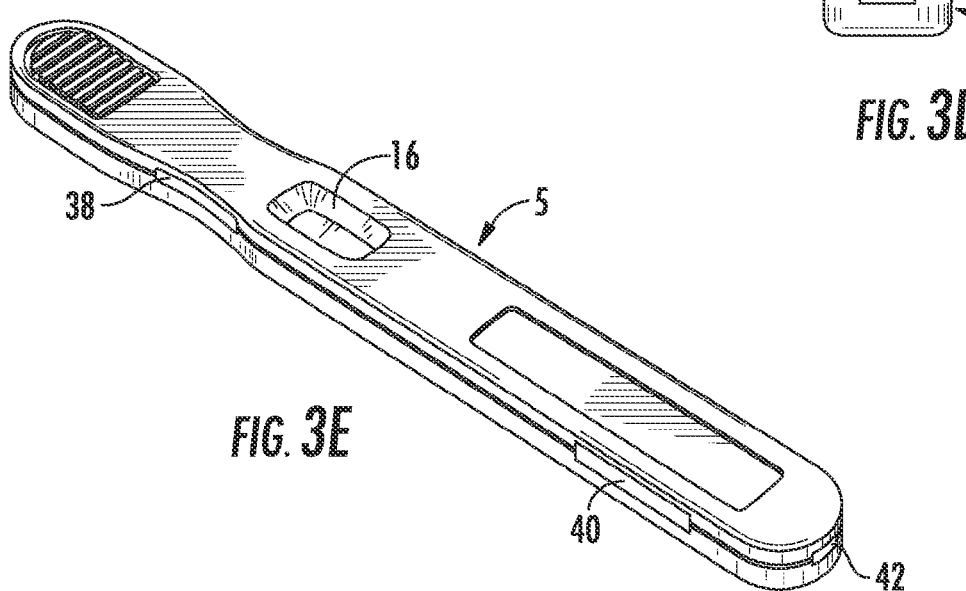
Figure 4A:
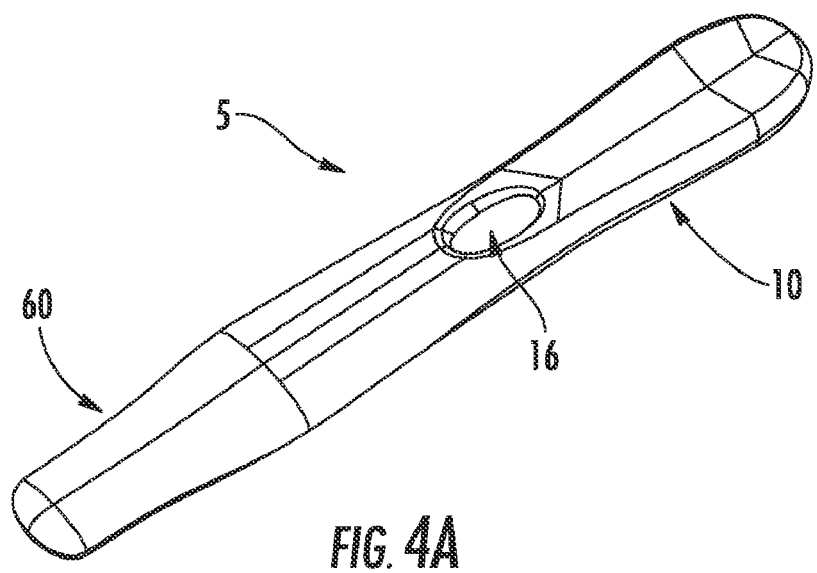
Figure 4B:
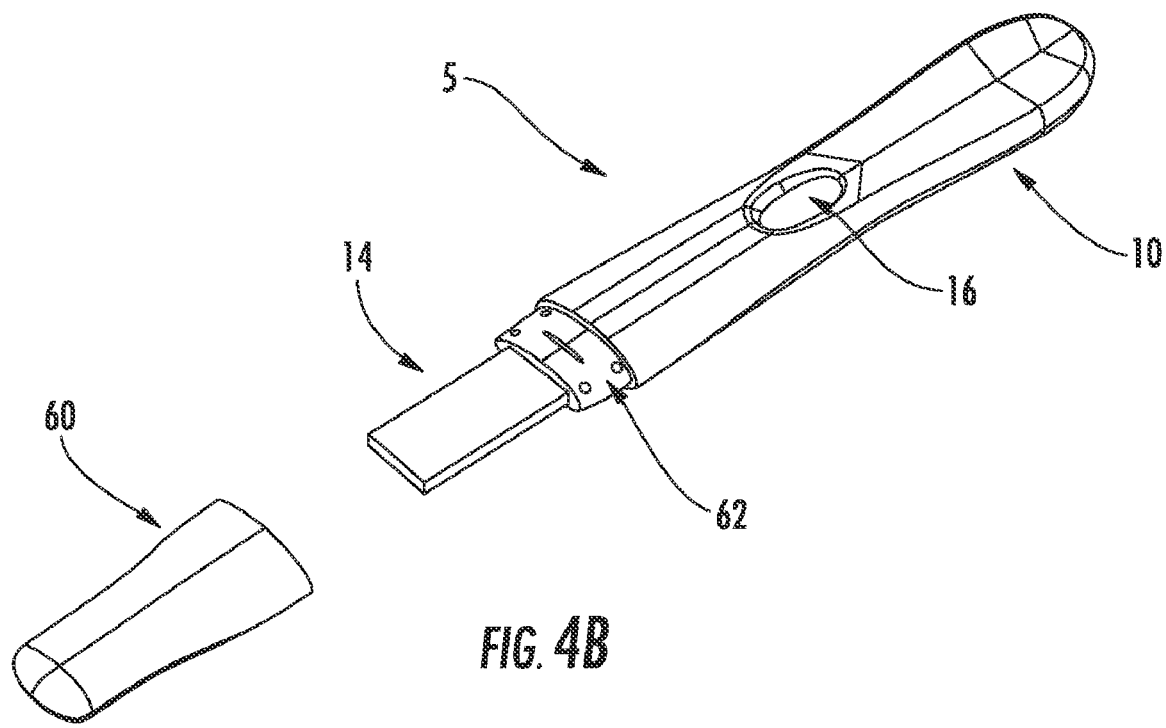
Figure 4C:
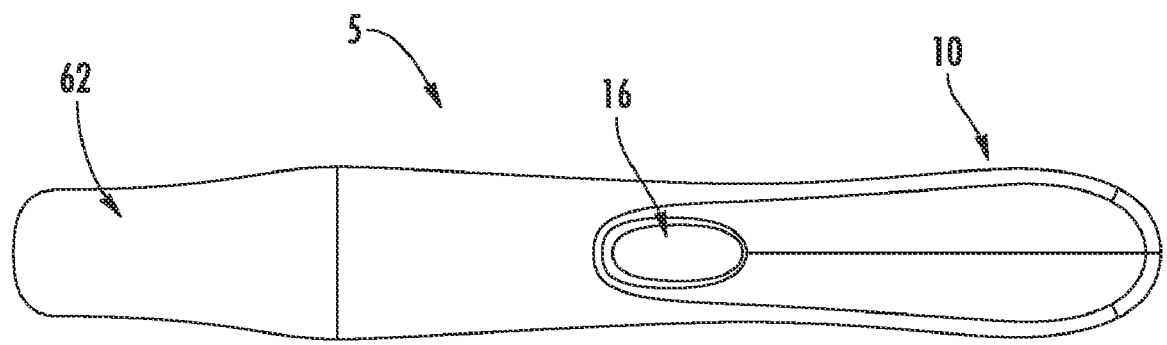

Having thus described the invention in general terms, reference will now be made to the accompanying drawings, which are not necessarily drawn to scale, and wherein:

FIG. 1 illustrates the relative hCG-H discrimination between antibodies in a traditional lateral flow format;

FIG. 2A illustrates the relative hCG-H discrimination between antibodies in an avidin biotin lateral flow format for liquid samples having 25 mIU/ml standards;

FIG. 2B illustrates the relative hCG-H discrimination between antibodies in an avidin biotin lateral flow format for liquid samples having 12.5 mIU/ml standards;

FIG. 2C illustrates the relative hCG-H discrimination between antibodies in an avidin biotin lateral flow format for liquid samples having 6.25 mIU/ml standards;

FIG. 3A depicts a top view of one embodiment of a test device according to the present invention;

FIG. 3B depicts a longitudinal side view of an embodiment of a test device according to the present invention;

FIG. 3C depicts a bottom view of an embodiment of a test device according to the present invention;

FIG. 3D depicts a tail end view of an embodiment of a test device according to the present invention FIG. 3E depicts a top perspective view an embodiment of a test device according to the present invention;

FIG. 4A depicts a front, top, left side perspective view of a preferred embodiment of a test device according to the present invention;

FIG. 4B depicts the test device according to the embodiment from FIG. 4A with the cap thereof removed;

FIG. 4C depicts a top plan view of the test device embodiment from FIG. 4A

Figure 4D:
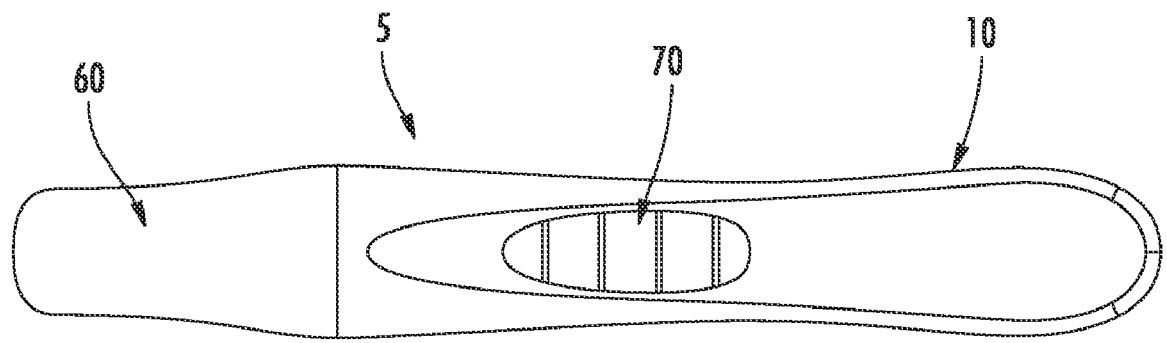

FIG. 4D depicts a bottom plan view of the test device embodiment from FIG. 4A

Figure 4E:
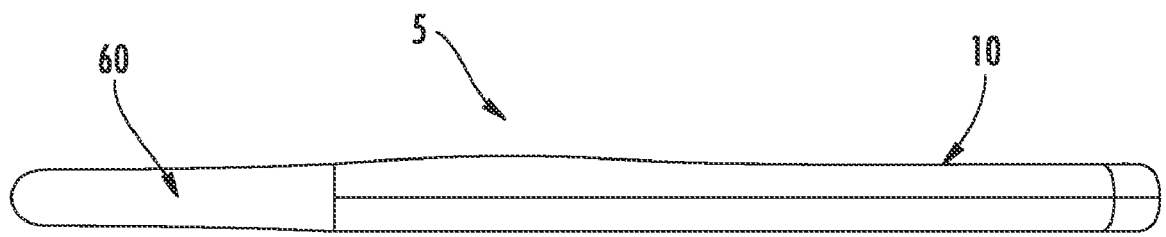
Figure 7:
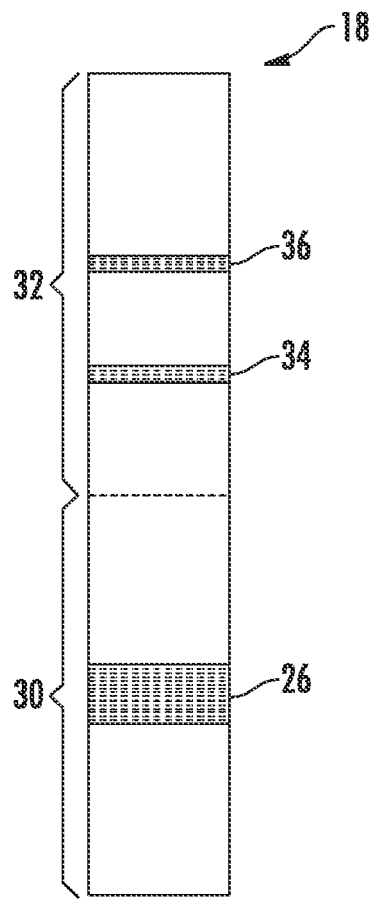
Figure 8:
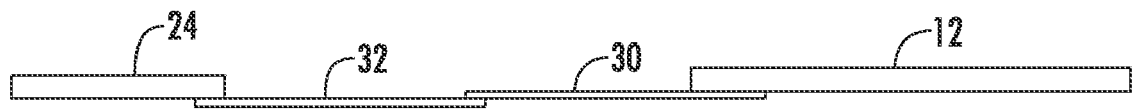
Figure 9:
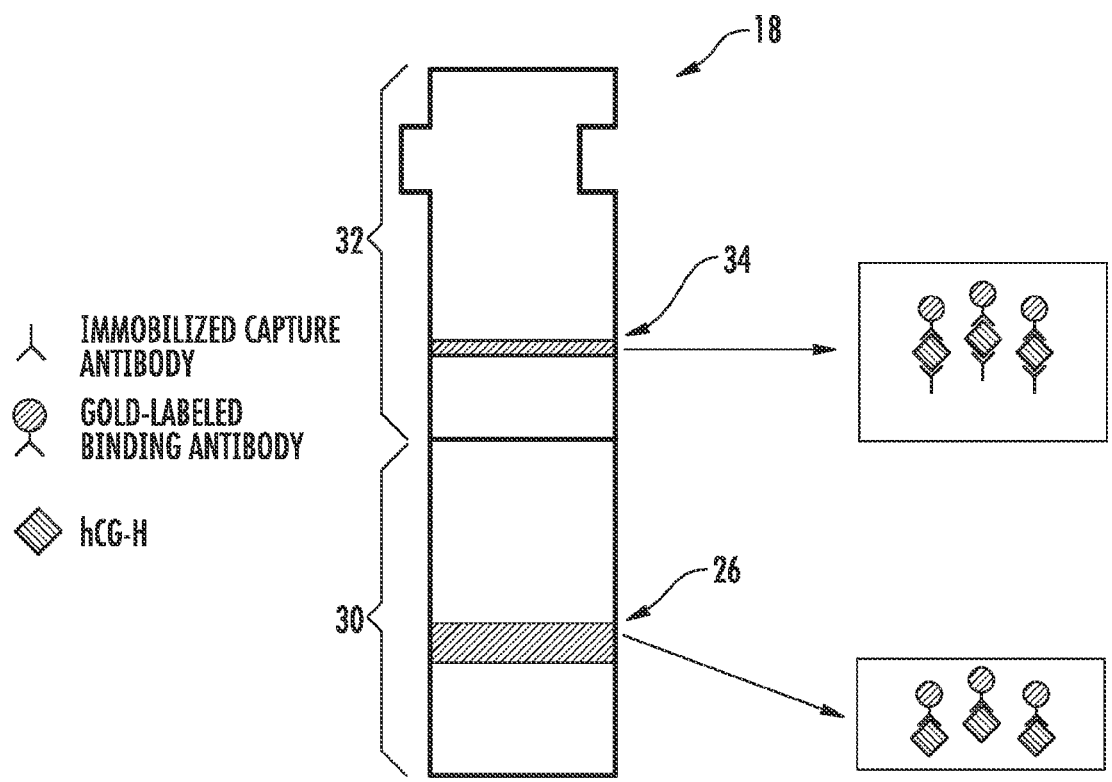
Figure 10:
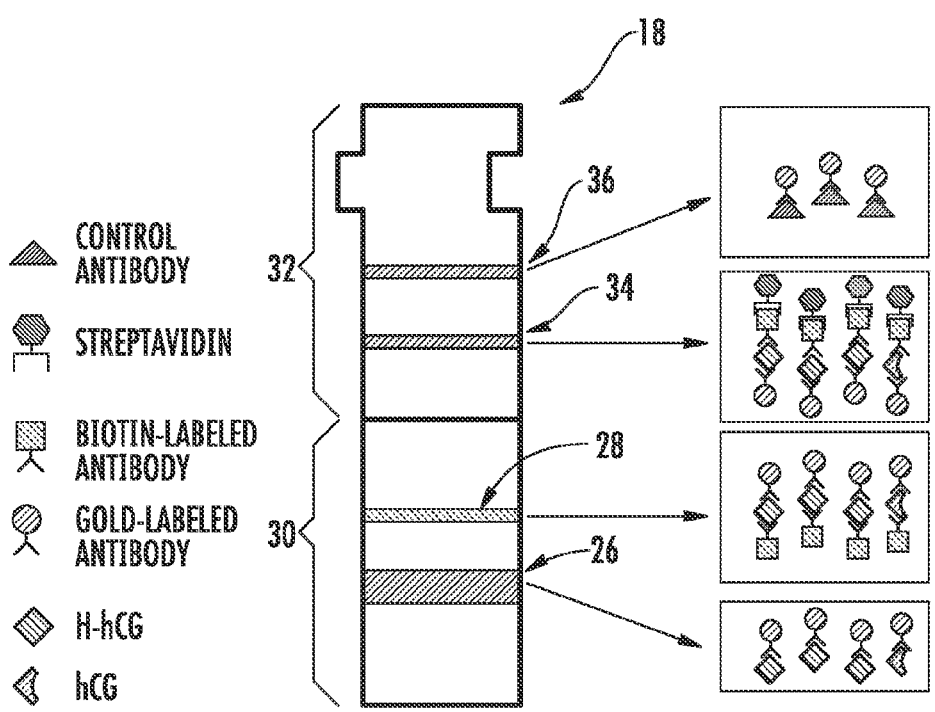
Figure 11:
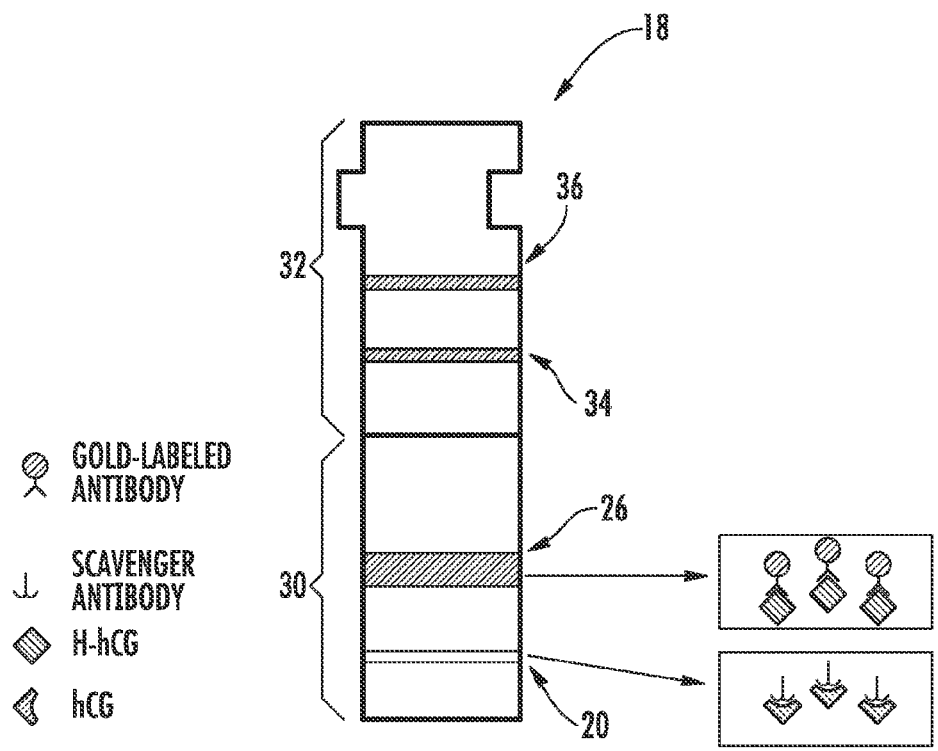
Figure 12:
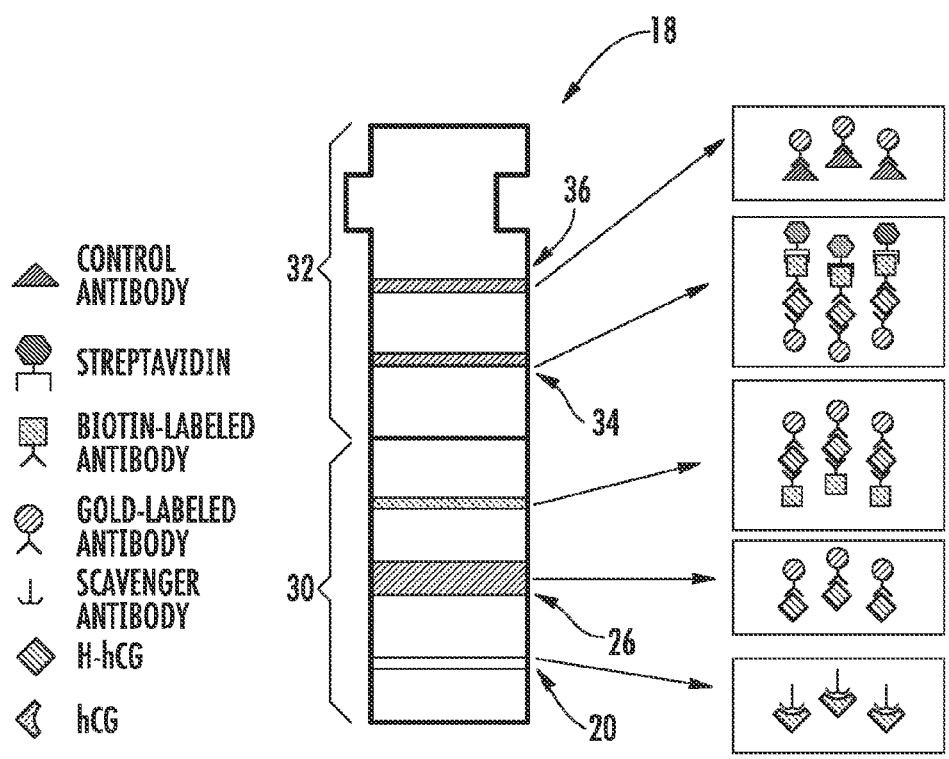
Figure 15:
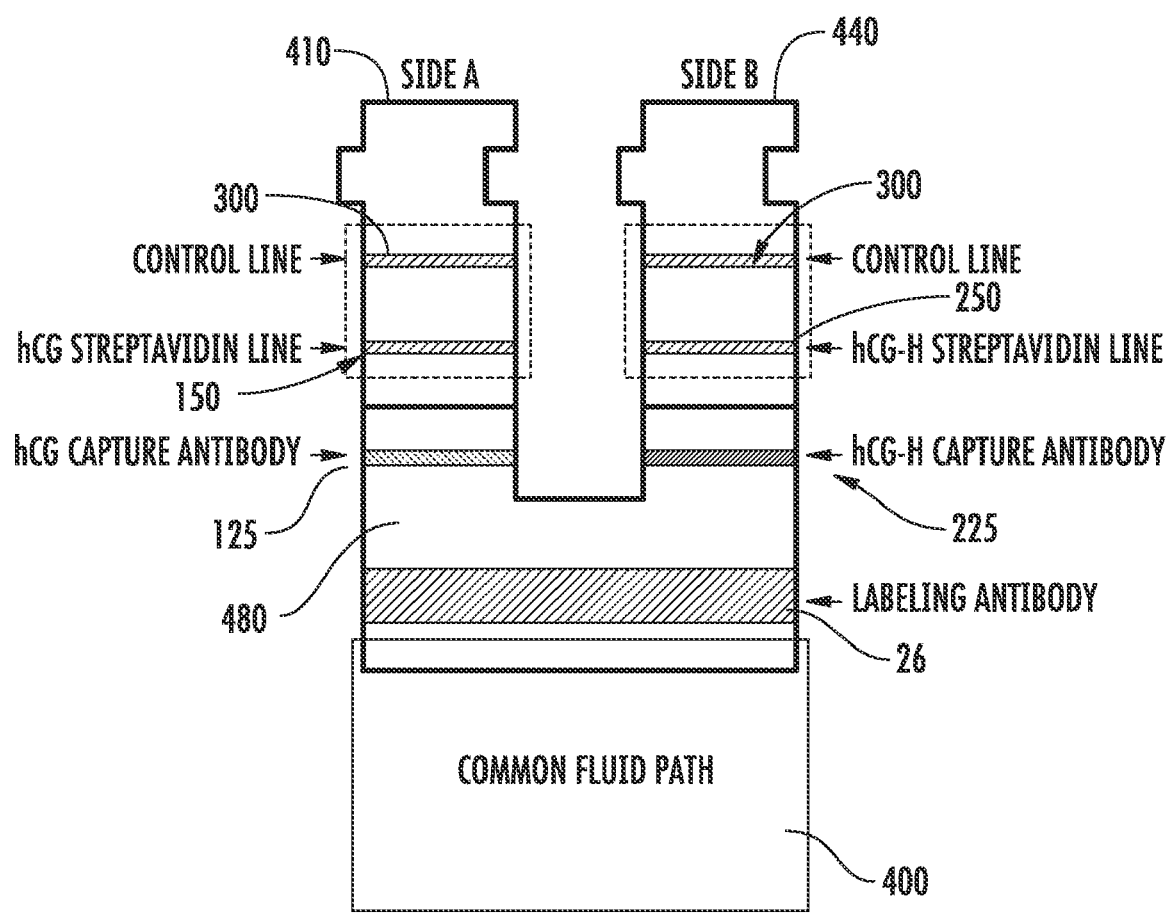
Figures 18, 19:
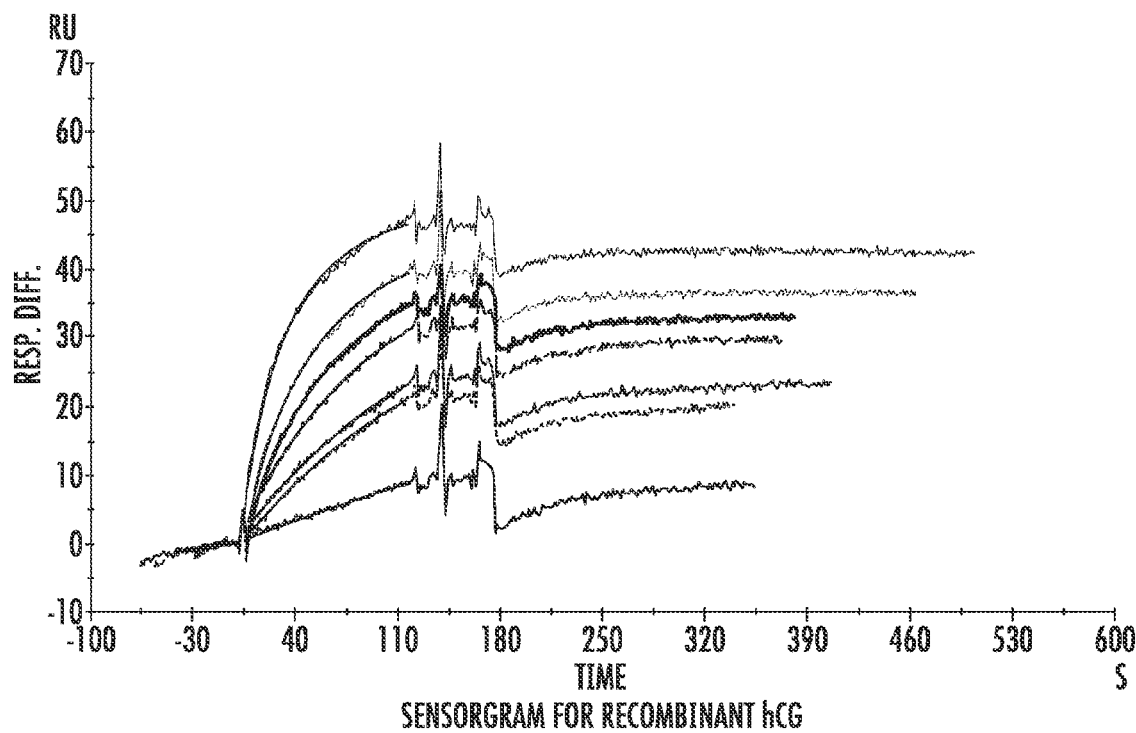
Figure 20:
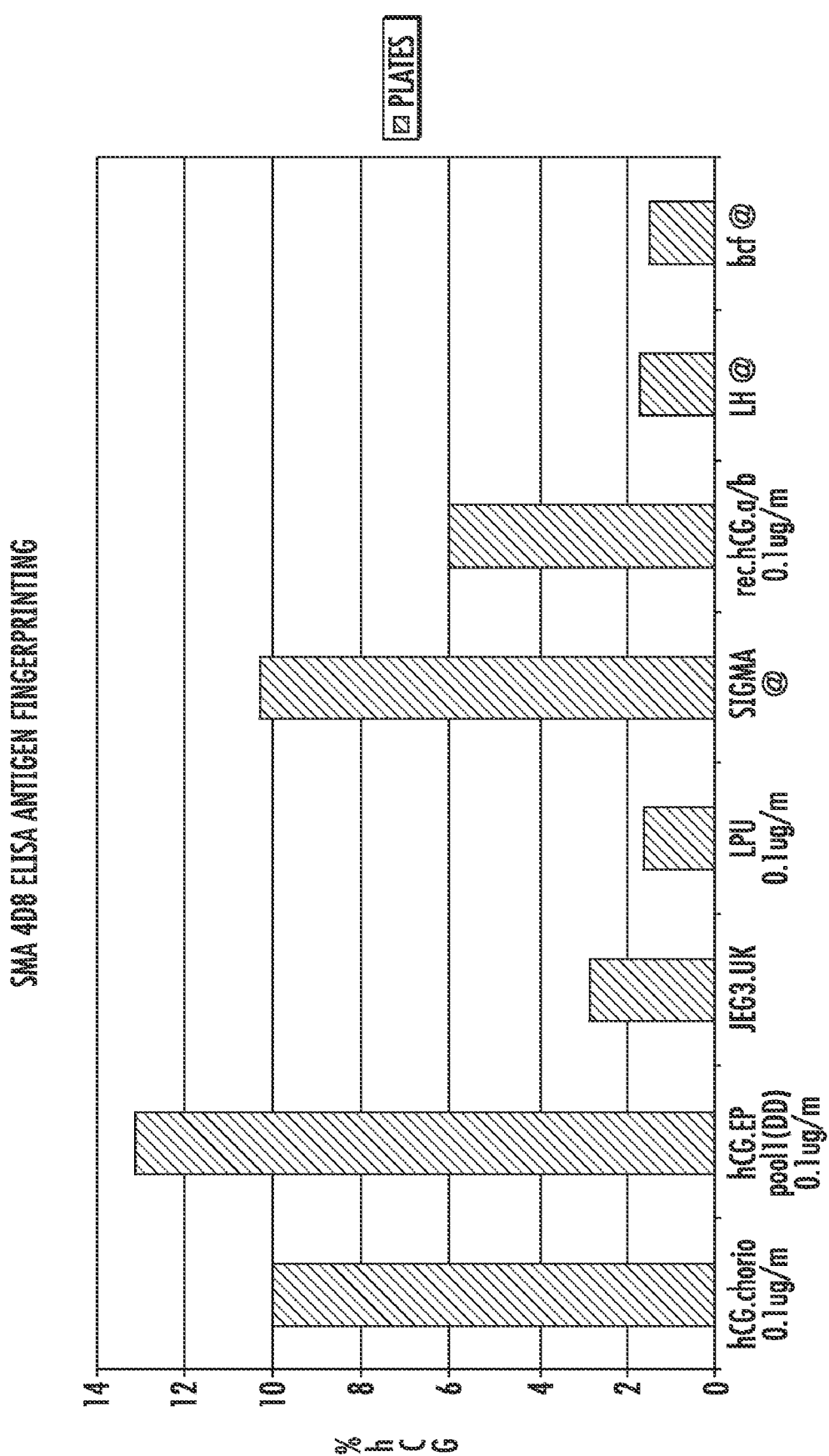
Figure 21:
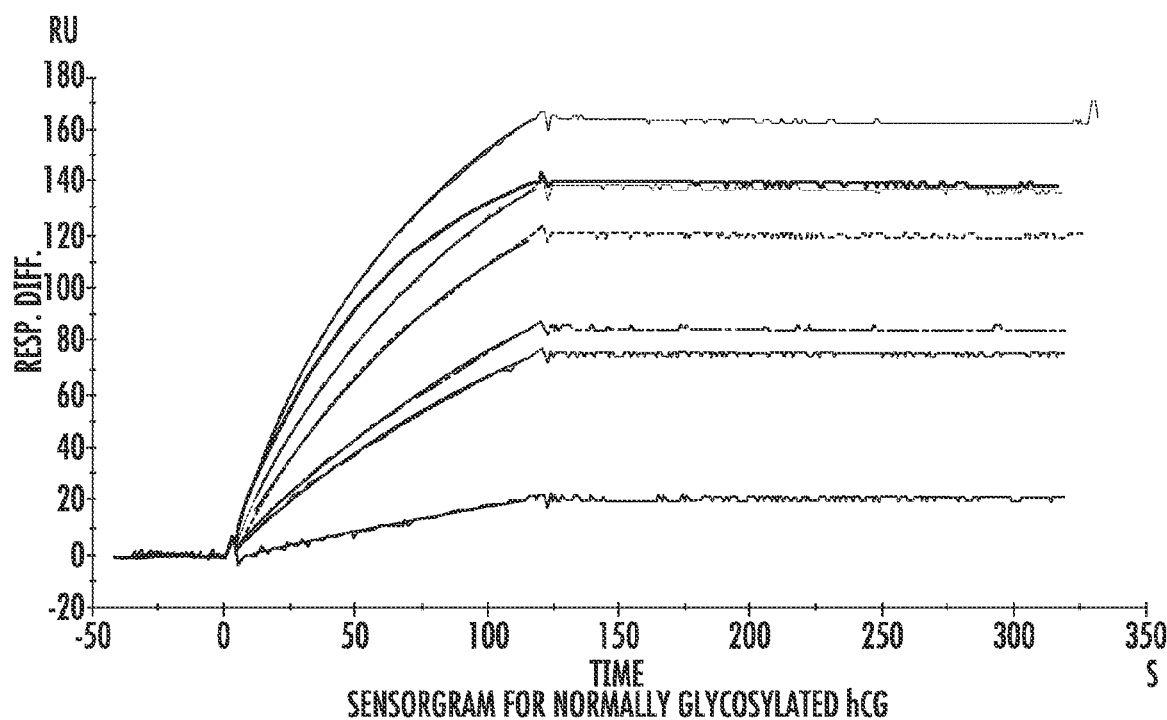
Figure 22:
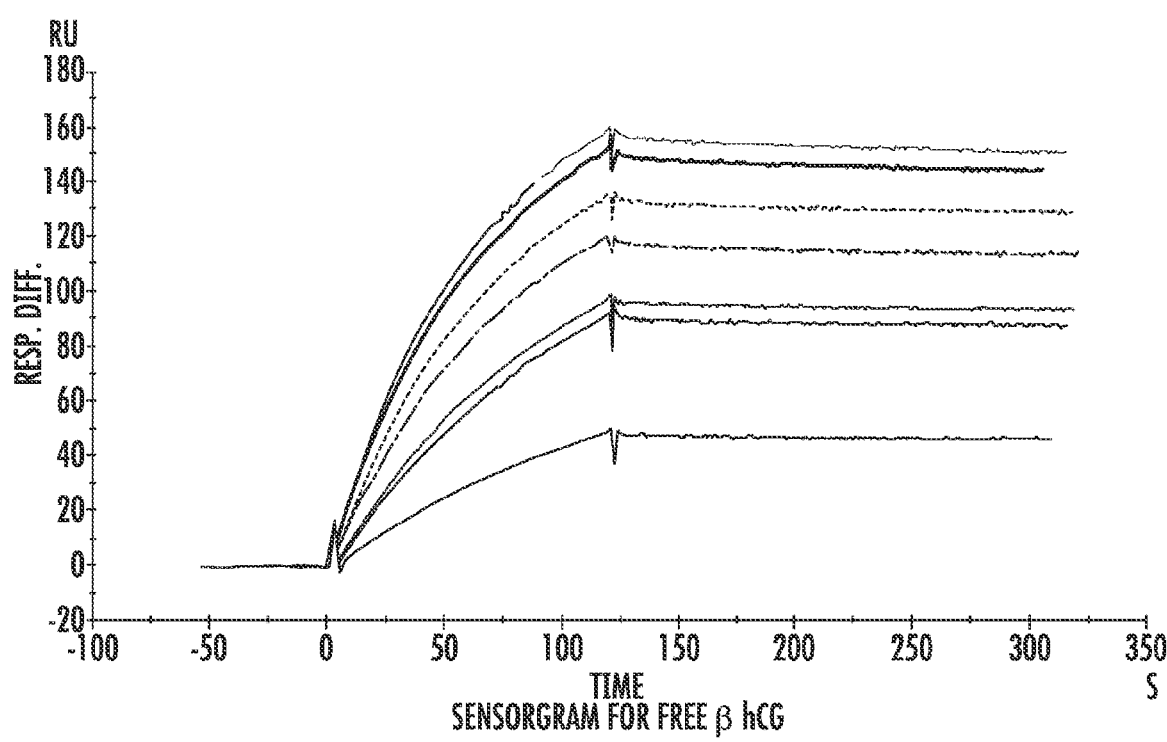
Figure 23:
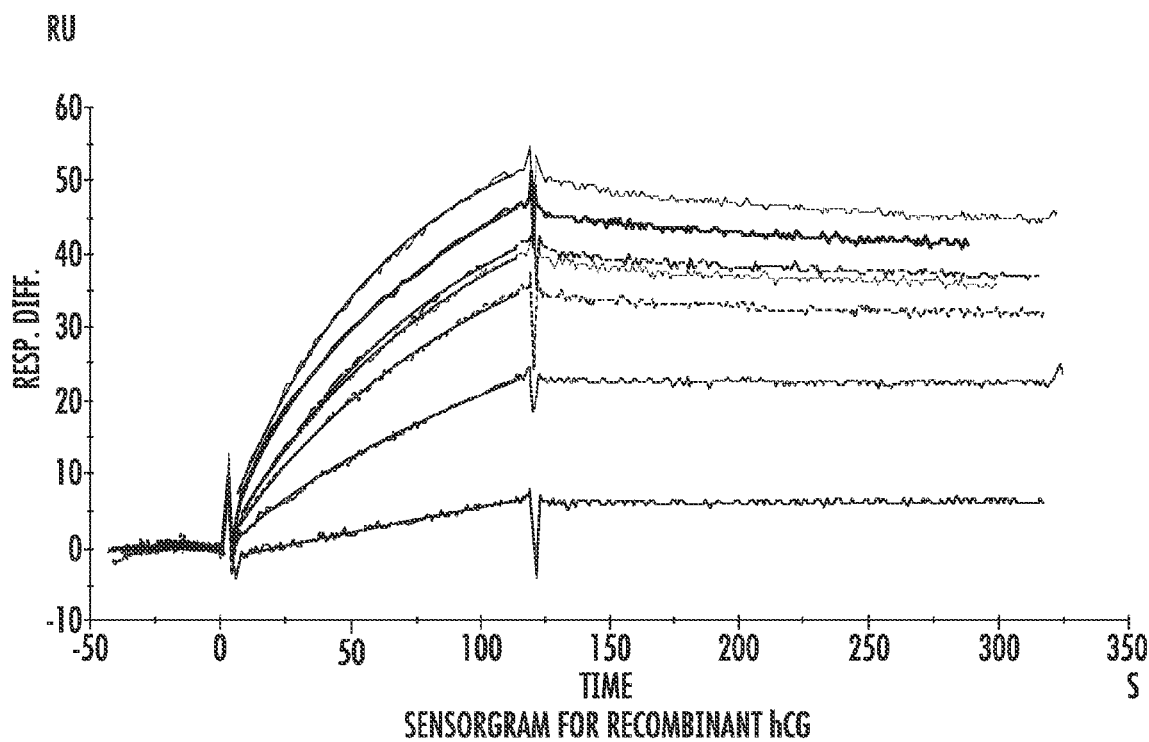
Figure 24:
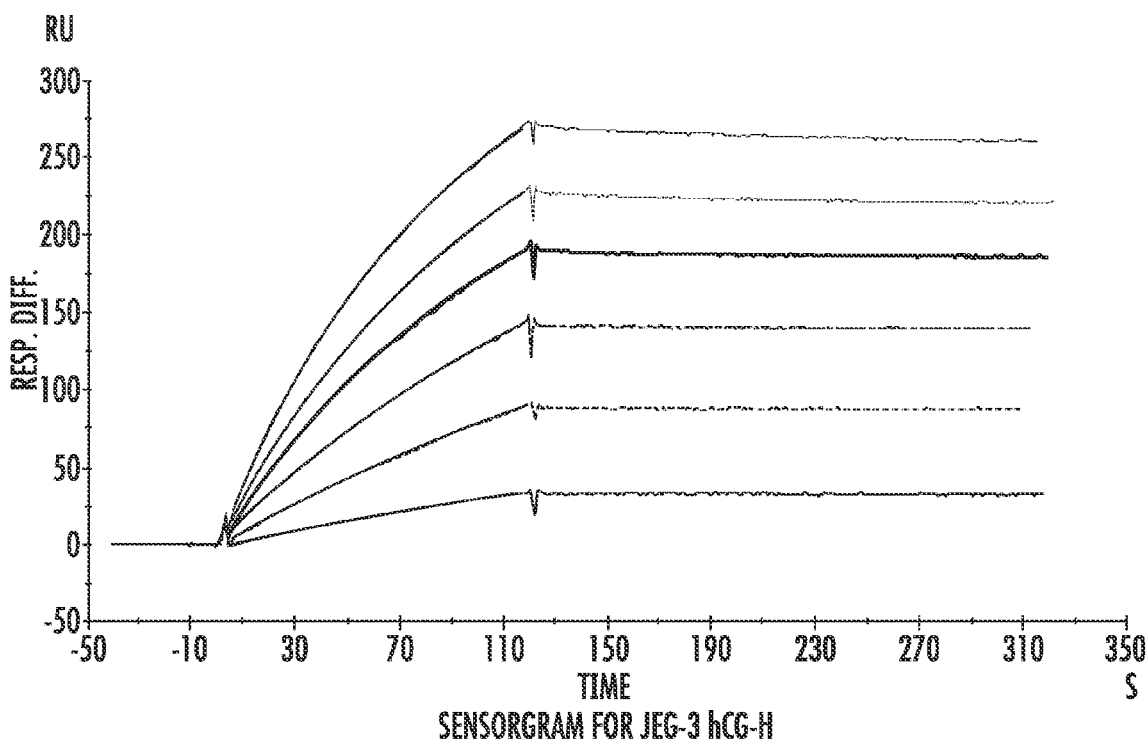
Figure 25:
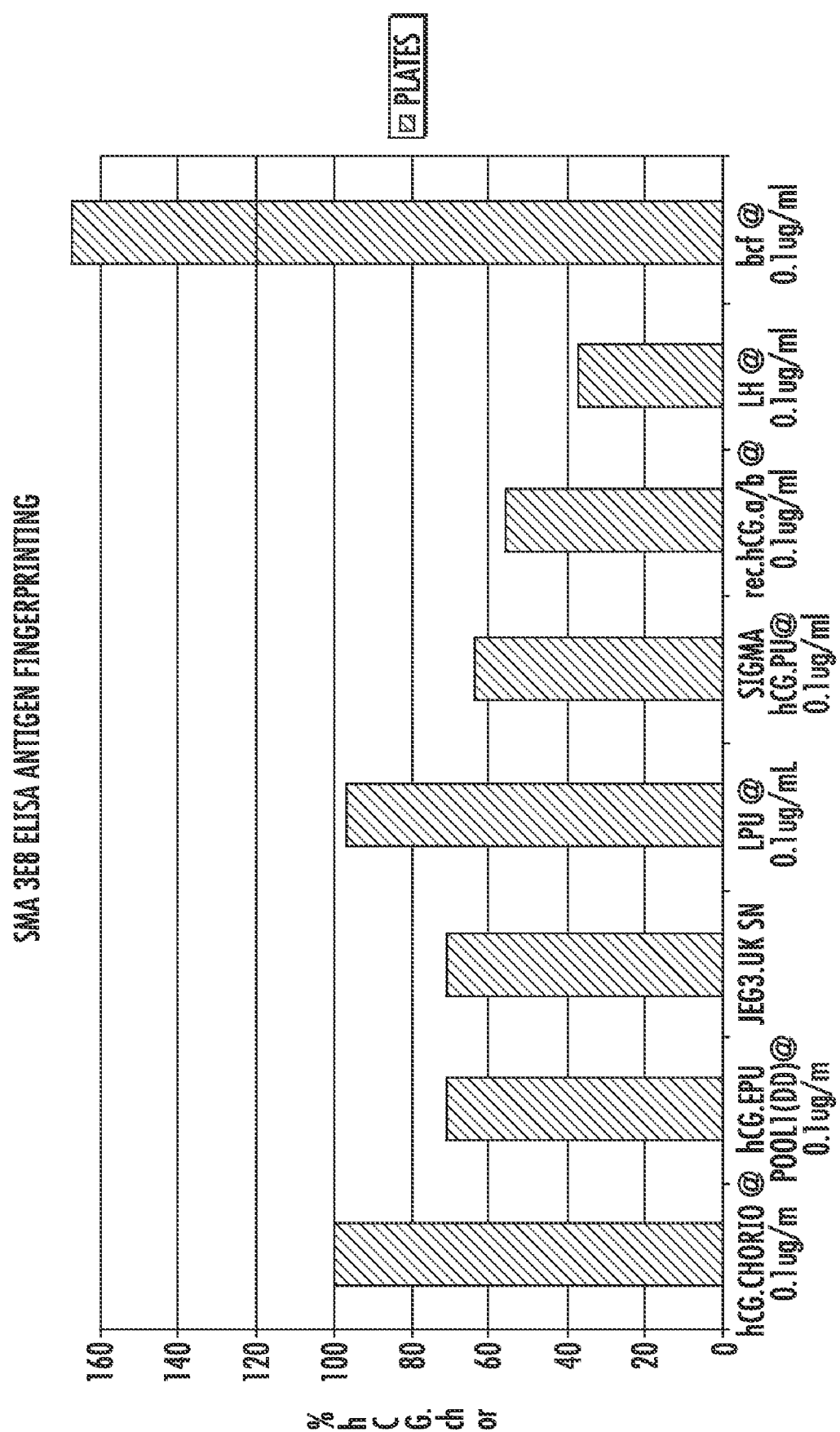
Figure 30:
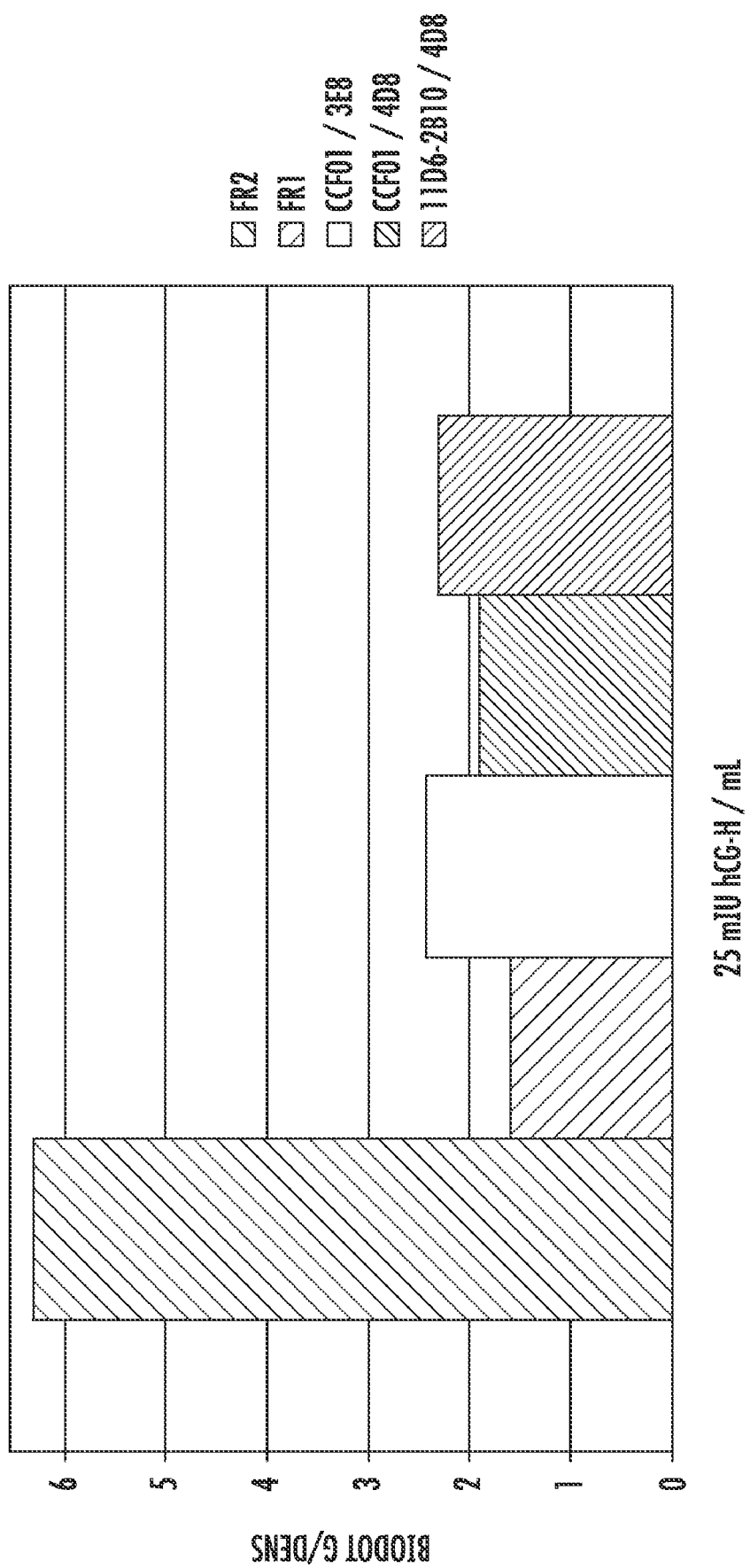

FIG. 4E depicts a left side elevational view of the test device embodiment from FIG. 4A FIG. 5 depicts a schematic top view of a biphasic substrate including a sample collector and upstream absorbent according to one embodiment of the invention;

FIG. 6 depicts a schematic top view of a biphasic substrate according to one embodiment of the invention;

FIG. 7 depicts a schematic top view of a biphasic substrate according to another embodiment of the invention;

FIG. 8 depicts a schematic side view of the embodiment of a test device according to the invention illustrated in FIGS. 4A-4C and FIG. 5;

FIG. 9 depicts one embodiment that directly detects hCG-H;

FIG. 10 depicts another embodiment that directly detects hCG-H;

FIG. 11 depicts an embodiment including a scavenging component, where the device indirectly detects hCG-H;

FIG. 12 depicts another embodiment including a scavenging component, where the device indirectly detects hCG-H;

FIG. 13A depicts a multi-line test device indicating that the user is not pregnant and that the device is functioning properly;

FIG. 13B depicts a multi-line test device indicating that the user is pregnant, that the pregnancy is viable, and that the device is functioning properly;

FIG. 13C depicts a multi-line test device indicating that the user is pregnant, that the pregnancy is not viable, and that the device is functioning properly FIG. 14 depicts a multi-strip test device;

FIG. 15 depicts a multi-strip test device including a common release medium;

FIG. 16 shows Biacore sensorgrams for SMA 4D8 against normally glycosylated hCG;

FIG. 17 shows Biacore sensorgrams for SMA 4D8 against free β hCG;

FIG. 18 shows Biacore sensorgrams for SMA 4D8 against recombinant hCG;

FIG. 19 shows Biacore sensorgrams for SMA 4D8 against JEG-3 hCG-H;

FIG. 20 shows the SMA 4D8 ELISA antigen fingerprinting to illustrate the differential recognition of hCG antigens by SMA 4D8;

FIG. 21 shows Biacore sensorgrams for SMA 3E8 against normally glycosylated hCG;

FIG. 22 shows Biacore sensorgrams for SMA 3E8 against free β hCG;

FIG. 23 shows Biacore sensorgrams for SMA 3E8 against recombinant hCG;

FIG. 24 shows Biacore sensorgrams for SMA 3E8 against JEG-3 hCG-H;

FIG. 25 shows the SMA 3E8 ELISA antigen fingerprinting to illustrate the differential recognition of hCG antigens by SMA 3E8;

FIG. 26 shows Biacore sensorgrams for B152 against normally glycosylated hCG;

FIG. 27 shows Biacore sensorgrams for B152 against free β hCG;

FIG. 28 shows Biacore sensorgrams for B152 against recombinant hCG;

FIG. 29 shows Biacore sensorgrams for B152 against JEG-3 hCG-H;

FIG. 30 shows the respective color intensity of particular embodiments according to the present invention as compared to production devices;

FIG. 31 shows a summary of results for tests using particular embodiments conducted on hCG free urine samples of differing non-surge LH values;

FIG. 32 shows a summary of results for tests using particular embodiments conducted on hCG free urine samples of differing concentrations of LH surge samples;

FIG. 33 shows a summary of results for tests conducted using particular embodiments on of peri- and post-menopausal urine samples with varying levels of pituitary hCG;

FIG. 34 shows a set of data obtained from tests conducted using particular embodiments on well characterized clinical urine samples from early pregnancy;

FIG. 35 shows an additional set of data obtained from tests conducted on well characterized clinical urine samples from early pregnancy; and FIG. 36 shows data from tests conducted using particular embodiments on four cycles of women who suffered early pregnancy loss (EPL).

DETAILED DESCRIPTION OF THE INVENTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In one aspect, the present invention provides a pregnancy test device, such as an OTC or POC pregnancy test. The device includes a proximal portion in fluid communication with a distal portion. A liquid sample (e.g., urine) can be directly or indirectly deposited on the proximal portion of the device for transport to the distal portion. In general, embodiments of the present invention include a first binding member located on the proximal portion of the device and a second binding member deposited on the distal portion of the device. Preferably, at least one of the binding members exhibits a moderate to high affinity for hCG-H while also being selectively or preferentially reactive with an epitope of the hCG-H. Such devices also include a capture site located on the distal portion of the device that directly or indirectly binds the hCG-H. The presence of hCG-H in the liquid sample can be determined by visual inspection of the capture site, where the presence of hCG-H is indicated by the presence of color development at the capture site. Accordingly, embodiments of the present invention provide a device that selectively or preferentially detects hCG-H.

As used herein, "antibody" refers to a polypeptide substantially encoded by an immunoglobulin gene or immunoglobulin genes, or fragments thereof, which specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The term "antibody," as used herein, also includes antibody fragments either produced by the modification of whole antibodies or those synthesized de novo using recombinant DNA methodologies, and further includes "humanized" antibodies made by now conventional techniques.

An antibody "specifically binds to", "is selectively reactive with" or "is selectively immunoreactive with" a protein or epitope thereof when the antibody functions in a binding reaction with the protein without significantly binding with other proteins. In order for the antibody to bind to a protein, the protein should contact the antibody. Accordingly, contacting a sample suspected of containing an antigen of interest with an antibody to the antigen will permit the antibody to bind the antigen. The binding of the antibody to the protein permits determination of the presence of the protein in a sample in the presence of a heterogeneous population of proteins and other agents. Thus, under designated immunoassay conditions, the specified antibodies selectively bind to a particular protein and do not significantly bind to other proteins present in the sample (e.g., greater than 90% or 95% differential discrimination). Specific binding to a protein under such conditions requires an antibody that is selected for specificity or selectivity for a particular protein. Several methods for determining whether or not a peptide is immunoreactive with an antibody are known in the art. In certain embodiments, an antibody "preferentially binds to", "is preferentially reactive with" or "is preferentially immunoreactive with" hCG-H if the antibody exhibits greater than 50% differential discrimination of hyperglycosylated hCG over regular hCG. In certain embodiments, an antibody "preferentially binds to", "is preferentially reactive with" or "is preferentially immunoreactive with" hCG-H if the antibody exhibits greater than 60%, 70%, 80, or 90% differential discrimination of hyperglycosylated hCG over regular hCG. Similarly, an antibody "preferentially binds to", "is preferentially reactive with" or "is preferentially immunoreactive with" regular hCG if the antibody exhibits greater than 50% differential discrimination of regular hCG over hyperglycosylated hCG. In certain embodiments, an antibody "preferentially binds to", "is preferentially reactive with" or "is preferentially immunoreactive with" regular hCG if the antibody exhibits greater than 60%, 70%, 80, or 90% differential discrimination of regular hCG over hyperglycosylated hCG.

In some embodiments, the present invention specifically differentiates between hyperglycosylated hCG and "regular" hCG. As used herein, "regular" hCG should be understood as encompassing any form of hCG that is not hyperglycosylated. Thus, regular hCG may encompass naturally occurring hCG that is not hyperglycosylated and/or recombinant hCG that is not hyperglycosylated. Regular hCG may further be delineated as being normally glycosylated (i.e., the type and degree of glycosylation normally found in the human body) or being non-glycosylated.

As used herein a "moderate to high affinity" antibody or binding member thereof comprises an antibody or binding member that can bind with a particular antigen within a relatively short incubation time. Likewise, an antibody or binding member thereof "exhibits a moderate to high affinity" for a particular antigen should be understood as requiring a relatively short sample incubation time. For instance, an antibody or binding member exhibits "moderate to high affinity" at equilibrium ("KA") greater than $1e^9$ (e.g., $1e^9$ to $1e^9$, $1e^9$ to $1e^{10}$, or $1e^{10}$ to $1e^{12}$) or preferably at least $1e^{10}$ (e.g., $1e^{10}$ to $1e^{12}$). In certain embodiments, KA values at equilibrium between about $1e^9$ to $1e^{10}$ can be deemed as exhibiting a moderate affinity, while KA values at equilibrium of at least $1e^{10}$ can be deemed as exhibiting a high affinity. At equilibrium, KA values of $1e^8$ or less can be deemed as exhibiting a low affinity. Such KA values can be experimentally determined using any suitable method known in the art. Specifically, such KA values can be determined by analysis with a Biacore (GE Healthcare) instrument according to the procedure set forth in the Examples section herein.

As used herein, a "capture antibody" should be understood as an antibody, such as a monoclonal or polyclonal antibody, attached to a substrate directly or indirectly, such as a solid substrate. The capture antibody can include at least one binding member that specifically or preferentially binds a particular, distinct epitope of an antigen, such as hCG-H or regular hCG.

According to embodiments of the present invention, a pregnancy test device is provided including at least one moderate to high affinity antibody which selectively or preferentially recognizes and binds hCG-H. Preferably, such moderate to high affinity antibodies exhibit limited to minimal binding to regular hCG or other hCG related molecules that may be present in a liquid sample. For instance, two sheep monoclonal antibodies (SMA's) have been developed which selectively or preferentially recognize and bind hCG-H. Examples of antibodies that are selectively or preferentially reactive with hCG-H that specifically may be used according to the present invention are SMA 3E8 and SMA 4D8, which are available from Church & Dwight, Inc. (Princeton, N.J.). For instance, FIG. 1 provides normalized data for high affinity antibodies 3E8 and 4D8 compared to that of a known antibody (i.e., CCFO1) when used in a traditional lateral flow format. The legend for FIG. 1 lists hCG-H (i.e., hyperglycosylated hCG), hCG (normally glycosylated hCG), and recombinant hCG (i.e., poorly-glycosylated hCG). FIG. 1 illustrates that both 3E8 and 4D8 display desirable discrimination between hCG-H and recombinant hCG when compared to the prior art antibody used in current pregnancy tests. In particular, the prior art antibody exhibited about a 30% hCG-H discrimination while 3E8 exhibited about a 70% hCG-H discrimination and 4D8 exhibited about an 85% hCG-H discrimination.

As shown in FIGS. 2A-2C, three antibody pairs (i.e., 3 separate devices each having a unique pair of antibodies) were compared to two different versions of devices marketed by Church and Dwight Co., Inc. under the brand name FIRST RESPONSE® Early Result. The two production devices were the First Response Early Result pregnancy test (hereinafter referenced as "FR1" and in the Figures) and Upgraded First Response Early Result pregnancy test (hereinafter referenced as "FR2" and in the Figures). The FR1 devices utilize a labeled binding antibody (i.e., large particle size gold as the label) striped on the release medium and monomeric streptavidin immobilized on the capture medium. The FR2 devices are similar to the FR1 devices except the FR2 devices use polymerized streptavidin.

FIGS. 2A-2C provide normalized data for devices according to certain embodiments in an avidin-biotin lateral flow format of the present invention compared to that of production devices currently available. Moderate to high affinity antibodies 3E8 and 4D8 were biotinylated and converted to biotin probe striping solutions (0.1 mg/ml). These striping solutions were then striped on the release medium of a biphasic test strip with either 11D6-2B10 large gold probe (OD30) or CCFO1 large gold probe (OD30). The capture mediums were striped with 1.5 mg/ml polymerized streptavidin and GAM. Each of the devices was separately tested with urine samples containing 25, 12.5, or 6.25 mIU/ml of 4 different hCG standards: JEG-3 derived hCG-H (i.e., hyperglycosylated hCG), regular hCG (i.e., normally glycosylated hCG), recombinant hCG (i.e., non-glycosylated hCG), and WHO hCG beta subunit.

FIG. 2A shows the normalized data for each device tested with 25 mIU/ml of the four hCG standards. Each of the devices including an antibody having a moderate to high affinity for hCG-H exhibited a differential discrimination of hyperglycosylated hCG and recombinant hCG of around 80%. FIG. 2B shows similar results for each device having been tested with 12.5 mIU/ml of each standard. FIG. 2C shows similar results for each device having been tested with 6.25 mIU/ml of each standard. Each of FIGS. 2B and 2C illustrate the desirably increased level in differential discrimination achieved according to these particular embodiments of the present invention.

Further, the biomolecular interactions between antibodies SMA 4D8 and SMA 3E8 and various antigens were analyzed to evaluate the relative specificity and affinity of each antibody for each antigen. Thus, an 'antigen fingerprinting' has been performed for both antibodies; the results of which are discussed in detail in the Examples section. As discussed in the Examples section, antibodies that show a moderate to high affinity for hCG-H and a reduced or lower affinity for other antigens, such as SMA 4D8 and SMA 3E8, are particularly useful according to the invention.

Embodiments of the present invention preferably make use of a conjugate comprising an antibody bound to a detectable label component (which can be colored particles, such as a metal sol or colloid, preferably gold or latex beads or soluble dyes). The conjugate can take two distinct forms, depending on whether the assay is designed to exploit the "sandwich" or "competitive" technique.

Any detectable label recognized in the art as being useful in various assays could be used in the present invention. In particular, the detectable label component can include compositions detectable by spectroscopic, photochemical, biochemical, immunochemical, or chemical means. As such, the label component produces a detectable signal. For instance, suitable labels include soluble dyes, fluorescent dyes, chemiluminescent compounds, radioisotopes, electron-dense reagents, enzymes, colored particles, or dioxigenin. The label component can generate a measurable signal, such as radioactivity, fluorescent light, color, or enzyme activity, which can be used to identify and quantify the amount of label bound to a capture site. Thus, the label component can also represent the presence or absence of a particular antigen bound thereto.

In certain embodiments, the label component preferably comprises a gold colloid having a mean particle size of about 50 nm to about 100 nm prior to formation of the labeled conjugate More preferably, the mean particle size can range from about 60 nm to about 80 nm prior to formation of the labeled conjugate In embodiments wherein the device of the invention makes use of a sandwich technique, the antibody used in the detection comprises a binding member or site which binds to an epitope on the analyte for detection, such as hCG-H. The antibody preferably has a label component bound thereto to provide a labeled antibody. The labeled antibody reacts with the analyte to form a complex in the liquid sample. The analyte, which is bound with the labeled antibody, reacts with a capture antibody to form a "sandwich" comprising the capture antibody, analyte, and the labeled antibody. This sandwich complex is progressively produced as the test liquid with the analyte therein continuously moves along the test strip of the device. As more and more analyte/labeled antibody complex is immobilized as a sandwich with the capture antibody at the capture site, the label components aggregate and become visible through a viewing window, indicating the presence of a particular analyte in the liquid sample.

Embodiments of the invention can include one or more standards or internal controls that allow for determination of whether signal development (e.g., color development) is a true indication of the presence or absence of analyte (e.g., hCG-H) in the sample or is simply an artifact, such as caused by nonspecific sorption. For example, in one embodiment employing the sandwich technique, the standard consists of a negative control site, preferably disposed adjacent the test site, and visible through a second window proximate the first. The negative control site preferably is prepared identically to the test site, except immobilization of the binding protein is omitted. Therefore, although the conjugate will reach the site, it aggregates due only to non-specific binding. If the test site is not appreciably more intense in color than the negative control site, the assay is considered negative.

In certain embodiment, the device can include a positive control. Thus, when exploiting the sandwich technique for example, a cell may have an authentic sample of the analyte for detection immobilized at a control site. If no color develops at this control site, the assay is considered inconclusive. When exploiting the competitive technique, the development of color at the positive control site means the assay results are inconclusive.

In yet another embodiment, which can be particularly useful when the pregnancy test device comprises a biphasic test strip medium, the biphasic medium comprises a control site disposed on the capture medium downstream of the capture site. The control site has immobilized thereon at least one capture antibody (e.g., a protein). The primary function of the control site is to capture and immobilize labeled antibody which has not been captured at the capture site.

According to various embodiments, the control site can include polyclonal antisera specific for the labeled antibody immobilized thereon. Indication of the presence of the label component at the control site indicates proper functioning of the test, irrespective of the presence or absence of analyte in the sample. Preferably, both the capture and control sites are visible through the window of the casing. In a preferred embodiment, the inventive device incorporates a biphasic chromatographic medium (or test strip) which enhances the speed and sensitivity of the assay. Generally, a biphasic substrate element useful according to the invention comprises a release medium joined to a capture medium located downstream of the release medium. The release and capture media preferably comprise two different materials or phases having different specific characteristics. The two phases are joined together to form a single liquid path such that a solvent front can travel unimpeded from the proximal (upstream) end of the release medium (which can be defined as a proximal portion of the biphasic medium) to the distal (downstream) end of the capture medium (which can be defined as a distal portion of the biphasic medium).

Reagents for detecting, labeling, and capturing an analyte of interest are disposed on the release and capture media. In certain embodiments, a labeled conjugate is located on the release medium and includes a binding member reactive with a particular site (sometimes referred to as a "first epitope") on the analyte of interest. The labeled conjugate further comprises a detectable marker (or label), preferably colloidal gold. A capturable conjugate can be located on the release medium downstream of the binding member, which conjugate comprises an antibody with a binding agent reactive with another particular site (sometimes referred to as a "second epitope") on the analyte of interest. The first epitope and the second epitope are preferably different sites on the analyte. The capturable conjugate also comprises one member of an affinity pair and is capable of forming a complex with the labeled binding member and the analyte. The labeled conjugate and the capturable conjugate both are releasably bound to the release medium such that when the solvent front created by the liquid sample being analyzed passes through the release medium, the labeled conjugate and the capturable conjugate both become solubilized by the liquid and flow with the solvent along the liquid path. In operation, if any analyte is present in the liquid sample, it reacts first with the labeled conjugate, then with the capturable conjugate as the front advances along the liquid path to form a diffusible sandwich complex which is then transported by capillary action. Thus, by the time the solvent front reaches the capture medium section of the biphasic material, the capturable sandwich complex has formed.

In embodiments such as those described above, the capture medium contains the reagents used to capture the complex described above. Generally, the reagents are located on a capture site and comprise the other member of the affinity pair specific for the moiety comprising the capturable conjugate and a reagent specific for the labeled binding member. Upon diffusion into the capture medium, the diffusible sandwich complex becomes concentrated by the interaction of the capture affinity member with the capturable affinity moiety yielding a visual signal. The affinity member is immobilized, preferably by simple adsorption, at the capture site, and does not advance with the solvent front.

The release medium can be formed from a substance which allows for release of indicator reagents. In certain embodiments, the release medium comprises a bibulous, hydrophilic material, such as absorbent materials. Preferred materials for use as a release medium include, but are not limited to, cotton linter, cellulosic materials, or materials made of cellulose together with a polymeric fibrous material, such as polyamide or rayon fibers, and glass fiber material. The primary function of the release medium is first to support and to subsequently release and transport various immunological components of the assay, such as a labeled conjugate and/or a capturable conjugate, both of which are capable of binding to the analyte of interest. This release and transport occurs during routine operation of the assay. Generally, the release medium can be formed of any material capable of performing the function of holding, releasing, and transporting various immunological parts of the test such as the labeled test component.

Specific, non-limiting examples of materials useful in forming the release medium include: cotton linter paper, such as S&S 903, S&S GB002, and BFC 180 (available from Whatman, Fairfield, N.J.); cellulosic materials, such as Grade 939 made of cellulose with polyamide, Grade 989 made of cellulose blend fiber, and Grade 1278 and Grade 1281 made of cellulose and rayon with polyamide (available from Ahlstrom Corporation, Mt. Holly Springs, Pa.); and glass fiber, such as Lydall borosilicate (available from Lydall, Inc., Rochester, N.H.). The release medium preferably is coated with an aqueous solution containing bovine serum albumin (BSA) and a nonionic surfactant, such as Triton X-100 (available from Rohm & Haas Co., Philadelphia, Pa.) in order to prevent nonspecific binding and facilitate release of the diffusible reagents. A combination of about 3% BSA and about 0.1% Triton X-100 is useful for this purpose.

The capture medium can be formed from a substance which permits immobilization of reagents for detection of the presence of analyte in the test fluid. The capture medium generally comprises hydrophilic polymeric materials, such as microporous films or membranes, which permit protein reagents to be immobilized directly on the membrane by passive adsorption without the need for chemical or physical fixation. Of course, the use of chemical or physical fixation is not precluded by the invention, and any known method for immobilizing the reagents to the membrane can be used.

Non-limiting examples of materials useful as the capture medium comprise a microporous polymeric film of nitrocellulose, nylon (e.g., nylon 66), or similar materials, or combinations of such materials. Materials for use as the capture medium preferably have a pore size in the range of from about 5 µm to about 20 µM. In specific embodiments, the nitrocellulose membrane may be nitrocellulose alone or a mixed ester of nitrocellulose, such as in combination with an ester of nitric acid and/or other acids. The nitrocellulose membrane preferably is coated or laminated onto a translucent or transparent polymeric film to provide physical support for the membrane.

In a preferred embodiment, a nitrocellulose polymer which has been cast onto a polyester film, such as MYLAR®, is used. Alternatively, a nitrocellulose membrane laminated onto a polyester film also may be used, although other backing materials besides polyester may be used. Pre-laminated or pre-cast sheets useful in the present invention are commercially available, for example, from Millipore Corporation, Bedford, Mass. and Sartorius Corporation, Edgewood, N.Y.

In one embodiment, the release medium and capture medium are joined by overlapping the downstream edge of the release medium over the upstream edge of the capture medium, then adhering the resulting biphasic material to a clear polymer film or opaque sheet, thereby holding the media in place. The overlapping region allows for the efficient and rapid transfer of analyte containing fluid from the release medium to the capture medium.

While the rapid transfer associated with the overlapping region is useful, the manufacturing issues associated with reproducibly generating a small overlapping region, such as necessary with small devices, can be difficult. Therefore, in certain embodiments, the invention also provides a test device having a biphasic design as described herein but wherein the release medium and the capture medium do not overlap but rather are connected by a non-overlapping butt joint. In such embodiments, the fluid front moving along the test strip is transferred from the release medium to the capture medium through bridging the non-overlapping region by capillary action.

Beneficially, the butt joining of the phases can maintain the same efficacy of the overlapping of the phases, even after accelerated aging of the devices. Thus, the use of a butt joint simplifies the manufacture of the present test device without any loss of performance in the device.

The diffusible and non-diffusible reagents can be applied to the release and capture media, respectively, by any suitable technique. In one embodiment, the diffusible reagents are applied to the release medium by direct application onto the surface of the medium and dried to form a narrow band.

In one preferred embodiment, the device comprises a casing defining a sample inlet, a test volume, and reservoir volume. Disposed within the casing are a sample absorbent, the biphasic chromatographic substrate(s), and reservoir absorbent. The sample absorbent is preferentially disposed within the casing and extending to the exterior thereof. Located downstream of the sample absorbent is the biphasic chromatographic substrate comprising a release medium and a capture medium joined together to form a single liquid path. The release and capture media can be laminated onto a transparent plastic film or sheet.

The sample absorbent preferably is a bibulous hydrophilic material which facilitates absorption and transport of a fluid sample to the biphasic chromatographic medium. Such materials may include cellulose acetate, hydrophilic polyester, and other materials having similar properties. Further, a combination of absorbent materials also may be used. Non-limiting examples of useful materials include bonded cellulose acetate, bonded polyolefin, or hydrophilic polyester, such as those materials commercially available from Filtrona Fibertec Company (Colonial Heights, Va.). Other useful materials include absorbent matrices, such as Grade 939, Grade 989, Grade 1278, or Grade 1281, available from Ahlstrom Corporation. The sample absorbent preferably is coated with a buffered solution containing BSA and a nonionic surfactant, such as Triton X-100. The presence of BSA and surfactant minimize non-specific adsorption of the analyte. A concentration of about 1% BSA and about 0.2% surfactant in tris buffer can be effective for this purpose.

By providing a reservoir of sorbent material disposed beyond the chromatographic substrate, a relatively large volume of the test liquid and any analyte it contains can be drawn through the test area to aid sensitivity. The reservoir absorbent generally facilitates capillary action along the chromatographic substrate and absorbs excess liquid contained within the device. The reservoir absorbent preferably compromises absorbent paper made from cotton long linter fibers, such as CF3, CF4, CF5, or 470 (available from Whatman) or cellulosic materials, such as Grade 3mM (available from Whatman) and Grade 320 (available from Alhstrom).

In using a device according to various embodiments of the invention, the proximal portion of the biphasic substrate is contacted with the liquid sample being analyzed, wherein the liquid sample can be collected either directly or through the absorbent material comprising the sample collector. The casing of the device may be configured to permit direct contact with a body fluid or as a dipstick for dipping in a container of body fluid or other test solution. The liquid sample travels impelled by surface effects such as by capillary action along the liquid path formed by the substrate. More specifically, the test sample passes through the biphasic chromatographic substrate and into reactive contact with the test site (and optionally one or more control sites). Preferably, at least the test site is visible to a user, such as through one or more windows in the device's exterior casing. In a preferred embodiment, the labeled binding member recognizing the analyte is disposed in preserved form on the release medium in the flow path within the device.

In one embodiment, if the analyte of interest is present in the sample, it passes through the inlet and the interior of the device where it sequentially reacts with the labeled antibody and the capturable antibody with the affinity agent, thereby forming the capturable complex. The complex formed by the analyte, labeled antibody, and the capturable antibody then reacts with the immobilized capture component at the capture site, the capture component being specific for the affinity agent on the capturable antibody. This process results in the labeled complex accumulating at the capture site. The presence of the analyte is determined by observing the presence of the detectable marker at the capture site. If no analyte is present in the sample, the capturable complex does not form and no detectable marker will be present at the capture site. If a control site is present, the unbound complex or the free labeled binding member will accumulate at the control site.

In yet another embodiment, if the analyte of interest is present in the sample, it passes through the inlet and the interior of the device where it reacts with a labeled antibody which is releasably attached to the release medium. The liquid sample wicks up the release medium and fauns a sandwich complex with a capture antibody which is immobilized on the capture medium and defining a capture site. As the sample front passes across the capture sites, a complex is formed comprising the analyte, labeled antibody, and the capture antibody. Preferably, at least one of the labeled antibody and the capture antibody includes a binding member that exhibits a moderate to high affinity for hCG-H. This process results in the labeled complex accumulating at the capture site. The presence of the analyte (e.g. hCG-H) is determined by observing the presence of the detectable marker at the capture site. If no analyte is present in the sample, the complex does not form and no detectable marker will be present at the capture site. If a control site is present, the free labeled binding member will accumulate at the control site.

Illustrations of one embodiment of a test device 5 according to the present invention are shown in FIGS. 3A-E. The test device 5 comprises an outer, molded casing 10 which defines a hollow, elongate enclosure. The casing 10 includes a test liquid inlet 14 and an opening 16 comprising a window through which the capture site (and control site, if applicable) is visible. As illustrated in FIGS. 3A-E, the window 16 is disposed on a side of the casing 10 opposite the sample inlet 14. This configuration reduces the incidence of contamination of the test site which is disposed in the interior of casing 10 and is exposed through the window 16. The casing 10 further defines vent openings 38, 40, and 42 located along the sides and at the distal portion of the casing 10. The vent opening 38 reduces the incidence of "vapor lock" within the device during use. The presence of the openings 40 and 42 help to reduce "flooding" of the chromatographic substrate, which may occur when the user applies too much sample to the device.

A preferred embodiment of the test device 5 is illustrated in FIGS. 4A-E. As seen therein, the test device 5 comprises an outer, molded casing 10 which defines a hollow, elongate enclosure. The casing 10 includes an opening 16 comprising a window through which the capture site (and control site, if applicable) is visible. The test device 5 further includes a test liquid inlet 14, which is covered by a removable cap 60. In this embodiment, the test liquid inlet 14 is external to the casing 10 and is covered by the cap 60 except when in use. Providing the test liquid inlet 14 external to the casing 10 allows for ease of application of the test liquid to the test device 5, such as by placing the test liquid inlet 14 in the path of a urine stream or dipping in a container holding the test liquid. The cap 60 is re-attachable (such as "snap-fitting" onto the lip 62 extending from the casing 10) and can be replaced after application of the test liquid to avoid contamination of the sample while the test is proceeding. The test liquid inlet 14 external to the casing can be a portion of the absorbent material 12, as illustrated in FIG. 5 and described below. In further embodiments, the test liquid inlet 14 can be a portion of the biphasic chromatographic substrate 18. The casing 10 further includes a test strip support 70 located on the bottom surface of the casing 10.

A specific embodiment of the assay materials for use according to the invention is illustrated in FIG. 5. When the device is fully assembled, the assay materials of FIG. 5 preferably are disposed inside a casing. The assay materials comprise an absorbent material 12, a biphasic chromatographic substrate 18, and a reservoir material 24. The assay materials and the interior of the casing together define a flow path. When the inlet 14 is disposed within or otherwise in contact with a liquid sample, the liquid is transported by capillary action, wicking, or simple wetting along the flow path downstream through the absorbent 12, along the chromatographic substrate 18, and into the reservoir 24, generally as depicted by the arrow. The absorbent material also serves as a filter which can remove from impure test samples particulate matter and interfering factors.

Illustrated in FIG. 6 is a biphasic chromatographic substrate 18, comprising a release medium 30 and a capture medium 32. The horizontal dashed line represents the interface between the release medium 30 and the capture medium 32. As previously noted, this interface can be in the form of an overlapping relationship. Alternatively, the release medium 30 can be butted up to the capture medium 32. Releasably disposed on the release medium 30 is a band 26 of labeled binding member, e.g., an antibody-metal sol. In one embodiment, the labeled biding member is in dehydrated form. As the liquid sample moves past the band 26, the labeled binding member becomes entrained in the liquid, reconstituted (in the case of a dehydrated binding member), and reacts or competes with any analyte present in the liquid sample. Disposed downstream of the labeled binding member is a band 28 of preferably dehydrated capturable complex. The capturable complex comprises a binding member which binds to a second epitope of the analyte, e.g. an antibody, and a capturable affinity component, e.g. biotin. The capturable complex also becomes entrained in the liquid sample as it advances along the substrate 18.

Immobilized on the capture medium 32 are, respectively, the capture site 34 and the control site 36. In FIG. 6, the control and capture sites are illustrated as being disposed serially along the flow path. Alternatively, the control and capture site or sites may be disposed side by side, perpendicular to each other, or in other spatial relationships. The capture site 34 comprises a quantity of a capture affinity member specific for the capturable affinity component disposed on the release medium. For example, when the capturable affinity member is biotin, the capture component may be streptavidin. Of course, any such complementary system of components could be used in place of biotin and streptavidin. The control site 36 typically comprises immobilized antisera, antibody, or a protein binder such as Protein A or Protein G capable of binding the labeled binding member.

In certain embodiments, as illustrated in FIG. 7, a band 26 of labeled binding member, e.g., an antibody-metal sol., can be releasably disposed on the release medium 30. In one embodiment, the labeled binding member is in dehydrated form. As the liquid sample moves past the band 26, the labeled binding member becomes entrained in the liquid, reconstituted (in the case of a dehydrated binding member), and reacts or binds with a particular analyte or analytes of interest present in the liquid sample. Accordingly, the resulting conjugate comprising a binding antibody, a label component, and an analyte for identification (e.g., hCG-H) advances along with the sample front until the reaching the capture site 34. In this particular embodiment, the capture site includes at least one immobilized capture antibody having a binding member which binds to a second epitope of the analyte. Accordingly, a "sandwich" including the desired analyte is formed at the capture site 34. If desired, a control site 36 can include immobilized antisera, antibody, or protein such as Protein A or Protein G capable of binding the labeled binding member.

A side view of one embodiment of the operative portion of the assay materials is schematically illustrated in FIG. 8. As shown, the absorbent material 12 is disposed proximate the release medium 30, and overlaps the release medium 30 at one end. The release medium 30 in turn overlaps the capture medium 32, which is disposed distal to the release medium 30. Again, the release medium 30 and the capture medium 32 may alternatively be connected via a butt joint rather than being in overlapping connection. The reservoir 24 overlaps the distal portion of the capture medium 32. These four components together form a single fluid path, and they cooperate to cause sample liquid to flow from the absorbent 12 along the release medium 30 and the capture medium 32 into the reservoir 24.

The invention is not limited by the precise nature of the capture site 34 and the corresponding control site 36, and in fact, the control site 36 may be entirely eliminated if desired. Generally, antibody or other affinity agent can be immobilized at the capture site 34 and the control site 36 using absorption, adsorption, or ionic or covalent coupling, in accordance with methods known per se. The capture medium 32 preferably is selected to bind the capture reagents without the need for chemical coupling. Nitrocellulose and nylon both permit non-chemical binding of the capture component and control reagent.

Disposed downstream of the capture medium 32 is the reservoir 24 comprising a relatively large mass of absorbent or superabsorbent material. The purpose of reservoir 24 is generally to ensure that a reasonably large amount of test liquid is drawn across the chromatographic medium. In certain embodiments, the sample absorbent 12 can be omitted, and the release medium 30 can itself act as the sample absorbent. Such embodiments of the assay materials are useful in performing dipstick assays.

Direct Detection

In one aspect, the present invention provides devices wherein detection includes directly binding hCG-H. In such embodiments, at least one of the release medium and the capture medium includes a binding member that exhibits a moderate to high affinity for hCG-H and is selectively or preferentially reactive with hCG-H.

In various embodiments, the release medium includes a labeled conjugate comprising the detectable label and a first binding member that is reactive with at least one epitope of hCG-H or an epitope of regular hCG. The capture medium includes a capture site comprising a second binding member that is reactive with at least one epitope of hCG-H or an epitope of regular hCG. However, at least one of the first binding member and the second binding member preferably exhibits a moderate to high affinity for hCG-H and is selectively or preferentially reactive with hCG-H. For example, in one embodiment, only the first binding member exhibits a moderate to high affinity for hCG-H and is selectively or preferentially reactive with hCG-H while in another embodiment only the second binding member exhibits a moderate to high affinity for hCG-H and is selectively or preferentially reactive with hCG-H. Alternatively, certain embodiments can include a first binding member and a second binding member that both exhibit a moderate to high affinity for hCG-H and are selectively or preferentially reactive with hCG-H.

As illustrated by FIG. 9, the device for selectively detecting hCG-H in a liquid sample, according to one embodiment, comprises a biphasic substrate 18. The biphasic substrate 18 can include a release medium 30 formed of a first material and comprising a region including a labeled antibody 26 that includes a binding member reactive with a first epitope of hCG-H or regular hCG and a capture medium 32 in fluid communication with the release medium. Preferably, the capture medium 32 can be formed of a second, different material, and include a capture site 34 having an immobilized capture antibody thereon. The immobilized capture antibody can comprise a member reactive with a second epitope of hCG-H or regular hCG, such that if hCG-H is present in the sample, a sandwich complex is formed comprising the labeled antibody, hCG-H, and the immobilized capture antibody. In one preferred embodiment, at least one of the labeled antibody and the immobilized capture antibody includes a binding member that exhibits a moderate to high affinity for hCG-H and is selectively or preferentially reactive with hCG-H. According to one such embodiment, the immobilized capture antibody comprises a binding member that exhibits a moderate to high affinity for hCG-H and is selectively or preferentially reactive with hCG-H. In another embodiment, the labeled antibody comprises a binding member that exhibits a moderate to high affinity for hCG-H and is selectively or preferentially reactive with hCG-H. In one alternative embodiment, the labeled antibody includes a binding member that exhibits a moderate to high affinity for hCG-H and is selectively or preferentially reactive with a first epitope of hCG-H and the immobilized capture antibody also comprises a member that exhibits a moderate to high affinity for hCG-H and is selectively or preferentially reactive with a second epitope of hCG-H.

According to certain embodiments, at least one of the capture antibody or the labeled antibody comprises SMA 3E8. In other embodiment, at least one of the capture antibody or the labeled antibody comprises SMA 4D8. Alternatively, one embodiment of the invention comprises a release medium having releasably attached thereto a labeled antibody comprising SMA 3E8 and a capture medium having immobilized thereon a capture antibody comprising SMA 4D8. Another embodiment comprises a release medium having releasably attached thereto a labeled antibody comprising SMA 4D8 and a capture medium having immobilized thereon a capture antibody comprising SMA 3E8. Of course, further antibodies that show a moderate to high affinity for hCG-H and a reduced or lower affinity for other antigens also could be used. In various embodiments, the release medium and the capture medium can be in either non-overlapping fluid communication or overlapping communication.

The release medium, according to one embodiment of the present invention, includes a labeled conjugate comprising the detectable label and a first binding member reactive with a first epitope of hCG-H and a biotinylated capturable component including a second binding member reactive with a second epitope of hCG-H. Preferably, at least one of the first binding member and the second binding member exhibits a moderate to high affinity for hCG-H and is selectively or preferentially reactive with hCG-H. As such, when a sample includes hCG-H, a sandwich complex is formed comprising the labeled conjugate, hCG-H, and the biotinylated capturable component. In such embodiments, the capture medium comprises a capture site having immobilized thereon a capture component comprising streptavidin. In one such embodiment, only the first binding member exhibits a moderate to high affinity for hCG-H and is selectively or preferentially reactive with hCG-H. In yet another such embodiment, only the second binding member exhibits a moderate to high affinity for hCG-H and is selectively ore preferentially reactive with hCG-H. In one alternative embodiment, both the first binding member and the second binding member exhibit a moderate to high affinity for hCG-H and are selectively or preferentially reactive with hCG-H.

As illustrated in FIG. 10, the device for selectively detecting hCG-H in a liquid sample, according to one embodiment, comprises a biphasic substrate 18 including a release medium 30 formed of a first material and a capture medium 32 in fluid communication with the release medium and formed of a second, different material. The release medium 30 includes a labeled binding conjugate 26 comprising a binding member reactive with a first epitope of hCG-H or hCG and a biotinylated capturable component 28 having a site reactive with a second epitope of hCG-H or hCG, such that if hCG-H is present in the sample, a sandwich complex is formed comprising the labeled binding conjugate 26, hCG-H, and the biotinylated capturable component 28. Preferably, at least one of the labeled binding conjugate 26 and the biotinylated capturable component 28 includes a binding member that exhibits a moderate to high affinity for hCG-H and is selectively or preferentially reactive with hCG-H. The capture medium 32 includes a capture site 34 for capturing the complex, wherein the capture site includes a capture component immobilized thereon. The capture component can comprise streptavidin. Further, such embodiments can optionally include a control site 36. In certain embodiments, the control site 36 can comprise either a negative or positive control as discussed earlier.

According to embodiments including streptavidin as a capture component, the streptavidin used in the preparation of test devices according to the invention preferably comprise a streptavidin solution that can be applied to the test device, thereby immobilizing streptavidin on the substrate. The streptavidin in the solution can comprise a number of polymerized forms, such as dimeric, trimeric, tetrameric, or the like. While monomeric streptavidin can be present in the solution, the solution preferably comprises a majority of polymerized streptavidin, the total content of any monomeric streptavidin in the solution comprising only a minority of the total content of the solution. In specific embodiments, the streptavidin solution comprises polymerized streptavidin in an amount such that the polymerized streptavidin comprises at least 50% by weight of the streptavidin solution. Preferably, the solution comprises at least about 55% by weight, at least about 60% by weight, at least about 75% by weight, or at least about 90% by weight of polymerized streptavidin.

In one embodiment of the present invention, only the biotinylated capturable component comprises a binding member that exhibits a moderate to high affinity for hCG-H and is selectively or preferentially reactive with hCG-H. In other embodiments, only the labeled conjugate comprises a binding member exhibiting a moderate to high affinity for hCG-H and is selectively or preferentially reactive with hCG-H. In one alternative embodiment, both the biotinylated capturable component and the labeled conjugate comprise a binding member exhibiting a moderate to high affinity for hCG-H and are selectively or preferentially reactive with hCG-H. For instance, one embodiment can comprise a labeled conjugate including a binding member exhibiting a moderate to high affinity of hCG-H and being selectively or preferentially reactive with a first epitope of hCG-H and the biotinylated capturable component can comprises a different binding member that exhibits a moderate to high affinity for hCG-H and is selectively or preferentially reactive with a second epitope of hCG-H.

According to certain embodiments, at least one of the biotinylated capturable component or the labeled antibody comprises SMA 3E8. In other embodiment, at least one of the biotinylated capturable component or the labeled antibody comprises SMA 4D8. Alternatively, one embodiment of the invention comprises a release medium having releasably attached thereto a labeled antibody comprising SMA 3E8 and a biotinylated capturable component comprising SMA 4D8, or vice versa. Again, further antibodies that show a moderate to high affinity for hCG-H and a reduced or lower affinity for other antigens also could be used. The capture medium can include a capture component immobilized thereon. Preferably, the capture component comprises streptavidin; more preferably polymerized streptavidin being at least about 100 kDa in size.

Indirect Detection

In another aspect, the present invention provides devices wherein the detection is facilitated through selective removal of the hCG isoform. Such embodiments can particularly include a scavenger component (e.g., antibody) that is selectively or preferentially reactive with regular hCG. Accordingly, the scavenger component can exhibit minimal, if any, reactivity with hCG-H. In various embodiments, the scavenger component can be located at any position between the location of sample deposit and the capture site. Accordingly, the scavenger component effectively "subtracts out" the regular hCG from the sample, leaving primarily or only hCG-H available for sandwich formation and ultimately color development at the capture site. As such, these embodiments allow for the effective removal (e.g., by binding the regular hCG) of most (or all) regular hCG from the sample prior to contact with the capture site. With most or all of the regular hCG being effectively "subtracted out" of the sample, hCG-H will primarily be detected at the capture site.

In certain embodiments, the device includes a release medium comprising a labeled conjugate including a detectable label and a first binding member that is reactive with a first epitope common to regular hCG and hCG-H while the capture medium comprises a capture site including a second binding member that is reactive with a second epitope common to regular hCG and hCG-H. In one embodiment, the scavenger component can be located at any position downstream from the sample deposit and up to and including a region including the labeled conjugate. In another embodiment, the scavenger component can be located between a region including the labeled conjugate and a region including the capture site. In yet another embodiment, the scavenger component can be located at any region on the capture medium upstream from the capture site. Preferably, the scavenger component (e.g., antibody) exhibits a moderate to high affinity for regular hCG and is selectively or preferentially reactive with hCG.

As illustrated in FIG. 11, the device for detecting the presence or absence of hCG-H in a liquid sample, according to one embodiment, comprises a biphasic substrate 18 wherein the biphasic substrate 18 includes a release medium 30 formed of a first material and comprising a labeled conjugate 26 having a binding member reactive with a first epitope common to hCG-H and regular hCG and a capture medium 32 in fluid communication with the release medium 30. The capture medium 32 can be formed of a second, different material, and include a capture site 34 having immobilized thereon a member reactive with a second epitope common to hCG-H and regular hCG. Additionally, a detection device according such an embodiment includes a scavenger antibody 20 exhibiting substantially no reactivity with hCG-H. The scavenger antibody 20 can comprise a binding member selectively or preferentially reactive with hCG, wherein the scavenger antibody 20 can be located between a deposit location of the liquid sample and the capture site 34. The scavenger antibody can be releasably attached to the biphasic substrate 18 from any location between a sample deposit location and the capture site 34. As such, if hCG-H is present in the sample, a complex is formed comprising the labeled conjugate 26, hCG-H, and the immobilized reactive member 34.

In certain alternative embodiments, one or both of the labeled conjugate 26 and the immobilized binding member 34 can comprise a binding member that exhibits a moderate to high affinity for hCG-H and is selectively or preferentially reactive with hCG-H. In other embodiments, however, neither the labeled conjugate 26 nor the immobilized binding member 34 comprise a binding member that exhibits a moderate to high affinity for hCG-H while also being selectively or preferentially reactive with hCG-H.

According to various embodiments, the scavenger component (e.g., antibody) can be located downstream from the deposit location of the liquid sample and up to and including a region including the labeled conjugate. In other embodiments, the scavenger antibody can be located between a region including the labeled conjugate and a region including the capture site. Alternatively, the scavenger antibody can be located at any region on the capture medium upstream from the capture site.

In certain embodiments, the pregnancy device includes a release medium comprising a detectable label and a first binding member reactive with a first epitope common to hCG and hCG-H and a biotinylated capturable component comprising a second binding member reactive with a second epitope common to hCG and hCG-H. Such devices also include a capture medium including a capture site having immobilized thereon a capture component comprising streptavidin. According to such embodiments, a scavenger component can be located downstream from the sample deposit and up to and including a region including the labeled conjugate. In another embodiment, such devices can include a scavenger component located downstream from a region including the labeled conjugate and up to and including a region including the biotinylated capturable component. In yet another embodiment, the scavenger component can be located at any region on the capture medium upstream from the capture site. In such embodiments, the scavenger component effectively "subtracts out" the regular hCG from the sample, leaving primarily or only hCG-H available for sandwich formation and ultimately color development at the capture site. With the effective removal of regular hCG from the sample (e.g., by binding with the scavenger component), any hCG-H present in the sample forms a complex comprising the labeled conjugate, hCG-H, and the biotinylated capturable component.

As illustrated by FIG. 12, one embodiment of the invention comprises a device which includes a biphasic substrate 18. The biphasic substrate 18 can comprise a release medium 30 formed of a first material and a capture medium 32 in fluid communication with the release medium 30 and formed of a second, different material. The release medium 30 can include a labeled conjugate 26 comprising a binding member which is reactive with a first epitope common to hCG-H and hCG and a biotinylated capturable component 28 having a site reactive with a second epitope common to hCG-H or hCG. The embodiment illustrated by FIG. 12 includes the scavenger component 20 located upstream of the labeled conjugate 26. The scavenger component (e.g., antibody) 20 is preferably selectively or preferentially reactive with hCG. That is, the scavenger component 20 preferably exhibits substantially no reactivity with hCG-H. The scavenger component 20 can react with regular hCG present in the liquid sample to effectively "subtract out" regular hCG from the sample prior to the sample contacting the labeled conjugate 26. As such, the labeled conjugate will primarily bind to hCG-H and ultimately a complex is formed comprising the labeled conjugate 26, hCG-H, and the biotinylated capturable component 28. In these embodiments, the capture medium 32 can comprise a capture site 34 for capturing the complex, wherein the capture site 34 has immobilized thereon a capture component comprising streptavidin. In one preferred embodiment, the capture component comprises polymerized streptavidin, more preferably greater than 50% by weight of the polymerized streptavidin is at least about 100 kDa in size. Accordingly, the color development at the capture site 34 Various embodiments can also include a control site 36 located on the capture medium 32.

In certain alternative embodiments, one or both of the labeled conjugate 26 and the biotinylated capturable component 28 can comprise a binding member that exhibits a moderate to high affinity for hCG-H and is selectively or preferentially reactive with hCG-H. In other embodiments, however, neither the labeled conjugate 26 nor the biotinylated capturable component 28 comprise a binding member that exhibits a moderate to high affinity for hCG-H while also being selectively or preferentially reactive with hCG-H.

Ratiometric Detection

In another aspect, the present invention provides devices wherein detection is based on a ratiometric analysis. Such embodiments can include a mixture of binding members comprising a first group of binding members that are preferably (but not necessarily) selectively or preferentially reactive with an epitope of regular hCG and a second group of binding members that exhibit a moderate to high affinity for hCG-H and are selectively or preferentially reactive with an epitope of hCG-H. In certain embodiments, the first group of binding members that are selectively or preferentially reactive with an epitope of regular hCG are located at a different location than the second group of binding members that exhibit a moderate to high affinity for hCG-H and are selectively or preferentially reactive with an epitope of hCG-H. That is, each group of binding members can be striped independently of each other if desired. In one preferred embodiment, the binding members that are selectively or preferentially reactive with hCG-H comprise greater than 50% of the total number of binding members present in the mixture.

In various embodiments, the release medium includes different groups of binding antibodies (e.g., pooled together in a single stripe, striped independently of each other, or striped on top or each other) including a first group preferably (but not necessarily) being selectively or preferentially reactive with an epitope of regular hCG and a second group that exhibits a moderate to high affinity for hCG-H and are selectively or preferentially reactive with an epitope of hCG-H. Alternatively, the capture site can include different groups of capture antibodies including a first group preferably (but not necessarily) selectively or preferentially reactive with an epitope of regular hCG and a second group that exhibits a moderate to high affinity for hCG-H and are selectively or preferably reactive with an epitope of hCG-H. If desired, both the release medium and the capture medium can include the different groups of such antibodies (e.g., pooled together in a single stripe, striped independently of each other, or striped on top or each other).

In one preferred embodiment, the capture site comprises a mixture of regular hCG and hCG-H specific antibodies, wherein about 50% to about 98% of the antibodies are selectively or preferentially reactive with hCG-H and the remainder are selectively or preferentially reactive with regular hCG. Alternatively, the capture site can comprise about 70% to about 95% of capture antibodies being selectively or preferentially reactive with hCG-H, or from about 85% to about 95%, or from about 90% to about 95%. In one alternative embodiment, the capture site comprises about 90% to about 99% of capture antibodies selectively or preferentially reactive with hCG-H. In preferred embodiments, the hCG-H antibody or antibodies also exhibit a moderate to high affinity for hCG-H.

Such embodiments can allow for appropriate visual signal strength to be present at the test line regardless of when the device is employed during pregnancy. For instance, a user may choose to employ a pregnancy test device of the present invention later in pregnancy such as several weeks beyond the day of the missed period when the levels of hCG-H are reduced and the level of regular hCG present is proportionally higher. The discrimination by the hCG-H selective or preferential antibody or antibodies can allow specific detection of low levels of hCG-H in the sample during the early days of pregnancy, while the presence of the regular hCG antibodies will ensure a pregnant result throughout pregnancy. Thus, devices according to these embodiments can detect hCG-H in liquid samples having either low levels or high levels of hCG-H.

Multiple Line Assay

In yet another aspect of the present invention, the device can comprise a multiple line assay device for selectively detecting hCG-H in a liquid sample is provided. The device includes a release medium formed of a first material and comprising a detectable label and at least one binding member that exhibits a moderate to high affinity for hCG-H and is selectively or preferentially reactive with an epitope of hCG-H. Devices according to such embodiments also include at least one binding member that is reactive with an epitope of regular hCG and a capture medium in fluid communication with the release medium, wherein the release medium is preferably formed of a second, different material. The capture medium can include a first capture site that binds hCG-H and a second capture site that binds regular hCG. In addition to the two capture sites, the capture medium can also include a control site to indicate that the device is working properly. Accordingly, one embodiment of the present invention can have a capture medium with three lines or sites for possible color development. For instance, the second capture site that binds regular hCG can show the presence of total hCG indicating pregnancy. The first capture site can show the presence of hCG-H indicating viability of the pregnancy and the control site will show that the test is functional. As such, a viable pregnancy can be detected as well as confirmation that the device is functional by visual color development of all three sites. That is, a user will see three colored lines in the test window of the device.

As illustrated in FIG. 13 A-C, such embodiments can beneficially include a capture medium having separate capture sites within the window of the device, wherein one capture site is specific for regular hCG 100 and a second capture site is specific for hCG-H 200. Optionally, a third line comprising a control line 300 can be included so that a user can obtain three independent results. Specifically, devices according to these particular embodiments of the invention provide a user indication of test functionality (control line 300), pregnancy (detection of regular hCG 100), and the viability of the pregnancy (detection of hCG-H 200) in one test strip. For instance, FIG. 13A depicts test results conveying that the user is not pregnant and that the test device is working properly. FIG. 13B depicts test results conveying (1) that the user is pregnant; (2) the pregnancy is viable; and (3) that the device is functioning properly. FIG. 13C depicts test results for a user in which conception has occurred as evidenced by the color development at the test line 100, but that the pregnancy is likely not viable as evident by the lack of color development at the hCG-H line 200. Further, the color development at the control line 300 indicates that the device is working properly. As such, the test results indicate the occurrence of an early pregnancy loss, wherein the zygote will likely not successfully implant and proceed as a viable pregnancy.

In one embodiment, a multiple line assay device includes a release medium comprising a labeled conjugate including a detectable label and at least one binding member that is reactive with a first epitope of hCG-H and a labeled conjugate comprising a detectable label and at least one binding member that is reactive with a first epitope of regular hCG. Such devices also include a capture medium comprising a capture site including a binding member that is reactive with a second epitope of hCG-H and a separate capture site comprising a binding member that is reactive with a second epitope of regular hCG. In accordance with such embodiments, at least one of the binding members preferably exhibits a moderate to high affinity for hCG-H and is selectively or preferentially reactive with an epitope of hCG-H. In one embodiment, at least one of the binding members reactive with an epitope of regular hCG is preferably selectively or preferentially reactive with an epitope of regular hCG.

In yet another embodiment, a multiple line assay device can include a release medium comprising a labeled conjugate including a detectable label and at least one binding member that is reactive with an epitope common to both hCG-H and regular hCG. Further, the device can include a capture medium including a capture site comprising a binding member that exhibits a moderate to high affinity for hCG-H and is selectively or preferentially reactive with an epitope of hCG-H. The capture site can comprise a binding member that is reactive with an epitope of regular hCG.

According to various embodiments of the present invention, the device comprises a biphasic substrate including a release medium formed of a first material and a capture medium in fluid communication with the release medium and formed of a second, different material. The release medium includes a first labeled conjugate comprising a binding member that exhibits a moderate to high affinity for hCG-H and is selectively or preferentially reactive with an epitope of hCG-H and a second labeled conjugate comprising a binding member selectively or preferentially reactive with a first epitope of regular hCG. The capture medium can include a first capture site comprising an immobilized member that exhibits a moderate to high affinity for hCG-H and is selectively or preferentially reactive with a second epitope of hCG-H, such that if hCG-H is present in the sample, a sandwich complex is formed comprising the first labeled conjugate, hCG-H, and the first immobilized binding member. The capture medium preferably also includes a second capture site comprising a second immobilized binding member reactive with a second epitope of regular hCG, such that if hCG is present in the sample, a sandwich complex is formed comprising the second labeled conjugate, hCG, and the second immobilized binding member.

In yet another embodiment, the device can include a release medium comprising a labeled conjugate including a detectable label, at least one binding member reactive with a first epitope of hCG-H, and at least one binding member reactive with a first epitope of hCG. The release medium can also include a biotinylated capturable component comprising a binding member that exhibits a moderate to high affinity for hCG-H and is selectively or preferentially reactive with a second epitope of hCG-H. Such embodiments can include a capture medium including a capture site having immobilized thereon a capture component comprising streptavidin and a capture site comprising a binding member that is reactive with a second epitope of regular hCG.

In certain embodiments of the present invention, the device can include a release medium comprising a labeled conjugate including a detectable label, at least one binding member reactive with a first epitope of hCG-H, and at least one binding member reactive with a first epitope of regular hCG. The release medium can also include a biotinylated capturable component comprising a binding member that is selectively or preferentially reactive with a second epitope of regular hCG. In such embodiments, the capture medium comprises a capture site having immobilized thereon a capture component comprising streptavidin and a capture site comprising a binding member that is reactive with a second epitope of hCG-H.

In certain embodiments, the release medium formed of a first material can include a labeled conjugate comprising a binding member reactive with a first epitope of hCG-H and hCG (e.g., a common epitope of hCG-H and hCG), and a capture medium in fluid communication with the release medium and formed of a second, different material. The capture medium can include a first capture site comprising an immobilized binding member that exhibits a moderate to high affinity for hCG-H and is selectively or preferentially reactive with a second epitope of hCG-H, such that if hCG-H is present in the sample, a sandwich complex is formed comprising the labeled conjugate, hCG-H, and the first immobilized binding member. The capture medium can also include a second capture site comprising an immobilized member selectively or preferentially reactive with a second epitope of regular hCG, such that if regular hCG is present in the sample, a sandwich complex is formed comprising the second labeled conjugate, regular hCG, and the second immobilized binding member.

Multi-Strip Assay

In another aspect, the present invention provides a test device for selectively detecting hCG-H in a liquid sample which would allow multiple results to be conveyed to the consumer in one test kit by way of a multi-strip assay format. In such embodiments, two or more independent test strips share a common fluid path to convey independent results. FIG. 14 illustrates one such embodiment, wherein the device includes two strips, namely strip A 410 and strip B 440. The housing (not shown) of the pregnancy test device can be designed to accommodate two or more test strips. In a preferred embodiment, one of the strips is specific for regular hCG (e.g., Strip A 410 in FIG. 14) and the other strip is specific for hCG-H (e.g., Strip B 440 in FIG. 14). The strips can share a common sampling component 400, such as a urine wick, which would allow sample to be transferred to both strips simultaneously. Upon using the device, the consumer can preferably view two independent results windows, depicted as dashed lines on FIG. 14, to obtain the results. For instance, the appearance of a test line 100 in one window for strip A 410 on FIG. 14 can convey that the user is pregnant while the appearance of an hCG-H line 200 in an independent window for strip B 440 can convey that the pregnancy is viable, and likely at low risk for early pregnancy loss.

As depicted in FIG. 15, in another variation the capture mediums (e.g., nitrocellulose regions) of the two or more strips can be joined to a common release medium 480 and share a common fluid path 400 to convey two independent results. Again, the housing of the pregnancy test device can easily be designed to accommodate the larger unified test strip. In accordance with such embodiments, one portion of the device can be constructed to specifically detect regular hCG (Side A 410 in FIG. 15), and another portion can be constructed to specifically detect hCG-H (Side B 440 in FIG. 15). A common fluid path 400 (e.g., urine wick) can transfer sample to the release medium, whereby a labeling antibody can travel up both portions of the strip (e.g., side A 410 and side B 440 in FIG. 15). In certain embodiments, the individual portions (e.g., sides A and B) of the test strip can contain independent biotinylated antibodies; wherein one of the biotinylated antibodies specifically binds with an epitope of regular hCG 125 and the other biotinylated antibody specifically binds an epitope of hCG-H 225. Upon running the device a user can view two independent results windows, depicted as dashed lines on FIG. 15, to obtain the results. The appearance of color development at a test line in one window (e.g., side A of FIG. 15) can convey that the user is pregnant (i.e., color development at 150). The appearance of color development at an hCG-H line in an independent window (e.g., Side B of FIG. 15) can convey that the pregnancy is viable (i.e., color development at 250), and likely at low risk for early pregnancy loss.

Devices according to certain embodiments of the present invention can have a common fluid path for receiving and distributing the liquid sample and at least one release medium in fluid communication with the common fluid path. The at least one release medium can be formed of a first material and include a detectable label. Moreover, such embodiments can include a first capture medium in fluid communication with the at least one release medium and formed of a second material, wherein the first capture medium comprises a capture site that directly or indirectly selectively binds hCG-H. Devices according to these particular embodiments can include a second capture medium in fluid communication with the at least one release medium and formed of a third material. The second capture medium can comprise a capture site that directly or indirectly binds regular hCG. In one embodiment, the at least one release medium comprises a first release medium including a labeled conjugate comprising a detectable label and a binding member that is reactive with a first epitope of regular hCG-H and a second release medium comprising a labeled conjugate including a detectable label and a binding member that is reactive with a first epitope of regular hCG. Devices according to such embodiments include a first capture medium being in fluid communication with the first release medium; wherein the first capture medium can comprise a capture site including a binding member that exhibits a moderate to high affinity for hCG-H and is selectively or preferentially reactive with a second epitope of hCG-H. Such embodiments can include a second capture medium in fluid communication with the second release medium, wherein the second capture medium can comprise a capture site including a binding member that is reactive with a second epitope of regular hCG.

In certain embodiments, the device comprises a first biphasic substrate including (i) a first release medium formed of a first material and comprising a first labeled conjugate comprising a binding member that exhibits a moderate to high affinity for hCG-H and is selectively or preferentially reactive with a first epitope of hCG-H and (ii) a first capture medium in fluid communication with the first release medium and formed of a second, different material. The first capture medium comprises a first capture site comprising a first immobilized member predominantly reactive with a second epitope of hCG-H, such that if hCG-H is present in the sample, a sandwich complex is formed comprising the first labeled conjugate, hCG-H, and the first immobilized binding member. The device can also include a second biphasic substrate comprising (i) a second release medium formed of a first material and comprising a second labeled conjugate comprising a binding member selectively or preferentially reactive with a first epitope of regular hCG and (ii) a second capture medium in fluid communication with the second release medium and formed of a second, different material. The second capture medium can include a second capture site comprising a second immobilized binding member reactive with a second epitope of regular hCG, such that if regular hCG is present in the sample, a sandwich complex is formed comprising the second labeled conjugate, regular hCG, and the second immobilized binding member. Devices according to such embodiments can include a liquid sample deposit site being in fluid communication with both the first biphasic substrate and the second biphasic substrate. In certain embodiments of the present invention, the device can comprise a multi-strip assay device including a common release medium.

In yet another embodiment, a multi-strip device can include one or more release mediums. For instance, such a device can included a first release medium comprising a labeled conjugate including a detectable label and a binding member that is reactive with a first epitope of hCG-H and a biotinylated capturable component comprising a binding member that exhibits a moderate to high affinity for hCG-H and is selectively or preferentially reactive with a second epitope of hCG-H. Further, a second release medium can be provided, wherein the second release medium can comprise a labeled conjugate including a detectable label and a binding member that is reactive with a first epitope of regular hCG. These particular devices can include multiple capture mediums; wherein each capture medium can be in fluid communication with a respective release medium. For instance, such embodiments can include a first capture medium being in fluid communication with the first release medium. The first capture medium can comprise a capture site having immobilized thereon a capture component comprising monomeric or polymerized streptavidin. A second capture medium can also be provided as to be in fluid communication with the second release medium. The second capture medium can comprise a capture site including a binding member that is reactive with a second epitope of regular hCG. In one particular embodiment, the device can comprise a single release medium in fluid communication with both a first capture medium and a second capture medium. The release medium can comprise a labeled conjugate including a detectable label and a binding member that is reactive with a first epitope of hCG-H and a first epitope of regular hCG.

In yet another embodiment, the first capture medium can comprise a capture site including a binding member that exhibits a moderate to high affinity for hCG-H and is selectively or preferentially reactive with a second epitope of hCG-H. Further, the second capture medium can comprise a capture site including a binding member that is reactive with a second epitope of regular hCG. In another embodiment, the device can include a release medium comprising a biotinylated capturable component. The biotinylated capturable component preferably comprises a binding member that is selectively or preferentially reactive with a second epitope of hCG-H. As such, the first capture medium can comprise a capture site having immobilized thereon a capture component comprising monomeric or polymerized streptavidin.

In various embodiments, the device for detecting the presence of both regular hCG and hCG-H in a liquid sample can comprise a first biphasic substrate including a first release medium formed of a first material. The first release material can include a first labeled conjugate comprising a binding member that exhibits a moderate to high affinity for hCG-H and is selectively ore preferentially reactive with a first epitope of hCG-H and a first biotinylated capturable component having a site that exhibits a moderate to high affinity for hCG-H and is selectively or preferentially reactive with a second epitope of hCG-H, such that if hCG-H is present in the sample, a first sandwich complex is formed comprising the first labeled conjugate, hCG-H, and the first biotinylated capturable component. A first capture medium in fluid communication with the first release medium and formed of a second, different material, can be included. The first capture medium comprises a first capture site, for capturing the first complex, including an immobilized capture component comprising monomeric or polymerized streptavidin. In such embodiments, one or more additional biphasic substrates can be included for the detection of various hCG isoforms. In one preferred embodiment, the device includes a second biphasic substrate comprising a second release medium formed of a first material and comprising a second labeled conjugate comprising a binding member reactive with a first epitope of regular hCG and a second biotinylated capturable component having a site reactive with a second epitope of regular hCG, such that if regular hCG is present in the sample, a second complex is formed comprising the second labeled conjugate, regular hCG, and the second biotinylated capturable component. In a more preferred embodiment, at least one of the second labeled conjugate and the second biotinylated capturable component is selectively or preferentially reactive with regular hCG. Further, a device according to such embodiments includes a second capture medium in fluid communication with the second release medium and formed of a second, different material. The second capture medium comprises a second capture site for capturing the second complex including an immobilized capture component comprising monomeric or polymerized streptavidin. According to embodiments of the present invention, a deposit site for a liquid sample should preferably be in fluid communication with both the first biphasic substrate and the second biphasic substrate. In various embodiments, the device comprises a common release medium.

Viability of a Pregnancy

In another aspect, the present invention provides a method for evaluating the viability of a pregnancy. Such methods, according to various embodiments, allow a user to evaluate the viability of a pregnancy, wherein some methods comprise providing a test device according to any of the embodiments described herein and applying a liquid sample to the device. Preferably, the liquid sample potentially includes one or both regular hCG and hCG-H. Further, such methods include detecting the presence or lack thereof of hCG-H in the liquid sample. The detected presence of hCG-H indicates a high probability of a successful (or viable) pregnancy. In certain embodiments according to the present invention, the detection of hCG-H with test devices according to certain embodiments of the present invention indicates a probability of successful implantation and therefore a viable pregnancy of at least 50% (e.g., 50%-100%, 60%-90%, 70%-90%, etc.), at least 60% (60%-100%, 70%-90%, etc.), at least 70% (e.g., 70%-100%, 80%-100%, 80%-90%, etc.), at least 80% (80%-100%, 90%-95%, etc.), at least 90% (e.g., 90%-100%, 95%-99%), or at least 95% (e.g., 95%-100%).

In a study conducted using urine samples, term pregnancies had a mean hCG-H concentration of 6 mIU/mL on the day of implantation (compared to 2 mIU/mL hCG-H in Early Pregnancy Loss). See Sasaki et al. 2008: "Hyperglycosylated hCG and the source of Pregnancy Failures"; *Fertility and Sterility*, Volume 89, Issue 6, Pages 1781-1786. In this same study, in early pregnancy a greater than 50% proportion of hCG-H (out of total hCG) was required in order to proceed to term.

Example

A series of experiments were conducted to assess the relative affinities of the SMA4D8 and SMA3E8 antibodies. Both antibodies were analyzed by Biacore (GE Healthcare) and Enzyme-Linked ImmunoSorbent Assay ("ELISA").

Biacore is an instrument that helps analyze antibody—antigen interactions in terms of specificity, kinetics and affinity. Biacore exploits the phenomena of Surface Plasmon Resonance ("SPR"). Biacore allows the label free study of biomolecular interactions. More specifically, an antigen is coated onto a Biacore chip, and the relative affinities of different antibodies are probed in equilibrium. For instance, an antigen can be attached to the surface of a chip and a sample containing an antibody can be passed over the surface of the chip to evaluate the interaction between the antigen and antibody.

The ELISA is a multiwell plate assay that utilizes antibodies to detect the presence of an antigen in a sample. The ELISA assay allows 'antigen fingerprinting' to be performed. Antigen fingerprinting gives a snapshot of the differential recognition of antigens by a particular antibody. This method also allows one to determine the differential recognition of an antibody to various isoforms/subunits/fragments of a large molecule. This biochemical technique is used mainly in immunology to detect the presence of an antibody or an antigen in a sample. In simple terms, in ELISA an antigen is affixed to a surface, and then a specific antibody is washed over the surface so that it can bind to the antigen. This antibody is linked to an enzyme, and in the final step a substrate is added that the enzyme can convert to some detectable signal. Thus in the case of fluorescence ELISA, when light is shone upon the sample, any antigen/antibody complexes will fluoresce so that the amount of antigen in the sample can be measured.

Performing an ELISA involves at least one antibody and an antigen. The antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the presence or quantity of antigen in the sample.

SMA 4D8 Biacore Affinity Analysis

The Biacore instrument was utilized to study the biomolecular interactions between SMA 4D8 and particular antigens of interest. As such, the following antigens were coated onto a Biacore chip and SMA 4D8 was separately passed over the surface of the chip: (1) normally glycosylated hCG ($4^{th}$ IS, NIBSC); (2) free β hCG (NIBSC); (3) recombinant hCG (Sigma); (4) JEG-3 derived purified hCG-H; and (5) Luteinizing Hormone (LH) (NIBSC). After each injection of antibody over the chip, the Biacore chip was regenerated by passage of glycine at pH 1.5. Thus, the antigen concentration is constant for each injection of antibody. The concentrations used for the antibodies in each experiment vary (i.e., 1.0 to 12.5 μg/ml). The reason for this is that the antigen concentration is constant but the response to an antigen for each antibody differs and the aim was to provide a good range of binding curves from little binding to near saturation. The constants calculated for individual injections have been averaged. The calculated constants are: (1) KA–affinity at equilibrium; (2) KD–dissociation equilibrium constant; (3) ka–rate of complex formation; and (4) kd–rate of dissociation. These values are provided in Table 1 below. The Biacore sensorgrams for normally glycosylated hCG, free β hCG, recombinant hCG, and JEG-3 hCG-H are provided in FIGS. 16, 17, 18, and 19, respectively.

TABLE 1

| | KA | KD | Ka | Kd | Affinity | Stability |
|---|---|---|---|---|---|---|
| hCG-H (JEG3) | $1.65e^{10}$ | $1.06e^{-10}$ | $2.73e^5$ | $2.98e^{-5}$ | Good | Stable |
| Normally Glycosylated hCG | $4.57e^9$ | $2.45e^{-10}$ | $2.79e^5$ | $6.47e^{-5}$ | Moderate | Some dissociation |
| Recombinant hCG | $1.21e^8$ | $1.63e^{-9}$ | $1.09e^5$ | $9.45e^{-4}$ | Low | Unstable |
| Free beta-hCG | $3.45e^8$ | $3.26e^{-9}$ | $1.31e^5$ | $3.80e^{-4}$ | Low | Unstable |
| LH | — | — | — | — | — | No Binding |

As illustrated by the sensorgrams and the results summarized in Table 1, 4D8 displayed highest affinity for hCG-H and moderate affinity for normally glycosylated hCG with no LH cross-reactivity. As such, the epitope recognized by 4D8 may be influenced by glycosylation as it binds to recombinant hCG with a significantly reduced affinity compared to normally glycosylated hCG and hCG-H. Overall, the 4D8 Biacore results indicate a high affinity for hCG-H, a moderate affinity for normally glycosylated hCG, little affinity for recombinant hCG and no binding to LH.

SMA 4D8 ELISA Analysis

A sandwich ELISA assay was utilized to help determine the differential recognition of various antigens by SMA 4D8 when presented by another antibody. Accordingly, an 'antigen fingerprinting' was performed to provide a snapshot of the differential recognition of antigens by SMA 4D8 when presented by the mouse monoclonal antibody 11D6-2B10 coated on the microtiter plate. Additionally, the relative specificities for the different presented antigens were illustrated by comparisons made in parallel. The results of the ELISA analysis are summarized in FIG. 20. All results in FIG. 20 were normalized to 100% choriocarcinoma (hCG-H) binding in order to allow an accurate comparison of antigen specificities. FIG. 20 shows that SMA 4D8 exhibited a high specificity for choriocarcinoma derived hCG-H, a high specifity for Early Pregnancy Urine (EPU) derived hCG-H, moderate specifity for normally glycosylated (intact) hCG, moderate specifity for recombinant hCG, virtually no recognition for LH and virtually no recognition for Late Pregnancy Urine (LPU) derived hCG.

SMA 3E8 Biacore Affinity Analysis

The Biacore instrument was also utilized to study the biomolecular interactions between SMA 3E8 and particular antigens of interest. As such, the following antigens were coated onto a Biacore chip and SMA 3EA separately passed over the surface of the chip: (1) normally glycosylated hCG ($4^{th}$ IS, NIBSC); (2) free β hCG (NIBSC); (3) recombinant hCG (Sigma); (4) JEG-3 derived purified hCG-H; and (5) Luteinizing Hormone (LH) (NIBSC). After each injection of antibody over the chip, the Biacore chip was regenerated by passage of glycine at pH 1.5. Thus, the antigen concentration is constant for each injection of antibody. The concentrations used for the antibodies in each experiment vary (i.e., 1.0 to 12.5 μg/ml). The reason for this is that the antigen concentration is constant but the response to an antigen for each antibody differs and the aim was to provide a good range of binding curves from little binding to near saturation. The constants calculated for individual injections have been averaged. The calculated constants are: (1) KA–affinity at equilibrium; (2) KD–dissociation equilibrium constant; (3) ka–rate of complex formation; and (4) kd–rate of dissociation. These values are provided in Table 2 below. The sensorgrams for normally glycosylated hCG, free β hCG, recombinant hCG, and JEG-3 hCG-H are provided in FIGS. 21, 22, 23, and 24, respectively.

TABLE 2

| | KA | KD | Ka | Kd | Affinity | Stability |
|---|---|---|---|---|---|---|
| hCG-H (JEG3) | $2.27e^9$ | $6.52e^{-10}$ | $2.52e^5$ | $1.23e^{-4}$ | Moderate | Some dissociation |
| Normally Glycosylated hCG | $6.13e^{10}$ | $5.85e^{-10}$ | $1.47e^5$ | $4.92e^{-5}$ | Moderate | Reasonable |
| Recombinant hCG | $8.33e^8$ | $3.70e^{-9}$ | $1.50e^5$ | $4.165e^{-4}$ | Low | Unstable |
| Free beta-hCG | $4.35e^9$ | $2.99e^{-10}$ | $5.92e^5$ | $1.44e^{-4}$ | Moderate | Some dissociation |
| LH | $1.89e^7$ | $6.49e^{-8}$ | $1.59e^5$ | $9.12e^{-3}$ | Low | Rapid dissociation |

Overall, as illustrated by the sensorgrams and the results summarized in Table 2, 3E8 displayed a moderate affinity for hCG-H. 3E8 also displayed a moderate affinity for normally glycosylated hCG and free beta-hCG, and low affinity for recombinant hCG and LH.

SMA 3E8 ELISA Analysis

A sandwich ELISA assay was utilized to help determine the differential recognition of various antigens by SMA 3E8 when presented by another antibody. Accordingly, an 'antigen fingerprinting' was performed to provide a snapshot of the differential recognition of antigens by SMA 3E8 when presented by the mouse monoclonal antibody 11D6-2B10 coated onto the microtiter plate. Additionally, the relative specificities for the different presented antigens were illustrated by comparisons made in parallel. The results of the ELISA analysis are summarized in FIG. 25. All results in FIG. 25 were normalized to 100% choriocarcinoma (hCG-H) binding in order to allow an accurate comparison of antigen specificities. FIG. 25 shows that SMA 3E8 displays a high specifity for choriocarcinoma derived hCG-H, a high specifity for Early Pregnancy Urine (EPU) derived hCG-H, a moderate specifity for normally glycosylated hCG, a moderate specifity for recombinant hCG, a low specifity for LH, a high specifity for Late Pregnancy Urine (LPU) derived hCG, and a high specifity for beta core fragment.

B152 Biacore Affinity Analysis

To provide a comparison the embodiments of the present invention with an antibody known for exhibiting specific recognition of hCG-H, the Biacore instrument was also utilized to study the biomolecular interactions between B152 and particular antigens of interest. As such, the following antigens were coated onto a Biacore chip and B152 separately passed over the surface of the chip: (1) normally glycosylated hCG ($4^{th}$ IS, NIBSC); (2) free β hCG (NIBSC); (3) recombinant hCG (Sigma); (4) JEG-3 derived purified hCG-H; and (5) Luteinizing Hormone (LH) (NIBSC). After each injection of antibody over the chip, the Biacore chip was regenerated by passage of glycine at pH 1.5. Thus, the antigen concentration is constant for each injection of antibody. The concentrations used for the antibodies in each experiment vary. The reason for this is that the antigen concentration is constant but the response to an antigen for each antibody differs and the aim was to provide a good range of binding curves from little binding to near saturation. The constants calculated for individual injections have been averaged. The calculated constants are: (1) KA–affinity at equilibrium; (2) KD–dissociation equilibrium constant; (3) ka–rate of complex formation; and (4) kd–rate of dissociation. These values are provided in Table 3 below. The sensorgrams for normally glycosylated hCG, free β hCG, recombinant hCG, and JEG-3 hCG-H are provided in FIGS. 26, 27, 28, and 29, respectively.

TABLE 3

| | KA | KD | Ka | Kd | Affinity | Stability |
|---|---|---|---|---|---|---|
| hCG-H (JEG3) | $6.54e^8$ | $8.32e^{-9}$ | $1.39e^4$ | $8.31e^{-5}$ | Low | Unstable |
| Normally Glycosylated hCG | $2.14e^6$ | $1.72e^{-7}$ | $1.93e^3$ | $1.04e^{-3}$ | Negligible | Unstable |
| Recombinant hCG | $5.05e^7$ | $2.90e^{-8}$ | $2.20e^4$ | $4.04e^{-4}$ | Low | Unstable |
| Free beta-hCG | $1.04e^8$ | $2.14e^{-8}$ | $2.31e^5$ | $1.43e^{-3}$ | Low | Unstable |
| LH | — | — | — | — | — | No Binding |

Overall, as illustrated by the sensorgrams and the results summarized in Table 3, B152 exhibited a low affinity for hCG-H. The 7 injections illustrated by the sensograms on FIG. 29 show that concentration ranges between 20-100 micrograms/ml gave a response of 60-223 RU. Furthermore, at equilibrium the KA value of $6.54e^8$ and KD value of $8.32e^{-9}$ show that B152 has a low affinity for hCG-H. For comparison, the SMA 3E8 exhibited a KA value of $2.27e^9$ and a KD value of $6.52e^{-10}$ while SMA 4D8 exhibited a KA value of $1.65e^{10}$ and a KD value of $1.06e^{-10}$. Furthermore, the B152 concentration necessary (i.e., 100 micrograms/ml) to generate a response of 223 RU was about 50 to 100 times greater than that of SMA 3E8 and SMA 4D8. That is, to achieve a similar response to SMA 3E8 and SMA 4D8 the B152 concentration must be present at a concentration roughly a 100 times greater.

Comparison of Traditional Devices with Devices including an Antibody Exhibiting a Moderate to High Affinity for hCG-H As previously mentioned, FIGS. 2A-2C show the relative binding affinities for three antibody pairs (i.e., 3 separate devices each having a unique pair of antibodies) in which one of the binding members exhibits a moderate to high affinity for hCG-H in comparison to two production devices that are commercially available. FIGS. 2A-2C each illustrate the improvement in differential discrimination of hyperglycosylated hCG and recombinant hCG. In addition to comparing the relative affinities of these particular antibody pairs, their respective intensity of color development was also compared to the current production devices. As shown in FIG. 30, the color intensity (i.e., G//Dens—a measure of color intensity) of the three antibody pairs (i.e., CCFO1/3E8, CCFO1/4D8, and 11D6-2B10/4D8) were comparable to more intense than the FR1 devices (i.e., First Response Early Result pregnancy test devices from Church & Dwight Co., Inc.) compared to FR2 and FR1 devices. The FR2 devices (utilizing polymerized streptavidin) exhibited the best results. In certain embodiments according to the present invention, however, polymerized streptavidin can be utilized as the capture component.

Additionally, clinical urine sample testing was conducted for devices including these three particular antibody pairs (i.e., CCFO1/3E8, CCFO1/4D8, and 11D6-2B10/4D8). Once again, the results of these devices were compared to those of the current production devices. First, testing of hCG free urine samples of differing non-surge LH values (i.e., 0-60 mIU/ml) were conducted. As shown in FIG. 31, each of the devices correctly provided a "negative" result for all urine samples. Thus, devices including the CCFO1/3E8, CCFO1/4D8, and 11D6-2B10/4D8 antibody pairs desirably did not provide a single "false positive". Additional testing was conducted on hCG free urine samples of differing concentrations of LH surge samples (i.e., >130 mIU/ml). As shown in FIG. 32, each of the devices correctly provided a "negative" result for all urine samples. Again, devices including the CCFO1/3E8, CCFO1/4D8, and 11D6-2B10/4D8 antibody pairs desirably did not provide a single "false positive".

A large panel (200) of peri- and post-menopausal urine samples with varying levels of pituitary hCG were collected for another study. To evaluate the hCG-H detection of the poorly glycosylated pituitary derived hCG, 10 samples containing pituitary hCG (2.4 to 28.5 mIU) were selected form the larger sample set. As shown in FIG. 33, the FR2 devices incorrectly provided a positive result on seven occasions. In contrast, all devices for selectively detecting hCG-H correctly provided a negative results except for a single 11D6-2B10/4D8 device (tested against 28 mIU/ml of pituitary hCG). Thus, the devices for selectively detecting hCG-H provide a significant reduction in the detection of pituitary hCG when compared to production devices that assay total hCG.

Further testing of these particular devices for selectively detecting hCG-H was conducted on a two sets (Set A and Set B) of well characterized clinical urine samples from early pregnancy. The results of Set A are shown in FIG. 34 and the results of Set B are shown in FIG. 35. As shown in FIGS. 34 and 35, each of the devices for selectively detecting hCG-H showed similar results as the production devices in terms of giving a positive result prior to the day of an expected menstrual period (i.e., EMP on the FIGS). Beneficially, the 11D6-2B10/4D8 test devices provided positive results on at least day EMP-5 (i.e., 5 days prior to an expected menstrual period). Such an early detection of pregnancy is equal to or better than the results obtained by the FR1 devices.

Given the abundance of literature which contends that hCG-H is important for successful implantation to occur, a high proportion of early pregnancy loss (EPL) samples should theoretically exhibit low levels of hCG-H. To assess this, four cycles of women who suffered EPL were characterized and tested with both production and each of these particular devices for selectively detecting hCG-H (i.e., CCFO1/3E8, CCFO1/4D8, and 11D6-2B10/4D8). The results of this testing are provided in FIG. 36. As shown in FIG. 36, subjects THME and BRDA received positive results with the FR2 devices (based on total hCG assay) and possibly positive results with the FR1 devices (based on total hCG assay). The particular devices for selectively detecting hCG-H (i.e., CCFO1/3E8, CCFO1/4D8, and 11D6-2B10/4D8), however, all correctly provided negative results due to the absence of hCG-H in the samples when tested. Beneficially, the 11D6-2B10/4D8 devices consistently gave negative results for every sample.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device for selectively detecting hyperglycosylated human chorionic gonadotropin (hCG-H) in a liquid sample deposited directly or indirectly on a proximal portion of the device for transport to a distal portion of the device, wherein the device comprises:
   A) a release medium formed of a first material and comprising a labeled conjugate with a detectable label and a first binding member that is reactive with at least one of an epitope of hCG-H or an epitope of human chorionic gonadotropin (hCG); and
   B) a capture medium in fluid communication with the release medium and formed of a second, different material, the capture medium comprising a capture site that comprises a second binding member immobilized on the capture medium, said second binding member being reactive with at least one of an epitope of hCG-H or an epitope of hCG;
   wherein at least one of the release medium and the capture medium comprises a binding member that exhibits a moderate to high affinity for hCG-H and is selectively or preferentially reactive with hCG-H, and wherein it is only the second binding member that exhibits the moderate to high affinity for hCG-H and is selectively or preferentially reactive with hCG-H.

2. A method of evaluating the viability of a pregnancy, the method comprising:
A) providing a test device comprising the device of claim 1;
B) applying to the device a liquid sample potentially including one or both of regular hCG and hCG-H; and
C) detecting the presence or lack thereof of hCG-H in the liquid sample,
wherein the detected presence of hCG-H indicates a high probability of successful implantation and therefore a viable pregnancy.

3. A device for selectively detecting hyperglycosylated human chorionic gonadotropin (hCG-H) in a liquid sample deposited directly or indirectly on a proximal portion of the device for transport to a distal portion of the device, wherein the device comprises:
A) a release medium formed of a first material and comprising a detectable label;
B) a capture medium in fluid communication with the release medium and formed of a second, different material, the capture medium comprising a capture site; and
C) a scavenger component that is selectively or preferentially reactive with regular hCG, the scavenger component being located between a location of sample deposit and the capture site;
wherein at least one of the release medium and the capture medium comprises a binding member that is reactive with hCG-H.

4. The device of claim 3, wherein:
A) the release medium comprises a labeled conjugate comprising the detectable label and a first binding member that is reactive with a first epitope of hCG-H; and
B) the capture medium comprises a capture site comprising a second binding member that is reactive with a second epitope of hCG-H.

5. The device of claim 4, wherein at least one of the first binding member and the second binding member exhibits a moderate to high affinity for hCG-H and is selectively or preferentially reactive with hCG-H.

6. The device of claim 4, wherein the scavenger component is located downstream from the sample deposit and up to and including a region including the labeled conjugate.

7. The device of claim 4, wherein the scavenger component is located between a region including the labeled conjugate and a region including the capture site.

8. The device of claim 4, wherein the scavenger component is located at any region on the capture medium upstream from the capture site.

9. The device of claim 4, wherein:
A) the release medium comprises:
i) the detectable label and a first binding member reactive with a first epitope of hCG-H; and
ii) a capturable component comprising a second binding member reactive with a second epitope of hCG-H, such that in the presence of hCG-H in the sample, a complex is formed comprising the labeled conjugate, hCG-H, and the capturable component; and
B) the capture medium comprises a capture site having immobilized thereon a capture component having a binding affinity for the capturable component.

10. The device of claim 9, wherein the capturable component comprises a biotinylated capturable component and the capture component comprises streptavidin.

11. The device of claim 9, wherein at least one of the first binding member and the second binding member exhibits a moderate to high affinity for hCG-H and is selectively or preferentially reactive with hCG-H.

12. The device of claim 9, wherein the scavenger component is located downstream from the sample deposit and up to and including a region including the labeled conjugate.

13. The device of claim 9, wherein the scavenger component is located between a region including the labeled conjugate and a region including the capture site.

14. The device of claim 9, wherein the scavenger component is located at any region on the capture medium upstream from the capture site.

15. A method of evaluating the viability of a pregnancy, the method comprising:
A) providing a test device comprising the device of claim 3;
B) applying to the device a liquid sample potentially including one or both of regular hCG and hCG-H; and
C) detecting the presence or lack thereof of hCG-H in the liquid sample,
wherein the detected presence of hCG-H indicates a high probability of successful implantation and therefore a viable pregnancy.

16. A device for selectively detecting hyperglycosylated human chorionic gonadotropin (hCG-H) in a liquid sample deposited directly or indirectly on a proximal portion of the device for transport to a distal portion of the device, wherein the device comprises:
A) a release medium formed of a first material and comprising:
(i) a first group of labeled conjugates comprising a detectable label and a binding member that is selectively or preferentially reactive with an epitope of regular hCG; and
(ii) a second group of labeled conjugates comprising a detectable label and a binding member is selectively or preferentially reactive with an epitope of hCG-H and exhibits a moderate to high affinity for hCG-H; and
B) a capture medium in fluid communication with the release medium and formed of a second, different material, the capture medium comprising a capture site having immobilized thereon at least one group of binding members;
wherein the binding members that are selectively or preferentially reactive with hCG-H comprise greater than 50% of the total number of binding members present on the release medium.

17. The device of claim 16, wherein the first and second groups of labeled conjugates are provided as a mixture.

18. The device of claim 16, wherein the first group of labeled conjugates is located at a different location on the release medium than the second group of labeled conjugates.

19. A method of evaluating the viability of a pregnancy, the method comprising:
A) providing a test device comprising the device of claim 16;
B) applying to the device a liquid sample potentially including one or both of regular hCG and hCG-H; and
C) detecting the presence or lack thereof of hCG-H in the liquid sample,
wherein the detected presence of hCG-H indicates a high probability of successful implantation and therefore a viable pregnancy.

20. A device for selectively detecting hyperglycosylated human chorionic gonadotropin (hCG-H) in a liquid sample deposited on a proximal portion of the device for transport to a distal portion of the device, wherein the device comprises:
- A) a release medium formed of a first material and comprising a detectable label;
- B) at least one binding member that exhibits a moderate to high affinity for hCG-H and is selectively or preferentially reactive with an epitope of hCG-H;
- C) at least one binding member that is reactive with an epitope of regular hCG; and
- D) a capture medium in fluid communication with the release medium and formed of a second, different material, the capture medium comprising:
  - (i) a first capture site that binds hCG-H; and
  - (ii) a second capture site that binds regular hCG.

21. The device of claim 20, wherein the at least one binding member reactive with an epitope of regular hCG is selectively or preferentially reactive with an epitope of regular hCG.

22. The device of claim 20, wherein:
- A) the release medium comprises:
  - i) a labeled conjugate comprising a detectable label and
  - ii) at least one binding member that is reactive with a epitope common to regular hCG and hCG-H; and
- B) the capture medium comprises:
  - i) a capture site comprising a binding member that is reactive with a second epitope of hCG-H; and
  - ii) a capture site comprising a binding member that is reactive with a second epitope of regular hCG;
- wherein at least one of the binding members reactive with an epitope of hCG-H exhibits a moderate to high affinity for hCG-H and is selectively or preferentially reactive with hCG-H.

23. The device of claim 22, wherein at least one of the binding members reactive with an epitope of regular hCG is selectively or preferentially reactive with an epitope of regular hCG.

24. The device of claim 20, wherein
- A) the release medium comprises:
  - i) a labeled conjugate comprising a detectable label and at least one binding member reactive with an epitope common to regular hCG and hCG-H; and
  - ii) a capturable component comprising a binding member that exhibits a moderate to high affinity for hCG-H and is selectively or preferentially reactive with a second epitope of hCG-H; and
- B) the capture medium comprises:
  - i) a first capture site having immobilized thereon a capture component having a binding affinity for the capturable component; and
  - ii) a second capture site comprising an immobilized binding member that is reactive with a second epitope of hCG.

25. The device of claim 24, wherein the capturable component comprises a biotinylated capturable component and the capture component comprises streptavidin.

26. The device of claim 20, wherein
- A) the release medium comprises:
  - i) a labeled conjugate comprising a detectable label and at least one binding member reactive with an epitope common to regular hCG and hCG-H; and
  - ii) a capturable component comprising a binding member that is selectively or preferentially reactive with a second epitope of regular hCG; and
- B) the capture medium comprises:
  - i) a first capture site having immobilized thereon a capture component having a binding affinity for the capturable component; and
  - ii) a second capture site comprising an immobilized binding member that exhibits a moderate to high affinity for hCG-H and is selectively or preferentially reactive with a second epitope of hCG-H.

27. The device of claim 26, wherein the capturable component comprises a biotinylated capturable component and the capture component comprises streptavidin.

28. A method of evaluating the viability of a pregnancy, the method comprising:
- A) providing a test device comprising the device of claim 20;
- B) applying to the device a liquid sample potentially including one or both of regular hCG and hCG-H; and
- C) detecting the presence or lack thereof of hCG-H in the liquid sample,
- wherein the detected presence of hCG-H indicates a high probability of successful implantation and therefore a viable pregnancy.

29. A device for selectively detecting hyperglycosylated human chorionic gonadotropin (hCG-H) in a liquid sample, the device comprising:
- A) a common fluid path for receiving and distributing the liquid sample;
- B) at least one release medium in fluid communication with the common fluid path, the at least one release medium being formed of a first material and comprising a detectable label;
- C) a first capture medium in fluid communication with the at least one release medium and formed of a second material, the first capture medium comprising a capture site that directly or indirectly selectively or preferentially binds hCG-H; and
- D) a second capture medium in fluid communication with the at least one release medium and formed of the second material, the second capture medium comprising a capture site that directly or indirectly binds regular hCG.

30. The device of claim 29, wherein:
- A) the at least one release medium comprises:
  - i) a first release medium comprising a labeled conjugate comprising a detectable label and a binding member that is reactive with a first epitope of hCG-H; and
  - ii) a second release medium comprising a labeled conjugate comprising a detectable label and a binding member that is reactive with a first epitope of regular hCG;
- B) the first capture medium being in fluid communication with the first release medium, the first capture medium comprising a capture site comprising a binding member that exhibits a moderate to high affinity for hCG-H and is selectively or preferentially reactive with a second epitope of hCG-H; and
- C) the second capture medium being in fluid communication with the second release medium, the second capture medium comprising a capture site comprising a binding member that is selectively or preferentially reactive with a second epitope of regular hCG.

31. The device of claim 29, wherein:
- A) the at least one release medium comprises:
  - i) a first release medium comprising a labeled conjugate comprising a detectable label and a binding member that is reactive with a first epitope of hCG-H, and further comprising a capturable component comprising a binding member that exhibits a moderate to high affinity for hCG-H and is selectively or preferentially reactive with a second epitope of hCG-H; and ii) a second release medium comprising a labeled conjugate comprising a detectable label and a binding member that is reactive with a first epitope of regular hCG;

B) the first capture medium being in fluid communication with the first release medium, the first capture medium comprising a capture site having immobilized thereon a capture component having a binding affinity for the capturable component; and C) the second capture medium being in fluid communication with the second release medium, the second capture medium comprising a capture site comprising a binding member that is reactive with a second epitope of regular hCG.

32. The device of claim 31, wherein the capturable component comprises a biotinylated capturable component and the capture component comprises streptavidin.

33. The device of claim 29, comprising a single release medium in fluid communication with both the first capture medium and the second capture medium, the release medium comprising a labeled conjugate comprising a detectable label and a binding member that is reactive with a first epitope of hCG-H and a first epitope of regular hCG.

34. The device of claim 29, wherein the first capture medium comprises a capture site comprising a binding member that exhibits a moderate to high affinity for hCG-H and is selectively or preferentially reactive with a second epitope of hCG-H; and the second capture medium comprises a capture site comprising a binding member that is reactive with a second epitope of regular hCG.

35. A method of evaluating the viability of a pregnancy, the method comprising:

A) providing a test device comprising the device of claim 29;

B) applying to the device a liquid sample potentially including one or both of regular hCG and hCG-H; and C) detecting the presence or lack thereof of hCG-H in the liquid sample, wherein the detected presence of hCG-H indicates a high probability of successful implantation and therefore a viable pregnancy.

* * * * *